US011485698B2

(12) United States Patent
Shimizu

(10) Patent No.: US 11,485,698 B2
(45) Date of Patent: Nov. 1, 2022

(54) METHOD FOR PRODUCING ACETIC ACID

(71) Applicant: DAICEL CORPORATION, Osaka (JP)

(72) Inventor: Masahiko Shimizu, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 567 days.

(21) Appl. No.: 16/483,808

(22) PCT Filed: Jul. 25, 2018

(86) PCT No.: PCT/JP2018/027894
§ 371 (c)(1),
(2) Date: Aug. 6, 2019

(87) PCT Pub. No.: WO2019/230007
PCT Pub. Date: Dec. 5, 2019

(65) Prior Publication Data
US 2021/0355063 A1    Nov. 18, 2021

(30) Foreign Application Priority Data

May 29, 2018   (WO) .................. PCT/JP2018/020603

(51) Int. Cl.
*C07C 51/12*    (2006.01)
*B01J 23/46*    (2006.01)
(Continued)

(52) U.S. Cl.
CPC ............. *C07C 51/12* (2013.01); *B01J 23/468* (2013.01); *B01J 27/08* (2013.01); *B01J 31/0231* (2013.01); *C07C 51/445* (2013.01); *C07C 51/48* (2013.01)

(58) Field of Classification Search
CPC .......... C07C 51/12; C07C 51/45; C07C 51/48; C07C 51/44; C07C 53/08; B01J 23/468; B01J 27/08; B01J 31/0231
See application file for complete search history.

(56) References Cited

U.S. PATENT DOCUMENTS 4,204,915 A     5/1980  Kurata et al.
5,371,286 A    12/1994  Blay et al.
(Continued)

FOREIGN PATENT DOCUMENTS

EP   0 645 362 A1    3/1995
EP   3 333 147 A1    6/2018
(Continued)

OTHER PUBLICATIONS

Extended European Search Report dated Oct. 7, 2019, in European Patent Application No. 18855140.2.
(Continued)

*Primary Examiner* — Deborah D Carr
(74) *Attorney, Agent, or Firm* — Birch, Stewart, Kolasch & Birch, LLP

(57) ABSTRACT

Provided is a method capable of industrially efficiently producing acetic acid yielding a good potassium permanganate test result, without costing much. In the acetic acid production method, (1) by-produced acetaldehyde is industrially advantageously removed from a process stream, and (2) a crotonaldehyde concentration in an acetic acid stream from a light ends column is controlled to a specific level or lower, and/or a reflux ratio at a second distillation column is controlled to 0.1 or more. In addition, (3) the method includes the step of subjecting at least one of an aqueous phase and an organic phase of a light ends column overhead condensate to distillation in a crotonaldehyde-removing column; the light ends column is operated at a reflux ratio of 2 or more (when the aqueous phase is refluxed); and the
(Continued)

crotonaldehyde-removing column is operated so as to meet a specific condition(s).

18 Claims, 6 Drawing Sheets

(51) Int. Cl.
  *B01J 27/08* (2006.01)
  *B01J 31/02* (2006.01)
  *C07C 51/44* (2006.01)
  *C07C 51/48* (2006.01)

(56) References Cited

U.S. PATENT DOCUMENTS

| | | | |
|---|---|---|---|
| 5,625,095 A | 4/1997 | Miura et al. | |
| 5,723,660 A | 3/1998 | Morimoto et al. | |
| 6,143,930 A | 11/2000 | Singh et al. | |
| 9,006,483 B2 | 4/2015 | Shimizu et al. | |
| 9,260,369 B1 | 2/2016 | Liu et al. | |
| 9,540,304 B2 | 1/2017 | Liu et al. | |
| 2015/0025270 A1 | 1/2015 | Shimizu et al. | |
| 2016/0137576 A1 | 5/2016 | Liu et al. | |

FOREIGN PATENT DOCUMENTS

| | | | | | |
|---|---|---|---|---|---|
| JP | 53-116314 A | | 10/1978 | | |
| JP | 4-295445 A | | 10/1992 | | |
| JP | 04295445 A | * | 10/1992 | ............. | C07C 51/12 |
| JP | 7-25813 A | | 1/1995 | | |
| JP | 7-133249 A | | 5/1995 | | |
| JP | 07133249 A | * | 5/1995 | ............. | C07B 63/00 |
| JP | 8-67650 A | | 3/1996 | | |
| JP | 08067650 A | * | 3/1996 | ............. | C07C 51/12 |
| JP | 2001-508405 A | | 6/2001 | | |
| JP | 2016-117709 A | | 6/2016 | | |
| JP | 2016117709 A | * | 6/2016 | ............. | B01J 23/464 |
| WO | WO 96/33965 A1 | | 10/1996 | | |
| WO | WO-9633965 A1 | * | 10/1996 | .......... | B01J 31/0231 |
| WO | WO 2013/137236 A1 | | 9/2013 | | |
| WO | WO-2013137236 A1 | * | 9/2013 | ............. | B01D 3/009 |
| WO | WO 2018/078924 A1 | | 5/2018 | | |
| WO | WO-2018078924 A1 | * | 5/2018 | ............... | B01D 1/30 |

OTHER PUBLICATIONS

Extended European Search Report for European Application No. 18857376.0, dated Nov. 27, 2019.
International Search Report dated Jul. 31, 2018, in PCT/JP2018/020605.
International Search Report for PCT/JP2018/027894 (PCT/ISA/210) dated Sep. 4, 2018.
Written Opinion of the International Searching Authority for PCT/JP2018/027894 (PCT/ISA/237) dated Sep. 4, 2018.
English translation of the Written Opinion of the International Searching Authority dated Oct. 22, 2019, in PCT/JP2018/027894 (Forms PCT/IB/310 and PCT/IB/237).
International Search Report dated Sep. 4, 2018, in PCT/JP2018/027894.
Extended European Search Report dated May 28, 2020, in European Patent Application No. 18903038.0.
U.S. Appl. No. 16/334,659, filed Mar. 19, 2019, Unassigned.
U.S. Appl. No. 16/334,654, filed Mar. 19, 2019, Unassigned.
U.S. Appl. No. 16/334,673, filed Mar. 19, 2019, Unassigned.

* cited by examiner

[FIG. 1]
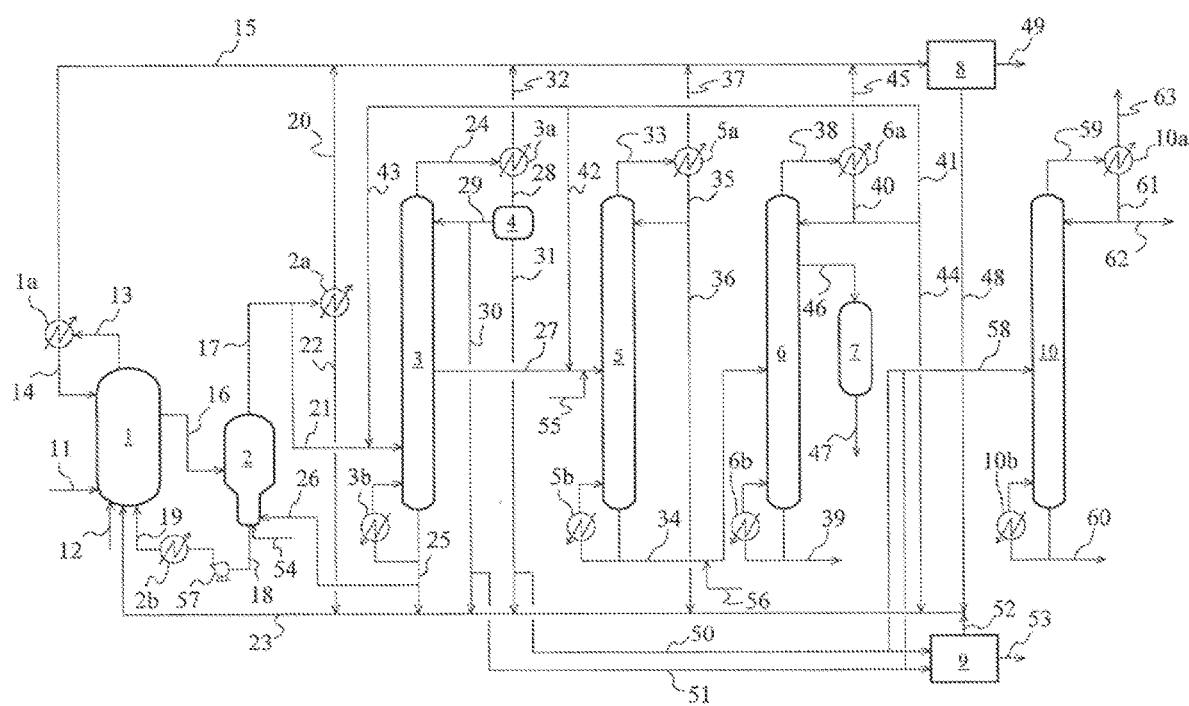

[FIG. 2]
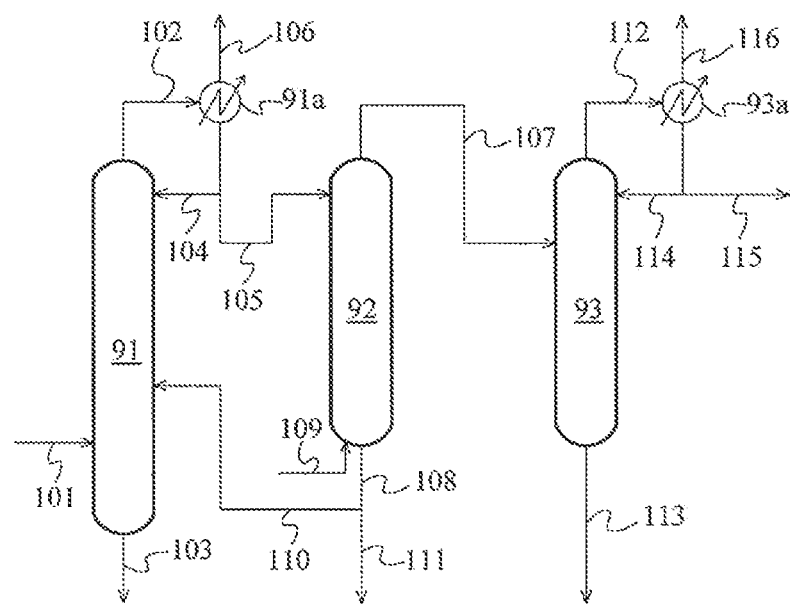

[FIG. 3]
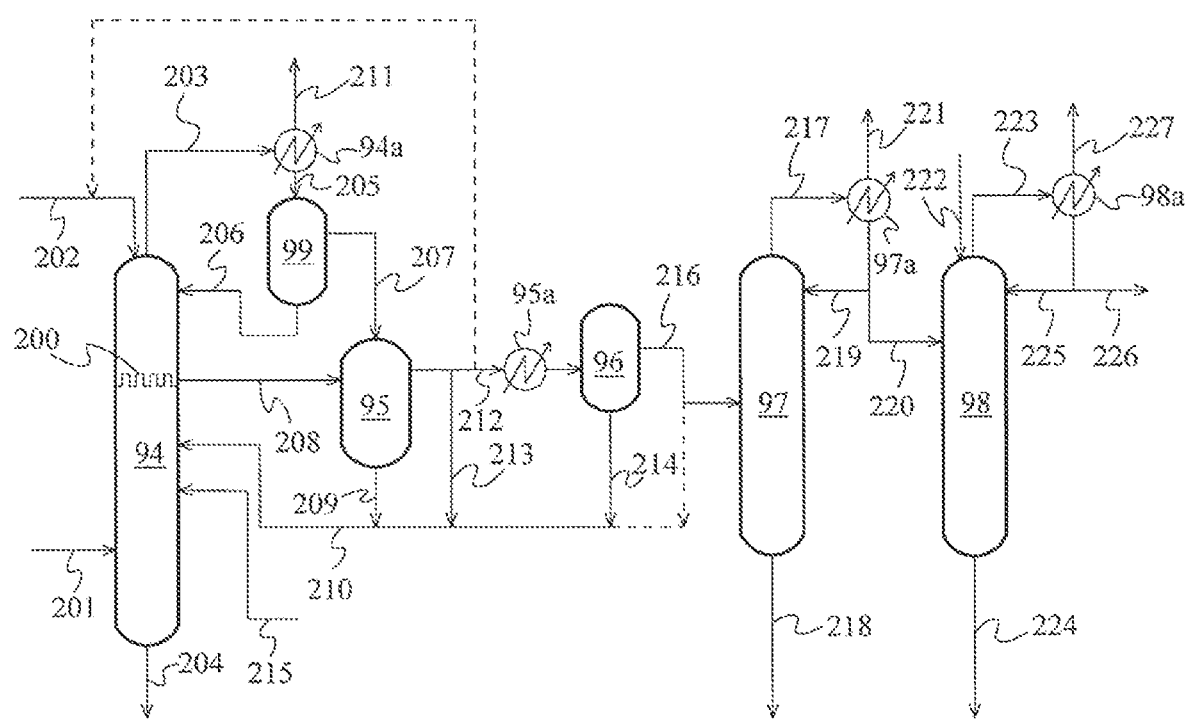

[FIG. 4]
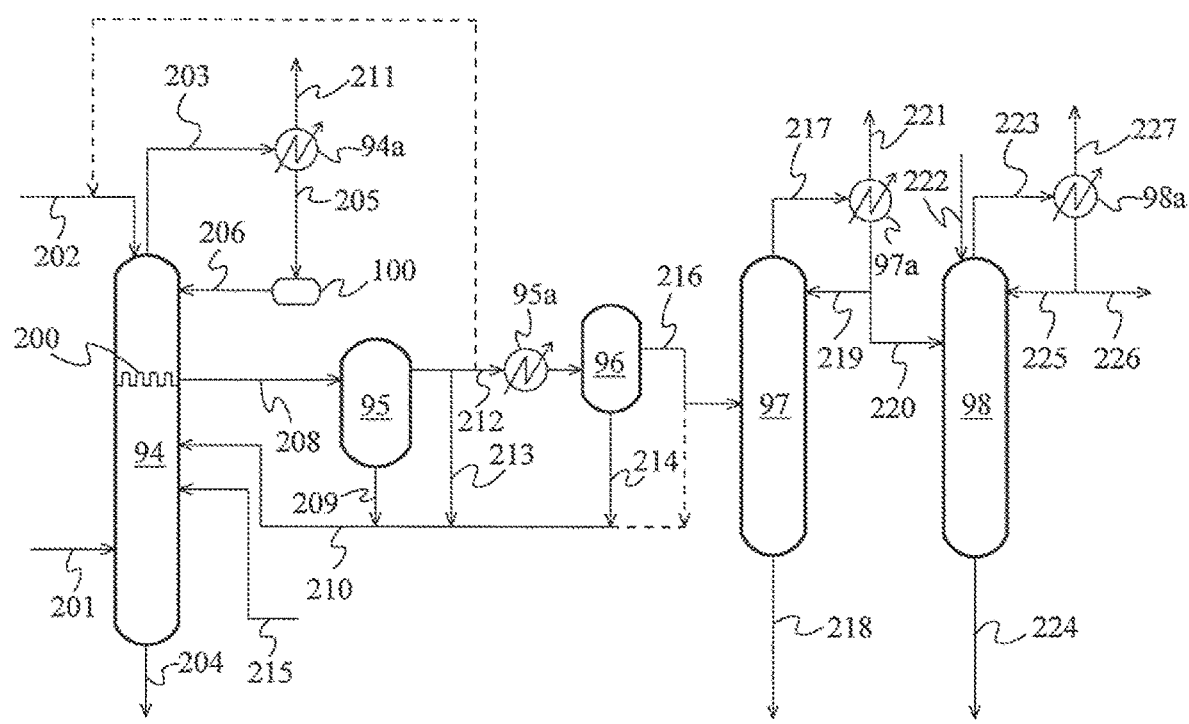

[FIG. 5]
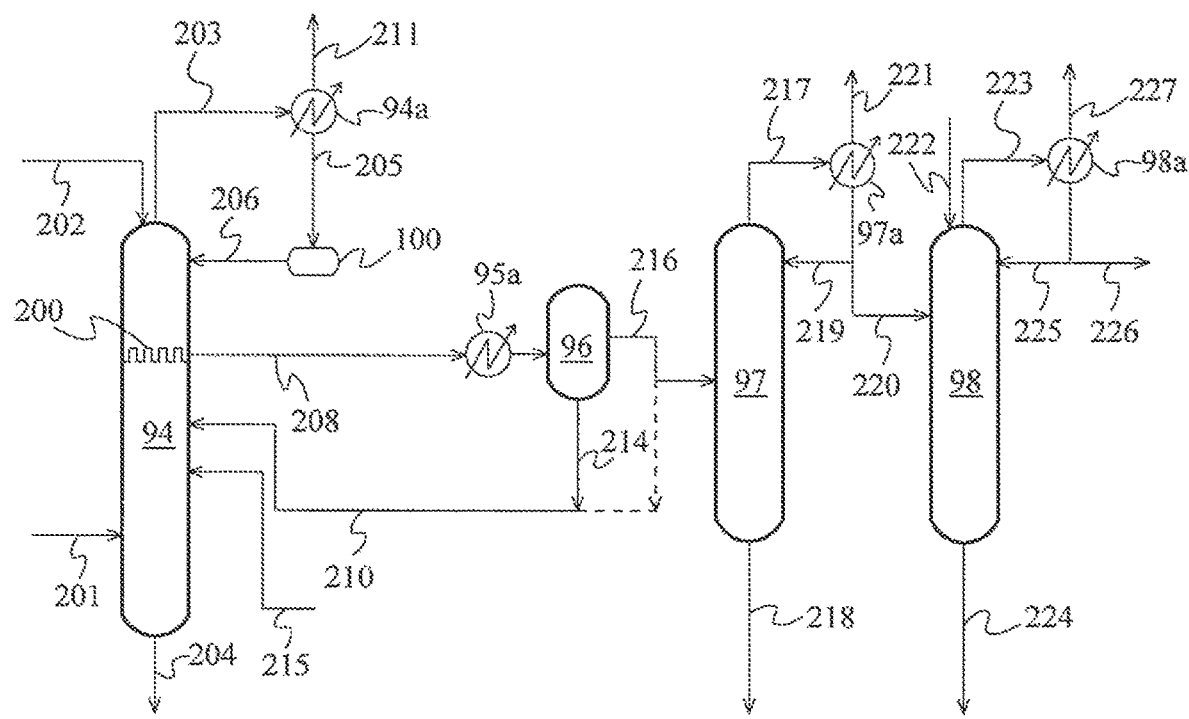

[FIG. 6]
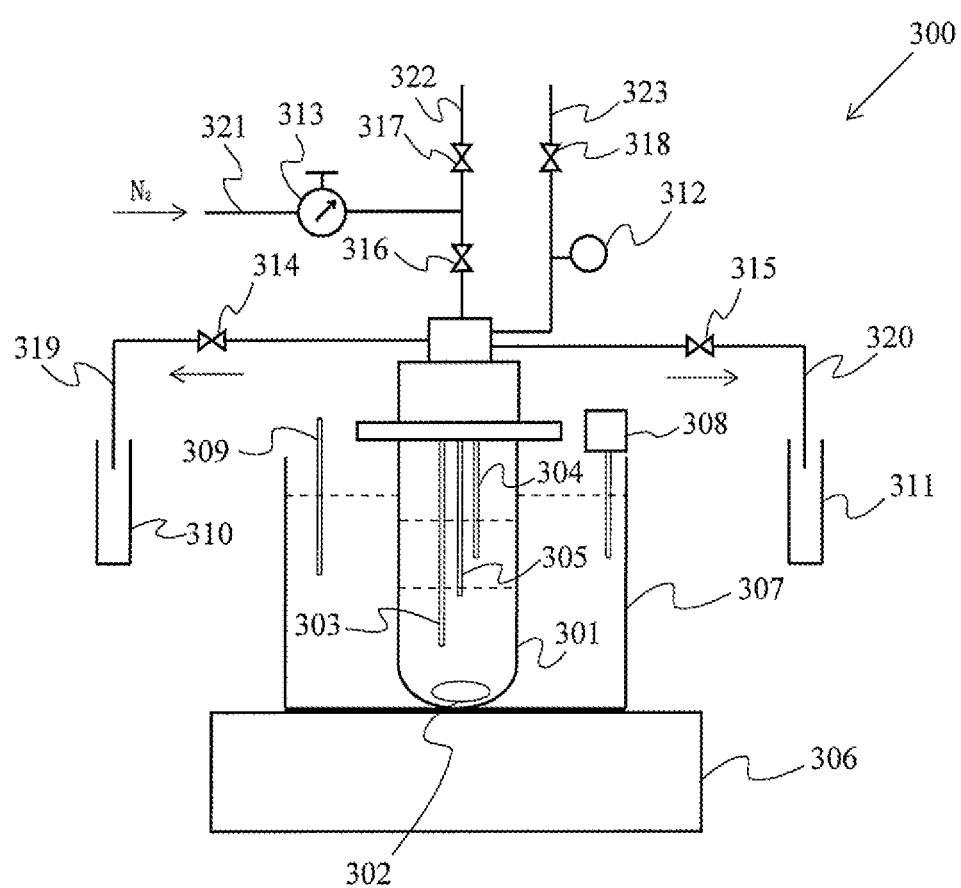

METHOD FOR PRODUCING ACETIC ACID

TECHNICAL FIELD

The present invention relates to methods for producing acetic acid. This application claims priority to PCT Application Number PCT/JP2018/20603, filed on May 29, 2018, the entire contents of which are incorporated herein by reference.

BACKGROUND ART

A methanol carbonylation process is known as a process for industrially producing acetic acid. According to this process, for example, methanol is allowed to react with carbon monoxide in the presence of a catalyst in a reactor to form acetic acid in a reaction mixture, the resulting reaction mixture is separated, using an evaporator, into a vapor phase including acetic acid and light ends, and a residual liquid phase (residue phase) including acetic acid and the catalyst, the vapor phase is subjected to distillation in a distillation column (light ends column) to be separated into an overhead stream including light ends, and an acetic acid stream, and the acetic acid stream is further purified to give an acetic acid product. In the process, acetaldehyde is by-produced during the reaction, and the acetaldehyde causes the acetic acid product to have lower quality.

The acetaldehyde is converted into crotonaldehyde by aldol condensation and causes the acetic acid product to yield a worse potassium permanganate test result (permanganate time). In addition, crotonaldehyde is converted into 2-ethylcrotonaldehyde by aldol condensation with acetaldehyde; and 2-ethylcrotonaldehyde also causes the acetic acid product to yield a worse potassium permanganate test result. However, as compared with 2-ethylcrotonaldehyde, crotonaldehyde more adversely affects the potassium permanganate test result per mass unit, and when contained in the acetic acid product, more significantly worsens the quality of the product.

To decrease acetaldehyde, crotonaldehyde, and/or 2-ethylcrotonaldehyde, there have been conventionally industrially employed roughly classified two techniques, namely, techniques (i) and (ii) as follows (Patent Literature (PTL) 1 and PTL 2). In the technique (i), the formation of crotonaldehyde in the reaction system is restrained by liquid-liquid separating a condensate into an aqueous phase and an organic phase using a decanter, where the condensate is derived from an overhead stream from a light ends column, subjecting, of the two phases, the aqueous phase to distillation in an acetaldehyde-removing column, extracting a condensate with water to separate and remove acetaldehyde from the condensate, where the condensate includes acetaldehyde and methyl iodide and is derived from an overhead stream from the acetaldehyde-removing column, and thereby decreasing acetaldehyde in methyl iodide to be recycled to the reaction system. In the technique (ii), crotonaldehyde is directly decomposed by oxidation with ozone, where the crotonaldehyde is contained in a crude acetic acid which is obtained in the middle of a purification step. However, facilities for the acetaldehyde separation and removal, and facilities for the ozone treatment are both expensive. Conventional acetic acid production processes entirely depend on these techniques so as to give an acetic acid product yielding a better potassium permanganate test result, and this leads to increase in installation cost.

The methanol-acetic acid process is known to give alkanes as impurities. Such alkanes as impurities contain 3 or more carbon atoms and have higher boiling points as compared with methyl iodide and methyl acetate. The alkanes are mainly saturated or unsaturated hydrocarbons, but may contain an oxygen atom and/or an iodine atom in the molecule. Japanese Unexamined Patent Application Publication (JP-A) No. H04-295445 discloses a technique for removing the alkanes. In the technique, of overhead condensates from a light ends column, an organic phase is subjected to distillation in a distillation column (alkane-removing column), to give an overhead product including methyl iodide, methyl acetate, and carbonyl impurities, and bottoms including alkanes, water, and acetic acid; the overhead product is recycled to the reactor or fed to an acetaldehyde-removing column, the bottoms are combined with and extracted with water to give an aqueous phase including acetic acid, and an organic phase including alkanes; the aqueous phase is recycled to the reactor, and the organic phase including the alkanes is discarded as a waste. This literature, however, neither discloses nor indicates how to give an acetic acid product yielding a better potassium permanganate test result.

CITATION LIST

Patent Literature

PTL 1: JP-A No. H07-25813
PTL 2: Japanese Unexamined Patent Application Publication (JP-A) (Translation of PCT Application) No. 2001-508405
PTL 3: JP-A No. H04-295445

SUMMARY OF INVENTION

Technical Problem

As a result of investigations, the inventor of the present invention found that such a technique as disclosed in PTL 2 tends to give higher separation efficiency, where the technique subjects, of two phases resulting from liquid-liquid separation in the decanter at the light ends column, an aqueous phase to distillation in the acetaldehyde-removing column. This is because the aqueous phase generally has a higher acetaldehyde concentration as compared with the organic phase. However, according to the technique, the liquid containing a large amount of water is subjected to distillation, and this requires larger treatment energy, because water has a high latent heat of vaporization. In addition, the technique requires distillators made of a material that has very high corrosion resistance and is thereby expensive, because methyl iodide contained in a small amount in the aqueous phase gives, through hydrolysis, hydrogen iodide, and the hydrogen iodide tends to corrode distillators. The treatment of the aqueous phase requires a comparable number of plates in the distillation column as compared with the after-mentioned case where the organic phase (methyl iodide phase) is subjected to distillation in the acetaldehyde-removing column. This is because a significant amount of methyl iodide is present in the aqueous phase, and the treatment of the aqueous phase requires not only separation of water, but also separation between methyl iodide and acetaldehyde, which have a small difference in boiling point from each other.

In another known technique, of the two phases resulting from liquid-liquid separation in the decanter at the light ends column, an organic phase is subjected to distillation in the acetaldehyde-removing column, and a condensate derived from an overhead stream from the column is extracted with water, to thereby remove acetaldehyde. This technique has the advantage of requiring smaller treatment energy, because the principal component of the organic phase is methyl iodide, which has a low latent heat of vaporization. In addition, the technique has the advantage of less causing corrosion as compared with the treatment of the aqueous phase. However, the technique has the disadvantage of having lower separation efficiency, because the organic phase is found to generally have a lower acetaldehyde concentration as compared with the aqueous phase, as a result of the investigations by the inventor as described above. Thus, the technique of subjecting the aqueous phase to an acetaldehyde-removing treatment and the technique of subjecting the organic phase to an acetaldehyde-removing treatment each have advantages and disadvantages.

Accordingly, the present invention has an object to provide a method for industrially efficiently producing acetic acid yielding a good potassium permanganate test result, without costing much.

The present invention has another object to provide a method for industrially advantageously separating and removing by-produced acetaldehyde, in consideration of advantages and disadvantages of the technique of subjecting an aqueous phase to an acetaldehyde-removing treatment, and of the technique of subjecting an organic phase to an acetaldehyde-removing treatment, where the aqueous phase and the organic phase result from liquid-liquid separation of a process stream in a liquid-liquid separation step, and where the process stream results from the methanol carbonylation process.

Solution to Problem

After intensive investigations to achieve the objects, the inventor found that high-quality acetic acid yielding a good potassium permanganate test result can be industrially efficiently obtained without requiring large-scale treatment facilities, by controlling a crotonaldehyde concentration in a first acetic acid stream to a specific level or lower, where the first acetic acid stream is an acetic acid stream resulting from removal of light ends using a light ends column in a methanol carbonylation process.

In addition, the inventor found that bottoms from a dehydration column can have a lower crotonaldehyde concentration and can yield a significantly better potassium permanganate test result, by operating the light ends column with a reflux ratio at a specific level or higher, providing a distillation column (crotonaldehyde-removing column) with which an overhead condensate from the light ends column is treated, and operating the crotonaldehyde-removing column under specified conditions. More specifically, at a higher reflux ratio at the light ends column, crotonaldehyde is more concentrated at the column top of the distillation column (light ends column), because crotonaldehyde has a boiling point (104° C.) lower than the boiling point (117° C.) of acetic acid. Such concentrated crotonaldehyde, when recycled to the reactor, reacts, in the reactor, with acetaldehyde to form 2-ethylcrotonaldehyde. The crotonaldehyde in the reactor also reacts with hydrogen to form butyl alcohol, and the butyl alcohol in turn reacts with acetic acid to give butyl acetate. As compared with crotonaldehyde, 2-ethylcrotonaldehyde less adversely affects the potassium permanganate test result; and butyl alcohol and butyl acetate do not approximately adversely affect, and are harmless to, the potassium permanganate test result. Thus, acetic acid tends to have still better quality. At such a higher reflux ratio of the light ends column, 2-ethylcrotonaldehyde and butyl acetate are present in further lower concentrations at the column top, because 2-ethylcrotonaldehyde and butyl acetate have boiling points respectively of 137° C. and 126° C., higher than the boiling point (117° C.) of acetic acid. The two components are recycled in bottoms from the light ends column to the reaction system and concentrated, or a part of the two components is fed from (fed as) a sidecut to a subsequent step, or is contained in the acetic acid product, where the sidecut is drawn at a height level higher than the level at which the charge liquid is fed. On the other hand, the light ends column overhead condensate containing concentrated crotonaldehyde is subjected to a distillation treatment separately from the acetaldehyde-removing treatment. This enables efficient separation of useful methyl iodide from unnecessary crotonaldehyde. Specifically, for example, distillation treatment of the organic phase, of the light ends column overhead condensate, gives methyl iodide as overhead products together with methyl acetate. These can be recycled to the reactor and/or a decanter in which the light ends column overhead condensate is stored. The treatment also gives crotonaldehyde as bottoms which also include other high-boiling impurities (such as 2-ethylcrotonaldehyde, butyl acetate, and alkanes), and acetic acid. The bottoms are removed out of the system and discarded. Water may be concentrated at the column top, or drawn from the column bottom. A conventionally known alkane-removing column may be used as the crotonaldehyde-removing column. Such an alkane-removing column may be operated continuously, but may be operated batchwise when alkanes are formed at low rates. The batchwise operation may cause the acetic acid product to yield a worse potassium permanganate test result. To eliminate or minimize this and to maintain the product quality, at least one of an acetaldehyde-removing treatment, an ozone treatment, and change or adjustment in operation conditions should be performed. In this connection, 2-ethylcrotonaldehyde is present in a trace amount at the light ends column top. The operation can discharge this 2-ethylcrotonaldehyde out of the system, and thereby contributes to a better potassium permanganate test result, as in the case of crotonaldehyde. However, advantageous effects of this are limited, because 2-ethylcrotonaldehyde, which has a high boiling point, is hardly concentrated at the column top of the light ends column. Of the light ends column overhead condensate, mainly the organic phase is fed to the crotonaldehyde-removing column. In addition to, or instead of this, the aqueous phase of the light ends column overhead condensate may be fed to the crotonaldehyde-removing column. Thus, the acetic acid product can yield a better potassium permanganate test result by the easy and simple procedure as above. This can downsize or eliminate acetaldehyde-removing facilities and ozone treatment facilities, and can reduce steam cost and electric utility expense.

The inventor also performed liquid-liquid equilibrium experiments that assume chemical compositions of condensates derived from overhead streams from the light ends column, while focusing the partition coefficient of acetaldehyde under different conditions in the liquid-liquid separation step, where the acetaldehyde partition coefficient is the ratio of the acetaldehyde concentration in the aqueous phase to the acetaldehyde concentration in the organic phase. As a result, the inventor found that, when the condensate is liquid-liquid separated, in a decanter at the light ends column, into an aqueous phase and an organic phase, the acetaldehyde partition coefficient has a certain correlation to the acetaldehyde concentration in the aqueous phase, the acetaldehyde concentration in the organic phase, the liquid temperature in liquid-liquid separation, the methyl acetate concentration in the aqueous phase, and the methyl acetate concentration in the organic phase. As described above, the technique of subjecting the aqueous phase to an acetaldehyde-removing treatment, and the technique of subjecting the organic phase to an acetaldehyde-removing treatment each have advantages and disadvantages. Accordingly, it is industrially advantageous to employ the former technique when the acetaldehyde partition coefficient is at some high level (when a relatively larger amount of acetaldehyde is distributed to the aqueous phase); to employ the latter technique when the acetaldehyde partition coefficient is at some low level (when a relatively larger amount of acetaldehyde is distributed to the organic phase); and to employ both the two techniques when the acetaldehyde partition coefficient falls within an intermediate region between the two levels. In particular, the technique of subjecting the aqueous phase to an acetaldehyde-removing treatment, when employed, requires equipment and facilities that are highly corrosion resistant and are expensive. This requires strict determination of the acetaldehyde partition coefficient. On the basis of these findings and considerations, the inventor found that an object (target) to be subjected to the acetaldehyde-removing treatment can be determined rationally.

The present invention has been made on the basis of these findings and further investigations.

Specifically, the present invention provides, in one aspect, a method for producing acetic acid as follows (this method is hereinafter also referred to as a "first acetic acid production method"). The method includes a carbonylation step, a separation step, a liquid-liquid separation step, an acetaldehyde-removing step, a recycling step, and a crotonaldehyde-removing step.

In the carbonylation step, methanol is carbonylated with carbon monoxide in a reactor in the presence of a catalytic system, acetic acid, methyl acetate, and water, to form acetic acid in a reaction mixture, where the catalytic system includes a metal catalyst and methyl iodide.

In the separation step, the reaction mixture from the carbonylation step is separated, using at least one selected from evaporators and distillation columns, into a stream including the metal catalyst, an acetic acid stream rich in acetic acid, and a stream richer in light ends than the acetic acid stream.

In the liquid-liquid separation step, a process stream including water, acetic acid, methyl iodide, and acetaldehyde is liquid-liquid separated into an aqueous phase and an organic phase.

In the acetaldehyde-removing step, acetaldehyde derived from the process stream is removed from an object by a treatment, where the object is selected from at least a part of at least one of the aqueous phase and the organic phase on the basis of a factor or factors selected from the group consisting of a liquid temperature in the liquid-liquid separation in the liquid-liquid separation step, an acetaldehyde concentration in at least one of the aqueous phase and the organic phase, an acetaldehyde partition coefficient, a methyl acetate concentration in at least one of the aqueous phase and the organic phase, and a methyl acetate partition coefficient.

In the recycling step, at least a part of at least one of the aqueous phase and the organic phase is recycled to the reactor.

In the crotonaldehyde-removing step, crotonaldehyde is removed from at least another part of at least one of the aqueous phase and the organic phase by a distillation treatment in a distillation column.

The separation step includes the substep of yielding, by separation using a first distillation column, a first acetic acid stream rich in acetic acid, and an overhead stream richer in light ends than the first acetic acid stream. In the substep, a crotonaldehyde concentration in the first acetic acid stream is controlled to 2.2 ppm by mass or less.

In the separation step, a reflux ratio at the first distillation column is controlled so that: the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column.

In the crotonaldehyde-removing step, the distillation column is operated so as to meet at least one of conditions (a-i) to (a-iii) as follows:

(a-i) a reflux ratio at the distillation column is 0.01 or more;

(a-ii) at the distillation column, the ratio of a crotonaldehyde concentration (ppm by mass) in a distillate to a crotonaldehyde concentration (ppm by mass) in a charge liquid is less than 1; and (a-iii) at the distillation column, the ratio of a crotonaldehyde concentration (ppm by mass) in bottoms to a crotonaldehyde concentration (ppm by mass) in the charge liquid is greater than 1.

The present invention also provides, in another aspect, a method for producing acetic acid as follows (this method is hereinafter also referred to as a "second acetic acid production method"). The method includes a carbonylation step, a separation step, a liquid-liquid separation step, an acetaldehyde-removing step, a recycling step, and a crotonaldehyde-removing step.

In the carbonylation step, methanol is reacted (carbonylated) with carbon monoxide in a reactor in the presence of a catalytic system, acetic acid, methyl acetate, and water, to form acetic acid in a reaction mixture, where the catalytic system includes a metal catalyst and methyl iodide.

In the separation step, the reaction mixture from the carbonylation step is separated, using at least one selected from evaporators and distillation columns, into a stream including the metal catalyst, an acetic acid stream rich in acetic acid, and a stream richer in light ends than the acetic acid stream.

In the liquid-liquid separation step, a process stream including water, acetic acid, methyl iodide, and acetaldehyde is liquid-liquid separated into an aqueous phase and an organic phase.

In the acetaldehyde-removing step, acetaldehyde derived from the process stream is removed from an object by a treatment, where the object is selected from at least a part of at least one of the aqueous phase and the organic phase on the basis of a factor or factors selected from the group consisting of a liquid temperature in the liquid-liquid separation in the liquid-liquid separation step, an acetaldehyde concentration in at least one of the aqueous phase and the organic phase, an acetaldehyde partition coefficient, a methyl acetate concentration in at least one of the aqueous phase and the organic phase, and a methyl acetate partition coefficient.

In the recycling step, at least a part of at least one of the aqueous phase and the organic phase is recycled to the reactor.

In the crotonaldehyde-removing step, crotonaldehyde is removed from at least another part of at least one of the aqueous phase and the organic phase by a distillation treatment in a distillation column.

The separation step includes the substep of yielding, by separation using a first distillation column, a first acetic acid stream rich in acetic acid, and a first overhead stream richer in light ends than the first acetic acid stream; and the substep of separating the first acetic acid stream, using a second distillation column, into a second overhead stream rich in water, and a second acetic acid stream richer in acetic acid than the first acetic acid stream.

In the substeps, a crotonaldehyde concentration in the first acetic acid stream is controlled to 2.2 ppm by mass or less, and/or a reflux ratio at the second distillation column is controlled to 0.1 or more.

In the separation step, a reflux ratio at the first distillation column is controlled so that: the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column.

In the crotonaldehyde-removing step, the distillation column is operated so as to meet at least one of conditions (a-i) to (a-iii) as follows:

(a-i) a reflux ratio at the distillation column is 0.01 or more;

(a-ii) at the distillation column, the ratio of a crotonaldehyde concentration (ppm by mass) in a distillate to a crotonaldehyde concentration (ppm by mass) in a charge liquid is less than 1; and (a-iii) at the distillation column, the ratio of a crotonaldehyde concentration (ppm by mass) in bottoms to a crotonaldehyde concentration (ppm by mass) in the charge liquid is greater than 1.

In the acetic acid production methods according to the present invention, it is preferred that the liquid-liquid separation step meets at least one of conditions (b-i) to (b-v), and at least a part of the aqueous phase is subjected to the treatment in the acetaldehyde-removing step, where the conditions (b-i) to (b-v) are expressed as follows:

(b-i) the aqueous phase has an acetaldehyde concentration of 28.1 mass percent or less, and/or the organic phase has an acetaldehyde concentration of 24.8 mass percent or less;

(b-ii) the liquid-liquid separation is performed at a temperature of 70° C. or lower;

(b-iii) the aqueous phase has a methyl acetate concentration of 12.0 mass percent or less, and/or the organic phase has a methyl acetate concentration of 47.6 mass percent or less, and/or the totality of the methyl acetate concentration in the aqueous phase and the methyl acetate concentration in the organic phase is 59.6 mass percent or less;

(b-iv) an acetaldehyde partition coefficient is 1.1 or more, where the acetaldehyde partition coefficient is the ratio of the acetaldehyde concentration (mass percent) in the aqueous phase to the acetaldehyde concentration (mass percent) in the organic phase; and (b-v) a methyl acetate partition coefficient is 0.25 or more, where the methyl acetate partition coefficient is the ratio of the methyl acetate concentration (mass percent) in the aqueous phase to the methyl acetate concentration (mass percent) in the organic phase.

In the acetic acid production methods according to the present invention, the liquid-liquid separation step preferably meets all the conditions (b-i), (b-ii), (b-iii), (b-iv), and (b-v).

In the acetic acid production methods according to the present invention, it is preferred that the liquid-liquid separation step meets at least one of conditions (b'-i) to (b'-v), and at least a part of the organic phase is subjected to the treatment in the acetaldehyde-removing step, where the conditions (b'-i) to (b'-v) are expressed as follows:

(b'-i) the aqueous phase has an acetaldehyde concentration of 0.045 mass percent or more, and/or the organic phase has an acetaldehyde concentration of 0.013 mass percent or more;

(b'-ii) the liquid-liquid separation is performed at a temperature of −5° C. or higher;

(b'-iii) the aqueous phase has a methyl acetate concentration of 1.2 mass percent or more, and/or the organic phase has a methyl acetate concentration of 2.2 mass percent or more, and/or the totality of the methyl acetate concentration in the aqueous phase and the methyl acetate concentration in the organic phase is 3.4 mass percent or more;

(b'-iv) an acetaldehyde partition coefficient is 4.1 or less, where the acetaldehyde partition coefficient is the ratio of the acetaldehyde concentration (mass percent) in the aqueous phase to the acetaldehyde concentration (mass percent) in the organic phase; and (b'-v) a methyl acetate partition coefficient is 0.8 or less, where the methyl acetate partition coefficient is the ratio of the methyl acetate concentration (mass percent) in the aqueous phase to the methyl acetate concentration (mass percent) in the organic phase.

In the acetic acid production methods according to the present invention, the liquid-liquid separation step preferably meets all the conditions (b'-i), (b'-ii), (b'-iii), (b'-iv), and (b'-v).

The separation step in the acetic acid production methods according to the present invention preferably includes an evaporation step and a light ends-removing step. In the evaporation step, the reaction mixture from the carbonylation step is separated, by evaporation in an evaporator, into a vapor stream and a residue stream (residual liquid stream). In the light ends-removing step, the vapor stream is separated, using the first distillation column, into a first overhead stream rich in at least one light end selected from methyl iodide and acetaldehyde, and the first acetic acid stream rich in acetic acid, and the first overhead stream is subjected to condensation and liquid-liquid separation to give an aqueous phase and an organic phase.

The separation step in the acetic acid production methods according to the present invention preferably includes a dehydration step. In the dehydration step, the first acetic acid stream is separated, using a second distillation column, into a second overhead stream rich in water, and a second acetic acid stream richer in acetic acid than the first acetic acid stream.

The second acetic acid stream has a crotonaldehyde concentration of typically 2.0 ppm by mass or less.

The second acetic acid stream has an 2-ethylcrotonaldehyde concentration of typically 3.0 ppm by mass or less.

The second acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less.

The second acetic acid stream has a butyl acetate concentration of typically 15 ppm by mass or less.

The second acetic acid stream has a ratio ($C_{CR}/C_{BA}$) of the crotonaldehyde concentration $C_{CR}$ (ppm by mass) to the butyl acetate concentration $C_{EA}$ (ppm by mass) of typically 2.0 or less.

The catalytic system in the acetic acid production methods according to the present invention may further include an ionic iodide.

In the acetic acid production methods according to the present invention, at least a part of a residue may be recycled to the reactor, where the residue is a residue remained after the removal of acetaldehyde from at least a part of at least one of the aqueous phase and the organic phase.

The reactor is operated at a hydrogen partial pressure of typically 0.001 MPa (absolute pressure) or more.

A liquid reaction mixture in the reactor has an acetaldehyde concentration of typically 500 ppm by mass or less.

The second acetic acid stream may have a crotonaldehyde concentration of 0.98 ppm by mass or less, and/or an 2-ethylcrotonaldehyde concentration of 1.0 ppm by mass or less, and/or a butyl acetate concentration of 15 ppm by mass or less.

The second acetic acid stream preferably yields a potassium permanganate test result of longer than 50 minutes.

In the acetic acid production methods according to the present invention, the vapor stream to be fed to the first distillation column may have a crotonaldehyde concentration of 0 to 5.0 ppm by mass, and/or an 2-ethylcrotonaldehyde concentration of 0 to 3.0 ppm by mass, and/or a butyl acetate concentration of 0.1 to 13.0 ppm by mass.

The first acetic acid stream has an 2-ethylcrotonaldehyde concentration of typically 3.0 ppm by mass or less.

The first acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less.

The first acetic acid stream has a butyl acetate concentration of typically 15 ppm by mass or less.

The first acetic acid stream has a ratio ($C_{CR}/C_{BA}$) of the crotonaldehyde concentration $C_{CR}$ (ppm by mass) to the butyl acetate concentration $C_{EA}$ (ppm by mass) of typically 2.0 or less.

The first acetic acid stream may have a crotonaldehyde concentration of 1.3 ppm by mass or less, and/or an 2-ethylcrotonaldehyde concentration of 1.0 ppm by mass or less, and/or a butyl acetate concentration of 15 ppm by mass or less.

The charge liquid to the distillation column in the crotonaldehyde-removing step has a crotonaldehyde concentration of typically 0.01 to 50 ppm by mass.

The distillation column in the crotonaldehyde-removing step is preferably operated so as to meet all the conditions (a-i) to (a-iii).

The distillation in the crotonaldehyde-removing step may be performed batchwise.

The distillation column in the crotonaldehyde-removing step is operated at a throughput of typically 0.0001 to 50 parts by mass per 100 parts by mass of the vapor stream fed to the first distillation column.

The acetic acid production methods according to the present invention may further include a scrubbing step. In the scrubbing step, a process offgas is absorptively treated with an absorbing solvent including acetic acid and is thereby separated into a carbon monoxide-rich stream and an acetic acid-rich stream.

Advantageous Effects of Invention

The present invention enables industrially efficient production of high-quality acetic acid yielding a good potassium permanganate test result ("permanganate time", also called "chameleon time"), even without providing large-scale facilities such as ozone treatment facilities, by control of the crotonaldehyde concentration in an acetic acid stream (first acetic acid stream) from the light ends column to a specific level or lower. The present invention also enables industrially efficient production of high-quality acetic acid yielding a good potassium permanganate test result, even without providing facilities such as ozone treatment facilities, by operation of the light ends column with a reflux ratio at a specific level or higher, and efficient removal of crotonaldehyde by the crotonaldehyde-removing step. In addition, the present invention enables industrially advantageous removal of acetaldehyde with high efficiency, where the acetaldehyde is by-produced in the methanol carbonylation process, by selection of an object (target) to be treated in the acetaldehyde-removing step from at least a part of at least one of the aqueous phase and the organic phase, on the basis of a factor or factors selected from the group consisting of the liquid temperature in the liquid-liquid separation in the liquid-liquid separation step, the acetaldehyde concentration in at least one of the aqueous phase and the organic phase, the acetaldehyde partition coefficient, the methyl acetate concentration in at least one of the aqueous phase and the organic phase, and the methyl acetate partition coefficient.

BRIEF DESCRIPTION OF DRAWINGS

FIG. 1 is an acetic acid production flow chart according to one embodiment of the present invention;

FIG. 2 is a schematic flow chart illustrating an acetaldehyde-removing system according to an embodiment;

FIG. 3 is a schematic flow chart illustrating an acetaldehyde-removing system according to another embodiment;

FIG. 4 is a schematic flow chart illustrating an acetaldehyde-removing system according to yet another embodiment;

FIG. 5 is a schematic flow chart illustrating an acetaldehyde-removing system according to still another embodiment; and FIG. 6 is a schematic diagram of a liquid-liquid equilibrium measuring apparatus used in experimental examples in the present invention.

DESCRIPTION OF EMBODIMENTS

The first acetic acid production method according to the present invention includes a carbonylation step, a separation step, a liquid-liquid separation step, an acetaldehyde-removing step, a recycling step, and a crotonaldehyde-removing step.

In the carbonylation step, methanol is reacted (carbonylated) with carbon monoxide in a reactor in the presence of a catalytic system, acetic acid, methyl acetate, and water, to form acetic acid in a reaction mixture, where the catalytic system includes a metal catalyst and methyl iodide.

In the separation step, the reaction mixture from the carbonylation step is separated, using at least one selected from evaporators and distillation columns, into a stream including the metal catalyst, an acetic acid stream rich in acetic acid, and a stream richer in light ends than the acetic acid stream.

In the liquid-liquid separation step, a process stream including water, acetic acid, methyl iodide, and acetaldehyde is liquid-liquid separated into an aqueous phase and an organic phase.

In the acetaldehyde-removing step, acetaldehyde derived from the process stream is removed from an object by a treatment, where the object is selected from at least a part of at least one of the aqueous phase and the organic phase, on the basis of a factor or factors selected from the group consisting of the liquid temperature in the liquid-liquid separation in the liquid-liquid separation step, the acetaldehyde concentration in at least one of the aqueous phase and the organic phase, the acetaldehyde partition coefficient, the methyl acetate concentration in at least one of the aqueous phase and the organic phase, and the methyl acetate partition coefficient.

In the recycling step, at least a part of at least one of the aqueous phase and the organic phase is recycled to the reactor.

In the crotonaldehyde-removing step, crotonaldehyde is removed from at least another part of at least one of the aqueous phase and the organic phase by a distillation treatment in a distillation column.

The separation step includes the substep of yielding, by separation using a first distillation column, a first acetic acid stream rich in acetic acid, and an overhead stream richer in light ends than the first acetic acid stream. In the substep, the crotonaldehyde concentration in the first acetic acid stream is controlled to 2.2 ppm by mass or less.

In the separation step, a reflux ratio at the first distillation column is controlled so that: the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed. In addition, the distillation column in the crotonaldehyde-removing step so as to meet at least one of conditions (a-i) to (a-iii) as follows:

(a-i) a reflux ratio at the distillation column is 0.01 or more;

(a-ii) at the distillation column, the ratio of a crotonaldehyde concentration (ppm by mass) in a distillate to a crotonaldehyde concentration (ppm by mass) in a charge liquid is less than 1; and (a-iii) at the distillation column, the ratio of a crotonaldehyde concentration (ppm by mass) in bottoms to a crotonaldehyde concentration (ppm by mass) in the charge liquid is greater than 1.

The second acetic acid production method according to the present invention includes a carbonylation step, a separation step, a liquid-liquid separation step, an acetaldehyde-removing step, a recycling step, and a crotonaldehyde-removing step.

In the carbonylation step, methanol is reacted (carbonylated) with carbon monoxide in a reactor in the presence of a catalytic system, acetic acid, methyl acetate, and water, to form acetic acid in a reaction mixture, where the catalytic system includes a metal catalyst and methyl iodide.

In the separation step, the reaction mixture from the carbonylation step is separated, using at least one selected from evaporators and distillation columns, into a stream including the metal catalyst, an acetic acid stream rich in acetic acid, and a stream richer in light ends than the acetic acid stream.

In the liquid-liquid separation step, a process stream including water, acetic acid, methyl iodide, and acetaldehyde is liquid-liquid separated into an aqueous phase and an organic phase.

In the acetaldehyde-removing step, acetaldehyde derived from the process stream is removed from an object by a treatment, where the object is selected from at least a part of at least one of the aqueous phase and the organic phase, and where the selection is performed on the basis of a factor or factors selected from the group consisting of the liquid temperature in the liquid-liquid separation in the liquid-liquid separation step, the acetaldehyde concentration in at least one of the aqueous phase and the organic phase, the acetaldehyde partition coefficient, the methyl acetate concentration in at least one of the aqueous phase and the organic phase, and the methyl acetate partition coefficient.

In the recycling step, at least a part of at least one of the aqueous phase and the organic phase is recycled to the reactor.

In the crotonaldehyde-removing step, at least another part of at least one of the aqueous phase and the organic phase is treated in a distillation column to remove crotonaldehyde therefrom.

The separation step includes the substep of yielding, by separation using a first distillation column, a first acetic acid stream rich in acetic acid, and a first overhead stream richer in light ends than the first acetic acid stream; and the substep of separating the first acetic acid stream, using a second distillation column, into a second overhead stream rich in water, and a second acetic acid stream richer in acetic acid than the first acetic acid stream.

In these substeps, a crotonaldehyde concentration in the first acetic acid stream is controlled to 2.2 ppm by mass or less, and/or a reflux ratio at the second distillation column is controlled to 0.1 or more.

In the separation step, a reflux ratio at the first distillation column is controlled so that: the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column. In addition, the distillation column in the crotonaldehyde-removing step so as to meet at least one of conditions (a-i) to (a-iii) as follows:

(a-i) a reflux ratio at the distillation column is 0.01 or more;

(a-ii) at the distillation column, the ratio of a crotonaldehyde concentration (ppm by mass) in a distillate to a crotonaldehyde concentration (ppm by mass) in a charge liquid is less than 1; and (a-iii) at the distillation column, the ratio of a crotonaldehyde concentration (ppm by mass) in bottoms to a crotonaldehyde concentration (ppm by mass) in the charge liquid is greater than 1.

The first and second acetic acid production methods according to the present invention are hereinafter also referred to as "acetic acid production methods according to the present invention". In the acetic acid production methods according to the present invention, the catalytic system may further include an ionic iodide. The ionic iodide functions as a promoter.

The separation step in the acetic acid production methods according to the present invention preferably includes, for example, an evaporation step, a light ends-removing step, and a dehydration step. In the evaporation step, the reaction mixture from the carbonylation step is separated, by evaporation in an evaporator, into a vapor stream and a residue stream (residual liquid stream). In the light ends-removing step, the vapor stream is subjected to distillation and thereby separated into a light ends-rich stream (such as an overhead stream, specifically, a first overhead stream), and a first acetic acid stream rich in acetic acid. In the dehydration step, the first acetic acid stream is subjected to distillation and thereby separated into a water-rich overhead stream (second overhead stream), and a second acetic acid stream richer in acetic acid than the first acetic acid stream. The distillation column for use in the light ends-removing step is also referred to as a first distillation column (light ends column), and the distillation column for use in the dehydration step is also referred to as a second distillation column (dehydration column).

Instead of the evaporation step and the light ends-removing step, the separation step may include an evaporation-light ends-removing step. This step is the step of separating the reaction mixture from the carbonylation step into the stream including the metal catalyst, the light ends-rich stream (for example, an overhead stream), and the first acetic acid stream rich in acetic acid. Instead of the light ends-removing step and the dehydration step, the separation step may include a so-called light ends-water-removing step. This step is a light ends-removing step that also functions as the dehydration step. Specifically, this step is the step of subjecting the vapor stream to distillation and separating the vapor stream into a light ends-rich stream (such as an overhead stream), and an acetic acid stream which has been dehydrated to a water concentration approximately equivalent to that in the second acetic acid stream. Accordingly, the evaporation-light ends-removing step may be an evaporation-light ends-water-removing step which also functions as the dehydration step. The acetic acid streams rich in acetic acid from the light ends-water-removing step and from the evaporation-light ends-water-removing step each correspond to the second acetic acid stream. The distillation columns for use in the evaporation-light ends-removing step, the light ends-water-removing step, and the evaporation-light ends-water-removing step each correspond to the first distillation column.

The separation step may include an evaporation step and a light ends-removing step. In the evaporation step, the reaction mixture from the carbonylation step is separated, by evaporation in an evaporator, into a vapor stream and a residue stream. In the light ends-removing step, the vapor stream is separated, using the first distillation column, into a first overhead stream rich in at least one light end selected from methyl iodide and acetaldehyde, and a first acetic acid stream rich in acetic acid; and the first overhead stream is subjected to condensation and liquid-liquid separation to give an aqueous phase and an organic phase.

The acetaldehyde-removing step is the step of removing acetaldehyde derived from the process stream by a treatment of an object, where the object is selected from at least a part of at least one of the aqueous phase and the organic phase, and where the selection is performed on the basis of a factor or factors selected from the group consisting of the liquid temperature in the liquid-liquid separation in the liquid-liquid separation step, the acetaldehyde concentration in at least one of the aqueous phase and the organic phase, the acetaldehyde partition coefficient, the methyl acetate concentration in at least one of the aqueous phase and the organic phase, and the methyl acetate partition coefficient.

As used herein, the term "process stream" refers to a liquid phase or a gas phase in a step of performing a process unit operation in the acetic acid production equipment, or in an apparatus or a facility with which the process unit operation is performed, where non-limiting examples of the process unit operation include reaction, evaporation, distillation, cooling, condensation, liquid-liquid separation, storage, and absorption. Non-limiting examples of the process stream include liquid phases and gas phases typically in pipes, reactor(s), evaporator(s), and distillation columns.

The acetaldehyde concentrations and the methyl acetate concentrations in the aqueous phase and the organic phase depend on the chemical composition of a liquid to be subjected to the liquid-liquid separation (hereinafter also referred to as a "liquid-liquid separation step feed liquid"), and the temperature in the liquid-liquid separation. With an increasing acetaldehyde concentration in the liquid-liquid separation step feed liquid, the acetaldehyde concentrations in the aqueous phase and the organic phase increase; and with an increasing methyl acetate concentration in the liquid-liquid separation step feed liquid, the methyl acetate concentrations in the aqueous phase and the organic phase increase. With an elevating temperature in the liquid-liquid separation, acetaldehyde is distributed in a larger proportion to the organic phase, as demonstrated in experimental examples mentioned later. The acetaldehyde concentration and the methyl acetate concentration in the liquid-liquid separation step feed liquid can be controlled typically by reaction conditions in the reactor, evaporation conditions in the evaporator, and distillation conditions in the distillation column(s). In general, the acetaldehyde concentration and the methyl acetate concentration in the liquid-liquid separation step feed liquid increase respectively with increasing acetaldehyde concentration and methyl acetate concentration in the reaction mixture. The acetaldehyde concentration in the reaction mixture tends to increase with each of increasing (elevating) reaction temperature, hydrogen partial pressure, methyl iodide concentration, water concentration, catalyst concentration, and lithium iodide concentration in the reaction system; and tends to decrease with each of increasing carbon monoxide (CO) partial pressure and methyl acetate concentration in the reaction system (see JP-A No. 2006-182691). The methyl acetate concentration in the reaction mixture increases with each of increasing acetic acid concentration and methanol concentration in the reaction system; and decreases with an increasing water concentration in the reaction system. This is because methyl acetate is formed as a result of esterification between acetic acid and methanol. Thus, regulation of reaction conditions in the reactor, and operation conditions in the evaporation step and the distillation step, which steps are performed prior to the liquid-liquid separation step, can adjust the chemical composition of the liquid-liquid separation step feed liquid, and consequently, can adjust the acetaldehyde concentrations and the methyl acetate concentrations in the aqueous phase and the organic phase. The inventor have found that, when the condensate is liquid-liquid separated, in a decanter at the light ends column, into an aqueous phase and an organic phase, the acetaldehyde partition coefficient has a certain correlation to the acetaldehyde concentration in the aqueous phase, the acetaldehyde concentration in the organic phase, the liquid temperature in the liquid-liquid separation, the methyl acetate concentration in the aqueous phase, and the methyl acetate concentration in the organic phase. As described above, the technique of subjecting the aqueous phase to an acetaldehyde-removing treatment, and the technique of subjecting the organic phase to an acetaldehyde-removing treatment each have advantages and disadvantages. Accordingly, it is industrially advantageous to employ the former technique when the acetaldehyde partition coefficient is at some high level (a relatively larger amount of acetaldehyde is distributed to the aqueous phase); to employ the latter technique when the acetaldehyde partition coefficient is at some low level (a relatively larger amount of acetaldehyde is distributed to the organic phase); and to employ both the two techniques when the acetaldehyde partition coefficient falls within an intermediate region between the two levels.

The methyl acetate concentration in the light ends column charge is controlled by adjusting the methyl acetate concentration in the reactor. For example, assume that methanol and carbon monoxide (CO) are charged into the reactor in constant amounts (at constant rates). In this case, the methyl acetate concentration in the reactor can be adjusted by increasing or decreasing one or more of factors that affect the reaction rate. Non-limiting examples of the factors include, each in the reactor, inside temperature, rhodium complex (Rh) quantity, methyl iodide (MeI) quantity, $H_2O$ quantity, hydrogen partial pressure, carbon monoxide partial pressure, and lithium iodide (LiI) quantity. Specifically, the methyl acetate concentration in the reactor is decreased by increasing one or more of the factors such as temperature, Rh quantity, MeI quantity, $H_2O$ quantity, hydrogen partial pressure, carbon monoxide partial pressure, and LiI quantity; and is increased by decreasing one or more of these factors. In contrast, assume that these conditions (factors) are set constant, namely, the conditions such as temperature, Rh quantity, MeI quantity, $H_2O$ quantity, hydrogen partial pressure, carbon monoxide partial pressure, and LiI quantity are set constant. In this case, the methyl acetate concentration is increased by increasing the charge amounts of methanol and CO; and is decreased by decreasing the charge amounts of them. The methyl acetate concentration in the vapor (light ends column charge) varies in proportion to the methyl acetate concentration in the liquid reaction mixture, where the vapor results from evaporation of the liquid reaction mixture by the working of the evaporator. This is because the evaporator is operated at a constant (predetermined) evaporation rate. When the evaporator is heated or cooled, the evaporation rate varies, and this causes the methyl acetate concentration to vary. For example, when the evaporator is heated, the acetic acid concentration increases, and the methyl acetate concentration decreases in the evaporator vapor. In contrast, when the evaporator is cooled, an inverse phenomenon occurs. Namely, the acetic acid concentration decreases, and the methyl acetate concentration increases in the evaporator vapor.

The recycling step may include an overhead stream recycling step of recycling, to the reactor, at least a part of at least one of an aqueous phase and an organic phase, and/or a part of the second overhead stream, where the aqueous phase and the organic phase result from condensation of the first overhead stream.

In an embodiment of the present invention, the crotonaldehyde concentration in the first acetic acid stream from the separation step is controlled to a low level of 2.2 ppm by mass or less. This configuration allows the second acetic acid stream, which results from separation and removal of water in the dehydration step, to have a lower crotonaldehyde concentration of typically 2.0 ppm by mass or less and to yield a better potassium permanganate test result. This can therefore downsize or eliminate acetaldehyde-removing facilities and ozone treatment facilities, which have been conventionally used for yielding better potassium permanganate test results. Such acetic acid yielding a good potassium permanganate test result can be obtained simply through the light ends column and the dehydration column. This can downsize or eliminate a downstream heavy ends column and a product column (finishing column). The crotonaldehyde concentration in the first acetic acid stream is preferably 2.0 ppm by mass or less, more preferably 1.8 ppm by mass or less, furthermore preferably 1.5 ppm by mass or less, particularly preferably 1.2 ppm by mass or less (for example, 1.0 ppm by mass or less, or 0.8 ppm by mass or less, and especially preferably 0.5 ppm by mass or less). Assume that the reflux ratio at the second distillation column (dehydration column) is controlled to 0.1 or more (in particular, 0.3 or more, for example, 0.32 or more). In this case, the crotonaldehyde concentration in the first acetic acid stream may be typically 5 ppm by mass or less (in particular, 2.5 ppm by mass or less), but preferably falls within the range.

A non-limiting example of the way to lower the crotonaldehyde concentration in the first acetic acid stream is increase in hydrogen partial pressure in the reactor. The increase in hydrogen partial pressure in the reactor causes crotonaldehyde to be hydrogenated, and thereby allows a liquid reaction mixture (liquid phase of the reaction mixture; a reaction medium) to have a lower crotonaldehyde concentration. This lowers the crotonaldehyde concentration in the liquid fed to the first distillation column, and, consequently, lowers the crotonaldehyde concentration in the first acetic acid stream resulting from removal of light ends by the working of the first distillation column. The hydrogen partial pressure in the reactor is typically 0.001 MPa (absolute pressure) or more (for example, 0.005 MPa or more), preferably 0.01 MPa (absolute pressure) or more (for example, 0.015 MPa or more), more preferably 0.02 MPa (absolute pressure) or more, furthermore preferably 0.04 MPa (absolute pressure) or more, and particularly preferably 0.06 MPa (absolute pressure) or more (for example, 0.07 MPa (absolute pressure) or more). The upper limit of the hydrogen partial pressure in the reactor is typically 0.5 MPa (absolute pressure) (in particular, 0.2 MPa (absolute pressure)).

In a preferred embodiment, the first acetic acid stream has a crotonaldehyde concentration of typically 1.3 ppm by mass or less, preferably 1.0 ppm by mass or less, more preferably 0.85 ppm by mass or less, and particularly preferably 0.5 ppm by mass or less (for example, 0.25 ppm by mass or less). Control of the crotonaldehyde concentration in the first acetic acid stream to 1.3 ppm by mass or less allows the second acetic acid stream to have a significantly lower crotonaldehyde concentration and to yield a significantly better potassium permanganate test result. The lower limit of the crotonaldehyde concentration in the first acetic acid stream may be 0 ppm by mass, or may typically be 0.01 ppm by mass (or 0.10 ppm by mass).

Another non-limiting example of the way to lower the crotonaldehyde concentration in the first acetic acid stream is increase in reflux ratio at the light ends column. With an increased reflux ratio at the light ends column, crotonaldehyde is more concentrated at the column top of the distillation column, because crotonaldehyde has a lower boiling point (104° C.) as compared with acetic acid (boiling point: 117° C.). This allows the first acetic acid stream, which is obtained as a side stream or a bottoms stream, to have a lower crotonaldehyde concentration. Assume that crotonaldehyde is concentrated in the first overhead stream by the increase in reflux ratio at the light ends column, and a condensate (at least one of an aqueous phase and an organic phase) derived from the first overhead stream is recycled to the reactor. In this case, the crotonaldehyde in the reactor reacts with acetaldehyde to form 2-ethylcrotonaldehyde. In addition, the crotonaldehyde in the reactor also reacts with hydrogen to form butyl alcohol, and the butyl alcohol in turn reacts with acetic acid to form butyl acetate. As compared with crotonaldehyde, 2-ethylcrotonaldehyde less affects the potassium permanganate test result, and butyl acetate does little or not affect the potassium permanganate test result. Thus, acetic acid tends to have still better quality. At a higher reflux ratio at the light ends column, 2-ethylcrotonaldehyde and butyl acetate tend to be concentrated in sidecuts from portions at height levels lower than the feeding level of the charge liquid to the light ends column, and in bottoms, because 2-ethylcrotonaldehyde and butyl acetate have boiling points respectively of 137° C. and 126° C., which are higher than the boiling point (117° C.) of acetic acid.

The reflux ratio at the light ends column is controlled as follows. Assume that the aqueous phase alone of the condensate derived from the first overhead stream is refluxed to the light ends column. In this case, the reflux ratio for the aqueous phase is controlled to typically 2 or more, preferably 3 or more, more preferably 4 or more, furthermore preferably 8 or more, and particularly preferably 10 or more, where the reflux ratio for the aqueous phase is the ratio of the aqueous phase reflux amount to the aqueous phase distillate amount. Assume that the organic phase alone of the condensate derived from the first overhead stream is refluxed to the light ends column. In this case, the reflux ratio for the organic phase is contorted to typically 1 or more, preferably 1.5 or more, more preferably 2 or more, furthermore preferably 4 or more, and particularly preferably 5 or more, where the reflux ratio for the organic phase is the ratio of the organic phase reflux amount to the organic phase distillate amount. Assume that both the aqueous phase and the organic phase of the condensate derived from the first overhead stream are refluxed to the light ends column. In this case, the total reflux ratio for the aqueous phase and the organic phase is controlled to typically 1.5 or more, preferably 2.3 or more, more preferably 3 or more, furthermore preferably 6 or more, and particularly preferably 7.5 or more, where the total reflux ratio is the ratio of the totality of the reflux amounts of the aqueous phase and the organic phase to the totality of the distillate amounts of the aqueous phase and the organic phase. When the aqueous phase is refluxed to the light ends column, the reflux ratio for the aqueous phase is preferably 2 or more, more preferably 3 or more, furthermore preferably 5 or more, particularly preferably 8 or more, and especially preferably 12 or more, where the reflux ratio for the aqueous phase is the ratio of the aqueous phase reflux amount to the aqueous phase distillate amount. When the reflux ratio at the dehydration column is controlled to 0.1 or more (in particular, 0.3 or more, for example, 0.32 or more) as described above, the reflux ratio at the light ends column may be typically 0.5 or more, regardless of whichever of the upper phase and the lower phase is refluxed. In any case, the upper limit of the reflux ratio at the light ends column may be typically 3000 (in particular, 1000), or may be 100 (in particular, 30).

Still another non-limiting example of the way to lower the crotonaldehyde concentration in the first acetic acid stream is decrease in concentration of acetaldehyde present in the liquid reaction mixture (reaction medium) in the reactor. The decrease in acetaldehyde concentration in the liquid reaction mixture in the reactor restrains the formation of crotonaldehyde, where crotonaldehyde will be formed by aldol condensation of acetaldehyde. This allows the liquid to be fed to the first distillation column to have a lower crotonaldehyde concentration, and, consequently, allows the first acetic acid stream to also have a lower crotonaldehyde concentration, where the first acetic acid stream results from the removal of light ends in the first distillation column. The acetaldehyde concentration in the liquid reaction mixture in the reactor is typically 500 ppm by mass or less, preferably 450 ppm by mass or less, more preferably 400 ppm by mass or less, furthermore preferably 350 ppm by mass or less, and particularly preferably 300 ppm by mass or less (for example, 250 ppm by mass or less). The acetaldehyde concentration in the liquid reaction mixture in the reactor can be lowered typically by increasing the carbon monoxide (CO) partial pressure in the reactor, and/or by increasing the methyl acetate concentration in the liquid reaction mixture in the reactor. The acetaldehyde concentration in the liquid reaction mixture in the reactor can be lowered typically by increasing the feeding amount to the acetaldehyde-removing step and decreasing the recycling amount to the reactor, of the condensate (at least one of the aqueous phase and the organic phase) derived from the first overhead liquid from the first distillation column.

The acetic acid production methods according to the present invention may include a dehydration step in which the first acetic acid stream is separated, using a second distillation column, into a second overhead stream rich in water, and a second acetic acid stream richer in acetic acid than the first acetic acid stream. The dehydration of the first acetic acid stream in the second distillation column can give a second acetic acid stream that has a low water content, as bottoms or a sidecut liquid respectively from the column bottom or an intermediate height level in the column. The second acetic acid stream can serve as an acetic acid product without, or with further purification as needed.

The reflux ratio at the second distillation column is typically 0.1 or more (in particular, 0.3 or more, typically 0.32 or more), preferably 1.0 or more, more preferably 5.0 or more, and furthermore preferably 10 or more (for example, 12 or more). The upper limit of the reflux ratio at the second distillation column may be typically about 3000 (or about 1000), or about 200 (or about 100). Increase in reflux ratio at the second distillation column to 0.1 or more (in particular, 0.3 or more, for example 0.32 or more) allows the second acetic acid stream to have a higher purity and to yield a better potassium permanganate test result.

Control of the reflux ratio at the dehydration column to 0.1 or more (in particular, 0.3 or more, and preferably 0.32 or more) allows crotonaldehyde flowing into the dehydration column to be concentrated at the column top, because crotonaldehyde has a lower boiling point as compared with acetic acid. This allows the second acetic acid stream to have a significantly lower crotonaldehyde concentration, where the second acetic acid stream is obtained as a side stream or bottoms stream from the dehydration column. In addition, when the second overhead stream from the column top of the dehydration column, at which crotonaldehyde is concentrated, is recycled to the reactor, crotonaldehyde is converted into less harmful 2-ethylcrotonaldehyde and harmless butyl acetate. This contributes to still better quality of acetic acid.

In a preferred embodiment, the reflux ratio at the dehydration column is 0.1 or more (in particular, 0.3 or more, for example, 0.32 or more), preferably 0.4 or more, more preferably 1 or more, and furthermore preferably 2 or more. When the crotonaldehyde concentration in the first acetic acid stream is controlled to 2.2 ppm by mass or less, the reflux ratio at the dehydration column may be typically 0.1 or more (for example, 0.2 or more, and in particular, 0.3 or more, for example, 0.32 or more). The upper limit of the reflux ratio at the dehydration column is typically 3000 (in particular, 1000), and may be about 100 or about 10. Increase in reflux ratio at the dehydration column to 0.1 or more (in particular, 0.3 or more, and preferably 0.32 or more) allows the second acetic acid stream to have a higher purity and to yield a better potassium permanganate test result.

According to the present invention, the reflux ratio at the first distillation column is increased to cause crotonaldehyde to be concentrated at the column top, and at least a part of at least one of the aqueous phase and the organic phase of the light ends column overhead condensate, in which crotonaldehyde is concentrated, is recycled to the reactor. The concentrating (enrichment) of crotonaldehyde at the column top allows the first acetic acid stream to have a lower crotonaldehyde concentration, and this gives an acetic acid product yielding a good potassium permanganate test result. Crotonaldehyde recycled to the reactor is converted into 2-ethylcrotonaldehyde and/or converted into butyl acetate by the reactions: crotonaldehyde+acetaldehyde→2-ethylcrotonaldehyde, crotonaldehyde+hydrogen→butyl alcohol, butyl alcohol+acetic acid→butyl acetate, where 2-ethylcrotonaldehyde less affects the potassium permanganate test result, and butyl acetate does not approximately affect the potassium permanganate test result, as compared with crotonaldehyde. Thus, the acetic acid product can have better quality. Also according to the present invention, at least another part of at least one of the aqueous phase and the organic phase is treated in the crotonaldehyde-removing column, where the aqueous phase and the organic phase are derived from the light ends column overhead condensate, in which crotonaldehyde is concentrated. In this process, the acetic acid product is allowed to yield a still better potassium permanganate test result, by drawing crotonaldehyde, which has a high boiling point of 104° C., as bottoms as high-boiling compounds together with acetic acid and alkanes, and discharging them out of the system. The overhead condensate from the crotonaldehyde-removing column includes useful components (such as methyl iodide and methyl acetate) and can be recycled to the reactor and/or the decanter in which the light ends column overhead condensate is stored.

The reflux ratio at the first distillation column is controlled as follows. When the aqueous phase alone is refluxed to the first distillation column, the reflux ratio for the aqueous phase is 2 or more, preferably 3 or more, more preferably 5 or more, furthermore preferably 8 or more, and particularly preferably 12 or more, where the reflux ratio for the aqueous phase is the ratio of the aqueous phase reflux amount to the aqueous phase distillate amount. When the organic phase alone is refluxed to the first distillation column, the reflux ratio for the organic phase is 1 or more, preferably 1.5 or more, more preferably 2 or more, furthermore preferably 4 or more, and particularly preferably 5 or more, where the reflux ratio for the organic phase is the ratio of the organic phase reflux amount to the organic phase distillate amount. When both the aqueous phase and the organic phase are refluxed to the first distillation column, the total reflux ratio for the aqueous phase and the organic phase is 1.5 or more, preferably 2.3 or more, more preferably 3.5 or more, furthermore preferably 6 or more, and particularly preferably 8.5 or more, where the total reflux ratio is the ratio of the totality of the reflux amounts of the aqueous phase and the organic phase to the totality of the distillate amounts of the aqueous phase and the organic phase. When the aqueous phase is refluxed to the first distillation column, the reflux ratio for the aqueous phase is preferably 2 or more, more preferably 3 or more, furthermore preferably 5 or more, particularly preferably 8 or more, and especially preferably 12 or more, where the reflux ratio for the aqueous phase is the ratio of the aqueous phase reflux amount to the aqueous phase distillate amount. In any case, the upper limit of the reflux ratio at the first distillation column may be typically 3000 (in particular, 1000), or may be 100 (in particular, 30).

Relating to the condition (a-i), the reflux ratio at the crotonaldehyde-removing column is preferably 0.05 or more, more preferably 0.5 or more, furthermore preferably 5 or more, and particularly preferably 20 or more (for example, 30 or more). The upper limit of the reflux ratio at the crotonaldehyde-removing column is typically 1000. Relating to the condition (a-ii), at the crotonaldehyde-removing column, the ratio of the crotonaldehyde concentration (ppm by mass) in the distillate to the crotonaldehyde concentration (ppm by mass) in the charge liquid is preferably 0.95 or less, more preferably 0.80 or less, furthermore preferably 0.70 or less, and particularly preferably 0.60 or less (for example, 0.50 or less, especially preferably 0.30 or less, and particularly preferably 0.20 or less). Relating to the condition (a-iii), at the crotonaldehyde-removing column, the ratio of the crotonaldehyde concentration (ppm by mass) in the bottoms to the crotonaldehyde concentration (ppm by mass) in the charge liquid is preferably 1.2 or more, more preferably 1.5 or more, furthermore preferably 2.0 or more, particularly preferably 3.0 or more (for example, 4.0 or more, and especially preferably 5.0 or more), and especially preferably 10 or more (for example, 20 or more). Operation of the crotonaldehyde-removing column so as to meet at least one of the conditions (a-i) to (a-iii) causes crotonaldehyde to be concentrated at the column bottom and to be discharged out of the system, as bottoms also including alkanes and other high-boiling impurities, and acetic acid.

As used herein, the term "reflux ratio" at a distillation column refers to the "ratio of the reflux amount to the distillate amount", where the term "reflux amount" refers to the amount of a liquid, out of overhead liquids from the distillation column, to be returned to the distillation column; and the term "distillate amount" refers to the amount of a liquid, out of the overhead liquids from the distillation column, not to be returned to the distillation column, but to be discharged out of the distillation column.

In the present invention, a phase to be subjected to the acetaldehyde-removing step is determined or selected as follows. Specifically, a process stream including water, acetic acid (AC), methyl iodide (MeI), and acetaldehyde (AD) is liquid-liquid separated into an aqueous phase and an organic phase in the liquid-liquid separation step (such as liquid-liquid separation in a decanter 4); and herein, the phase to be subjected to the acetaldehyde-removing step is determined on the basis of a factor or factors selected from the acetaldehyde concentration in the aqueous phase, the acetaldehyde concentration in the organic phase, the methyl acetate concentration in the aqueous phase, the methyl acetate concentration in the organic phase, the totality of the methyl acetate concentration in the aqueous phase and the methyl acetate concentration in the organic phase, the temperature (liquid temperature) in the liquid-liquid separation, the acetaldehyde partition coefficient (AD partition coefficient) determined according to an equation mentioned later, and the methyl acetate partition coefficient (MA partition coefficient) determined according to an equation mentioned later. In another aspect, there are given preferred liquid-liquid separation conditions when the organic phase is subjected to the acetaldehyde-removing step, and preferred liquid-liquid separation conditions when the aqueous phase is subjected to the acetaldehyde-removing step. The equations are expressed as follows:

AD partition coefficient={AD concentration (mass percent) in aqueous phase}/{AD concentration (mass percent) in organic phase}

MA partition coefficient={MA concentration (mass percent) in aqueous phase}/{MA concentration (mass percent) in organic phase}

In an embodiment of the acetic acid production methods according to the present invention, the liquid-liquid separation step meets at least one of conditions (b-i) to (b-v), and at least a part of the aqueous phase is subjected to the treatment in the acetaldehyde-removing step, where the conditions (b-i) to (b-v) are expressed as follows:

(b-i) the aqueous phase has an acetaldehyde concentration of 28.1 mass percent or less, and/or the organic phase has an acetaldehyde concentration of 24.8 mass percent or less;

(b-ii) the liquid-liquid separation is performed at a temperature of 70° C. or lower;

(b-iii) the aqueous phase has a methyl acetate concentration of 12.0 mass percent or less, and/or the organic phase has a methyl acetate concentration of 47.6 mass percent or less, and/or the totality of the methyl acetate concentration in the aqueous phase and the methyl acetate concentration in the organic phase is 59.6 mass percent or less;

(b-iv) an acetaldehyde partition coefficient is 1.1 or more, where the acetaldehyde partition coefficient is the ratio of the acetaldehyde concentration (mass percent) in the aqueous phase to the acetaldehyde concentration (mass percent) in the organic phase; and (b-v) a methyl acetate partition coefficient is 0.25 or more, where the methyl acetate partition coefficient is the ratio of the methyl acetate concentration (mass percent) in the aqueous phase to the methyl acetate concentration (mass percent) in the organic phase.

Relating to the condition (b-i), the acetaldehyde concentration in the aqueous phase is typically 0.045 to 28.1 mass percent, preferably 0.098 to 10 mass percent, furthermore preferably 0.098 to 3.0 mass percent, and particularly preferably 0.098 to 1.0 mass percent (for example, 0.15 to 0.9 mass percent); whereas the acetaldehyde concentration in the organic phase is typically 0.013 to 24.8 mass percent, preferably 0.030 to 2.0 mass percent, furthermore preferably 0.030 to 0.50 mass percent, and particularly preferably 0.030 to 0.24 mass percent. Relating to the condition (b-i), it is preferred that the aqueous phase has an acetaldehyde concentration of 28.1 mass percent or less, and the organic phase has an acetaldehyde concentration of 24.8 mass percent or less. When the condition (b-i) is met, the liquid-liquid separation step feed liquid (such as the liquid to be fed to the decanter 4) has an acetaldehyde concentration of typically 26.0 mass percent or less (for example, 0.026 to 26.0 mass percent), preferably 0.057 to 10 mass percent, furthermore preferably 0.057 to 3.0 mass percent, and particularly preferably 0.057 to 1.0 mass percent (for example, 0.057 to 0.42 mass percent). If the aqueous phase has an acetaldehyde concentration of greater than 28.1 mass percent, and the organic phase has an acetaldehyde concentration of greater than 24.8 mass percent, the AD partition coefficient decreases (for example, decreases to less than 1.1). This leads to very small advantages of the treatment of the aqueous phase in the acetaldehyde-removing step, in comparison and consideration between the acetaldehyde recovery amount and the need for the use of equipment that has very high corrosion resistance and is therefore expensive.

Relating to the condition (b-ii), the temperature (liquid temperature) in the liquid-liquid separation is typically −5° C. to 70° C., preferably −5° C. to 60° C., more preferably −5° C. to 51° C. (for example, −5° C. to 45° C.), and furthermore preferably −5° C. to 41° C. (for example, −5° C. to 31° C.). The liquid-liquid separation, if performed at a temperature (liquid temperature) of higher than 70° C., causes the AD partition coefficient to be very low, and this leads to very small advantages of the treatment of the aqueous phase in the acetaldehyde-removing step.

Relating to the condition (b-iii), the methyl acetate concentration in the aqueous phase is typically 1.2 to 12.0 mass percent, preferably 2.0 to 12.0 mass percent, and furthermore preferably 5.0 to 12.0 mass percent (for example, 6.0 to 12.0 mass percent); whereas the methyl acetate concentration in the organic phase is typically 2.2 to 47.6 mass percent, preferably 5.0 to 42 mass percent, and furthermore preferably 8.0 to 35 mass percent (for example, 10.0 to 30 mass percent). Relating to the condition (b-iii), it is preferred that the aqueous phase has a methyl acetate concentration of 12.0 mass percent or less, and the organic phase has a methyl acetate concentration of 47.6 mass percent or less. The totality of the methyl acetate concentration (mass percent) in the aqueous phase and the methyl acetate concentration (mass percent) in the organic phase is typically 59.6 mass percent or less (for example, 4.2 to 59.6 mass percent), preferably 6.0 to 54 mass percent, more preferably 8.0 to 54 mass percent, furthermore preferably 10.0 to 54 mass percent, and particularly preferably 14.0 to 47 mass percent (for example, 16.0 to 42 mass percent). When the condition (b-iii) is met, the liquid-liquid separation step feed liquid (such as the liquid to be fed to the decanter 4) has a methyl acetate concentration of typically 38.2 mass percent or less (for example, 2.0 to 38.2 mass percent), preferably 5.0 to 31 mass percent, more preferably 8.0 to 25 mass percent, and furthermore preferably 10.0 to 25 mass percent). If the aqueous phase has a methyl acetate concentration of greater than 12.0 mass percent, the organic phase has a methyl acetate concentration of greater than 47.6 mass percent, and the totality of the methyl acetate concentration (mass percent) in the aqueous phase and the methyl acetate concentration (mass percent) in the organic phase is greater than 59.6 mass percent, the AD partition coefficient is typically less than 1.1. This leads to very small advantages of the treatment of the aqueous phase in the acetaldehyde-removing step, for reasons as above.

Relating to the condition (b-iv), the AD partition coefficient is typically 1.1 to 8.0, preferably 1.5 to 6.0, and furthermore preferably 1.9 to 5.0. If the AD partition coefficient is less than 1.1, the aqueous phase has a low acetaldehyde concentration. This causes the acetaldehyde-removing treatment of the aqueous phase to be industrially very disadvantageous, because the treatment requires much energy and often causes corrosion of the equipment. In contrast, when the AD partition coefficient is 1.1 or more (preferably 1.5 or more, and furthermore preferably 1.9 or more), the acetaldehyde-removing treatment of the aqueous phase has large advantages for higher acetaldehyde removal efficiency, even upon the use of equipment that has high corrosion resistance.

Relating to the condition (b-v), the MA partition coefficient is 0.25 or more (for example, 0.25 to 0.70), preferably 0.26 or more (for example, 0.26 to 0.65), and furthermore preferably 0.28 or more (for example, 0.28 to 0.60). As described above, the methyl acetate (MA) distribution ratio (partition coefficient) between the aqueous phase and the organic phase varies depending on the temperature and the chemical compositions (including not only water and methyl iodide, but also acetic acid and other components), and can therefore also serve as an index for the control of the acetaldehyde partition coefficient.

In the acetic acid production methods according to the embodiment of the present invention, the liquid-liquid separation step has only to meet at least one of the conditions (b-i) to (b-v), but may meet two or more of the conditions together.

In another embodiment of the acetic acid production methods according to the present invention, the liquid-liquid separation step meets at least one of conditions (b'-i) to (b'-v), and at least a part of the organic phase is subjected to the treatment in the acetaldehyde-removing step, where the conditions (b'-i) to (b'-v) are expressed as follows:

(b'-i) the aqueous phase has an acetaldehyde concentration of 0.045 mass percent or more, and/or the organic phase has an acetaldehyde concentration of 0.013 mass percent or more;

(b'-ii) the liquid-liquid separation is performed at a temperature of −5° C. or higher;

(b'-iii) the aqueous phase has a methyl acetate concentration of 1.2 mass percent or more, and/or the organic phase has a methyl acetate concentration of 2.2 mass percent or more, and/or the totality of the methyl acetate concentration in the aqueous phase and the methyl acetate concentration in the organic phase is 3.4 mass percent or more;

(b'-iv) the acetaldehyde partition coefficient is 4.1 or less, where the acetaldehyde partition coefficient is the ratio of the acetaldehyde concentration (mass percent) in the aqueous phase to the acetaldehyde concentration (mass percent) in the organic phase; and (b'-v) the methyl acetate partition coefficient is 0.8 or less, where the methyl acetate partition coefficient is the ratio of the methyl acetate concentration (mass percent) in the aqueous phase to the methyl acetate concentration (mass percent) in the organic phase.

Relating to the condition (b'-i), the acetaldehyde concentration in the aqueous phase is typically 0.045 to 35 mass percent, preferably 0.15 to 10 mass percent, and furthermore preferably 0.2 to 2.0 mass percent; whereas the acetaldehyde concentration in the organic phase is typically 0.013 to 30 mass percent, preferably 0.05 to 5.0 mass percent, and furthermore preferably 0.1 to 1.0 mass percent. Relating to the condition (b'-i), it is preferred that the aqueous phase has an acetaldehyde concentration of 0.045 mass percent or more, and the organic phase has an acetaldehyde concentration of 0.013 mass percent or more. When the condition (b'-i) is met, the liquid-liquid separation step feed liquid (such as the liquid to be fed to the decanter 4) has an acetaldehyde concentration of typically 0.026 mass percent or more (for example, 0.026 to 32 mass percent), preferably 0.10 to 8.0 mass percent, and furthermore preferably 0.15 to 1.8 mass percent. If the aqueous phase has an acetaldehyde concentration of less than 0.045 mass percent, and the organic phase has an acetaldehyde concentration of less than 0.013 mass percent, the AD partition coefficient is high. This leads to very small advantages of the treatment of the organic phase in the acetaldehyde-removing step.

Relating to the condition (b'-ii), the temperature (liquid temperature) in the liquid-liquid separation is −5° C. or higher (for example, −5° C. to 90° C.), preferably 0° C. or higher (for example, 0° C. to 90° C.), more preferably 10° C. or higher (for example, 10° C. to 90° C.), furthermore preferably 20° C. or higher (for example, 25° C. to 90° C.), a temperature higher than 30° C. (for example, from higher than 30° C. to 90° C.)), a temperature higher than 35° C. (for example, from higher than 35° C. to 90° C.), a temperature higher than 40° C. (for example, from higher than 40° C. to 90° C.), and particularly preferably a temperature higher than 70° C. (for example, from higher than 70° C. to 90° C.). The liquid-liquid separation, if performed at a temperature (liquid temperature) lower than −5° C., causes the AD partition coefficient to be typically greater than 4.3. This leads to very small advantages of the treatment of the organic phase in the acetaldehyde-removing step.

Relating to the condition (b'-iii), the methyl acetate concentration in the aqueous phase is typically 1.2 to 20 mass percent, preferably 2.5 to 18 mass percent, more preferably 4.0 to 15 mass percent, furthermore preferably 6.0 to 13 mass percent, and particularly preferably 7.0 to 12 mass percent; whereas the methyl acetate concentration in the organic phase is typically 2.2 to 60 mass percent, preferably 5.8 to 48 mass percent, more preferably 8.0 to 40 mass percent, furthermore preferably 10.0 to 30 mass percent, and particularly preferably 11.0 to 25 mass percent. Relating to the condition (b'-iii), it is preferred that the aqueous phase has a methyl acetate concentration of 1.2 mass percent or more, and the organic phase has a methyl acetate concentration of 2.2 mass percent or more. The totality of the methyl acetate concentration (mass percent) in the aqueous phase and the methyl acetate concentration (mass percent) in the organic phase is typically 3.4 to 75 mass percent, preferably 8.3 to 60 mass percent (for example, 10 to 40 mass percent), more preferably 15.0 to 50 mass percent, and furthermore preferably 25 to 53 mass percent. When the condition (b'-iii) is met, the liquid-liquid separation step feed liquid (such as the liquid to be fed to the decanter 4) has a methyl acetate concentration of typically 2.0 to 50 mass percent, preferably 5.0 to 38 mass percent, more preferably 8.0 to 35 mass percent, and furthermore preferably 10.0 to 32 mass percent. If the aqueous phase has a methyl acetate concentration of less than 1.2 mass percent, the organic phase has a methyl acetate concentration of less than 2.2 mass percent, and the totality of the methyl acetate concentration (mass percent) in the aqueous phase and the methyl acetate concentration (mass percent) in the organic phase is less than 3.4 mass percent, the AD partition coefficient is high. This lead to small advantages of the treatment of the organic phase in the acetaldehyde-removing step.

Relating to the condition (b'-iv), the AD partition coefficient is 4.1 or less (for example, 0.5 to 4.1), preferably 3.35 or less (for example, 0.6 to 3.35), more preferably 3 or less (0.7 to 3), furthermore preferably 2.8 or less (for example, 0.8 to 2.8), and particularly preferably 2.5 or less (for example, 0.8 to 2.5), especially preferably 2.3 or less (for example, 0.9 to 2.3), and still especially preferably 2.0 or less (for example, 1.0 to 2.0). If the AD partition coefficient is greater than 4.1, the organic phase has a very low acetaldehyde concentration. This leads to very small advantages of the treatment of the organic phase in the acetaldehyde-removing step. Non-limiting examples of the way to control the AD partition coefficient to a level (less than 1.1) most preferred for the acetaldehyde-removing treatment of the organic phase include control of the acetaldehyde concentration in the aqueous phase to greater than 28.1 mass percent; control of the acetaldehyde concentration in the organic phase to greater than 24.8 mass percent; control of the acetaldehyde concentration in the liquid-liquid separation step feed liquid to greater than 26.0 mass percent; control of the temperature in the liquid-liquid separation to higher than 70° C.; control of the methyl acetate concentration in the aqueous phase to greater than 12.0 mass percent; control of the methyl acetate concentration in the organic phase to greater than 47.6 mass percent; and control of the methyl acetate concentration in the liquid-liquid separation step feed liquid to greater than 38.2 mass percent.

Relating to the condition (b'-v), the MA partition coefficient is 0.8 or less (for example, 0.15 to 0.80), preferably 0.7 or less (for example, 0.20 to 0.70), more preferably 0.6 or less (for example, 0.20 to 0.60), furthermore preferably 0.44 or less (for example, 0.20 to 0.44), and particularly preferably less than 0.25 (for example, from 0.20 to less than 0.25). The methyl acetate (MA) distribution ratio (partition coefficient) between the aqueous phase and the organic phase varies depending on the temperature and the chemical compositions (including not only water and methyl iodide, but also acetic acid and other components), and can therefore also serve as an index for control of the acetaldehyde partition coefficient.

In the acetic acid production methods according to the embodiment of the present invention, the liquid-liquid separation step has only to meet at least one of the conditions (b'-i) to (b'-v), but may meet two or more of the conditions together.

In the present invention, the second acetic acid stream has a crotonaldehyde concentration of typically 2.0 ppm by mass or less, preferably 1.8 ppm by mass or less, more preferably 1.5 ppm by mass or less, furthermore preferably 1.2 ppm by mass or less, and particularly preferably 0.7 ppm by mass or less (for example, 0.5 ppm by mass or less).

In a preferred embodiment, the second acetic acid stream has a crotonaldehyde concentration of typically 0.98 ppm by mass or less, preferably 0.80 ppm by mass or less, more preferably 0.50 ppm by mass or less, and furthermore preferably 0.30 ppm by mass or less. The second acetic acid stream, if controlled to have a crotonaldehyde concentration of 0.98 ppm by mass or less, can have a significantly lower crotonaldehyde concentration and can yield a significantly better potassium permanganate test result. The lower limit of the crotonaldehyde concentration in the second acetic acid stream may be 0 ppm by mass, or may also be typically 0.01 ppm by mass (or 0.10 ppm by mass).

The second acetic acid stream has an 2-ethylcrotonaldehyde concentration of typically 3.0 ppm by mass or less, preferably 2.0 ppm by mass or less, more preferably 1.0 ppm by mass or less, and furthermore preferably 0.8 ppm by mass or less (for example, 0.5 ppm by mass or less).

In a preferred embodiment, the second acetic acid stream has an 2-ethylcrotonaldehyde concentration of typically 1.00 ppm by mass or less, preferably 0.50 ppm by mass or less, more preferably 0.30 ppm by mass or less, and furthermore preferably 0.20 ppm by mass or less. The second acetic acid stream, when controlled to have an 2-ethylcrotonaldehyde concentration of 1.0 ppm by mass or less, can yield a still better potassium permanganate test result. The lower limit of the 2-ethylcrotonaldehyde concentration in the second acetic acid stream may be typically 0 ppm by mass, or 0.01 ppm by mass (for example, 0.10 ppm by mass).

The second acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less, preferably 35 or less, more preferably 25 or less, furthermore preferably 20 or less, and particularly preferably 15 or less. The lower limit of the ratio may be typically 0.5, 0.3, 0.1, 0.05, or 0.01. In the present invention, the ratio ($C_{CR}/C_{ECR}$) of the crotonaldehyde concentration $C_{CR}$ (ppm by mass) to the 2-ethylcrotonaldehyde concentration $C_{ECR}$ (ppm by mass) in the second acetic acid stream may be regulated by controlling both the crotonaldehyde concentration and the 2-ethylcrotonaldehyde concentration in the second acetic acid stream. Specifically, it is acceptable that, by efficient separation in the separation step using the difference in boiling point from acetic acid, crotonaldehyde is concentrated in the overhead condensate from the dehydration column (second distillation column), and thereby the crotonaldehyde concentration is lowered and the 2-ethylcrotonaldehyde concentration is regulated in the second acetic acid stream, where the second acetic acid stream is obtained as a side stream or bottoms stream from the dehydration column. Thus, both the crotonaldehyde concentration and the 2-ethylcrotonaldehyde concentration in the second acetic acid stream can be controlled together.

The second acetic acid stream has a butyl acetate concentration of typically 15 ppm by mass or less, preferably 12 ppm by mass or less, more preferably 10 ppm by mass or less, and furthermore preferably 8 ppm by mass or less.

In a preferred embodiment, the second acetic acid stream has a butyl acetate concentration of typically 15 ppm by mass or less, preferably 10 ppm by mass or less, more preferably 8 ppm by mass or less, and particularly preferably 5 ppm by mass or less (for example, 3 ppm by mass or less). The second acetic acid stream, when controlled to have a butyl acetate concentration of 15 ppm by mass or less, can have higher quality. The lower limit of the butyl acetate concentration in the second acetic acid stream may be typically 0 ppm by mass, or 0.1 ppm by mass (for example, 0.3 ppm by mass or 1.0 ppm by mass).

The second acetic acid stream has a ratio ($C_{CR}/C_{BA}$) of the crotonaldehyde concentration $C_{CR}$ (ppm by mass) to the butyl acetate concentration $C_{BA}$ (ppm by mass) of typically 2.0 or less, preferably 1.5 or less, more preferably 1.0 or less, and furthermore preferably 0.6 or less. The lower limit of the ratio may be typically 0.1, 0.05, 0.02, 0.01, or 0.001.

The second acetic acid stream yields a potassium permanganate test result of preferably longer than 50 minutes, more preferably 60 minutes or longer, furthermore preferably 100 minutes or longer, and particularly preferably 120 minutes or longer (for example, 180 minutes or longer, especially preferably 240 minutes or longer, and particularly preferably 360 minutes or longer). The potassium permanganate test result is prescribed also in Japanese Industrial Standards (JIS) as one of indices for quality control of acetic acid products. Thus, the potassium permanganate test result can be said as a preferred index that is industrially widely used for quality control of acetic acid products and enables easy examination of the quality of such acetic acid products. Measurements in the potassium permanganate test can be performed according to the procedure for visual colorimetry prescribed in JIS K 1351:1993.

The acetic acid production methods according to the present invention each include an acetaldehyde-removing step of subjecting at least a part of at least one of the aqueous phase and the organic phase to distillation to remove acetaldehyde therefrom, where the aqueous phase and the organic phase results from condensation of the first overhead stream. After the removal of acetaldehyde from at least a part of at least one of the aqueous phase and the organic phase, at least a part of the resulting residue may be recycled to the reactor. The presence of the acetaldehyde-removing step enables efficient removal of acetaldehyde formed in the reaction system. The recycling of the residue remained after the acetaldehyde removal to the reactor enables effective use of useful components such as methyl iodide.

The vapor stream to be fed to the first distillation column has a crotonaldehyde concentration of typically 0 to 5.0 ppm by mass (for example, 0.01 to 4.0 ppm by mass), preferably 0.1 to 3.0 ppm by mass, and furthermore preferably 0.2 to 2.0 ppm by mass. The vapor stream has an 2-ethylcrotonaldehyde concentration of typically 0 to 3.0 ppm by mass (for example, 0.01 to 2.5 ppm by mass), preferably 0.02 to 2.0 ppm by mass, and furthermore preferably 0.03 to 0.8 ppm by mass. The vapor stream has a butyl acetate concentration of typically 0.1 to 13.0 ppm by mass, preferably 0.2 to 12.0 ppm by mass, and furthermore preferably 0.3 to 9.0 ppm by mass.

In a preferred embodiment, the first acetic acid stream has a crotonaldehyde concentration of typically 1.3 ppm by mass or less, preferably 1.0 ppm by mass or less, more preferably 0.85 ppm by mass or less, and particularly preferably 0.5 ppm by mass or less (for example, 0.25 ppm by mass or less). Control of the crotonaldehyde concentration in the first acetic acid stream to 1.3 ppm by mass or less allows the second acetic acid stream to have a significantly lower crotonaldehyde concentration and to yield a significantly better potassium permanganate test result. The lower limit of the crotonaldehyde concentration in the first acetic acid stream may be 0 ppm by mass, but may be typically 0.01 ppm by mass (or 0.10 ppm by mass).

In the present invention, the first acetic acid stream has an 2-ethylcrotonaldehyde concentration of typically 3.0 ppm by mass or less, preferably 2.0 ppm by mass or less, more preferably 1.0 ppm by mass or less, and furthermore preferably 0.8 ppm by mass or less (for example, 0.5 ppm by mass or less).

In a preferred embodiment, the first acetic acid stream has an 2-ethylcrotonaldehyde concentration of typically 1.0 ppm by mass or less, and preferably 0.50 ppm by mass or less. Control of the 2-ethylcrotonaldehyde concentration in the first acetic acid stream to 1.0 ppm by mass or less allows the second acetic acid stream to yield a still better potassium permanganate test result. The lower limit of the 2-ethylcrotonaldehyde concentration in the first acetic acid stream may be typically 0 ppm by mass, or 0.01 ppm by mass (or 0.10 ppm by mass).

The first acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less, preferably 35 or less, more preferably 25 or less, furthermore preferably 20 or less, and particularly preferably 15 or less. The lower limit of the ratio may be typically 0.5, 0.3, 0.1, 0.05, or 0.01. In the present invention, it is acceptable that both the crotonaldehyde concentration and the 2-ethylcrotonaldehyde concentration in the first acetic acid stream are controlled together to regulate the ratio ($C_{CR}/C_{ECR}$) of the crotonaldehyde concentration $C_{CR}$ (ppm by mass) to the 2-ethylcrotonaldehyde concentration $C_{ECR}$ (ppm by mass). Specifically, it is acceptable that, by efficient separation in the separation step using the difference in boiling point from acetic acid, crotonaldehyde is concentrated in the overhead condensate from the light ends column (first distillation column); and thereby the crotonaldehyde concentration is lowered and the 2-ethylcrotonaldehyde concentration is regulated in the first acetic acid stream, where the first acetic acid stream is obtained as a side stream or bottoms stream from the light ends column. Thus, both the crotonaldehyde concentration and the 2-ethylcrotonaldehyde concentration in the first acetic acid stream can be controlled together.

The first acetic acid stream has a butyl acetate concentration of typically 15 ppm by mass or less, preferably 12 ppm by mass or less, more preferably 10 ppm by mass or less, and furthermore preferably 8 ppm by mass or less.

In a preferred embodiment, the first acetic acid stream has a butyl acetate concentration of typically 15 ppm by mass or less, preferably 10 ppm by mass or less, more preferably 8 ppm by mass or less, and particularly preferably 5 ppm by mass or less (for example, 3 ppm by mass or less). Control of the butyl acetate concentration in the first acetic acid stream to 15 ppm by mass or less allows the second acetic acid stream to have higher quality. The lower limit of the butyl acetate concentration in the first acetic acid stream may be typically 0 ppm by mass, or 0.1 ppm by mass (for example, 0.3 ppm by mass or 1.0 ppm by mass).

The first acetic acid stream has a ratio ($C_{CR}/C_{BA}$) of the crotonaldehyde concentration $C_{CR}$ (ppm by mass) to the butyl acetate concentration $C_{BA}$ (ppm by mass) of typically 2.0 or less, preferably 1.5 or less, more preferably 1.0 or less, and furthermore preferably 0.6 or less. The lower limit of the ratio may be typically 0.1, 0.05, 0.02, 0.01, or 0.001.

The charge liquid to the distillation column in the crotonaldehyde-removing step has a crotonaldehyde concentration of generally 0.01 to 50 ppm by mass (for example, 0.1 to 50 ppm by mass), preferably 0.3 to 30 ppm by mass, more preferably 0.5 to 10 ppm by mass, and furthermore preferably 0.8 to 7.0 ppm by mass (for example, 1.0 to 5.0 ppm by mass).

The distillation column in the crotonaldehyde-removing step is preferably operated so as to meet all the conditions (a-i) to (a-iii). Operation of the crotonaldehyde-removing column so as to meet all the conditions (a-i) to (a-iii) contributes to significantly better crotonaldehyde removal efficiency and allows the acetic acid product to yield a significantly better potassium permanganate test result.

The distillation in the crotonaldehyde-removing step may be performed batchwise. Energy cost can be saved by performing such a batchwise distillation treatment at the time point(s) when crotonaldehyde in a certain amount in at least one of the aqueous phase and the organic phase.

The distillation column in the crotonaldehyde-removing step is operated at a throughput of typically 0.0001 to 50 parts by mass, preferably 0.001 to 30 parts by mass (for example, 0.01 to 10 parts by mass, and particularly 0.1 to 5 parts by mass), per 100 parts by mass of the vapor stream fed to the first distillation column.

The acetic acid production methods according to the present invention may each further include a scrubbing step, in which an offgas from the process is absorptively treated with an absorbing solvent (absorbent) including acetic acid, to separate the offgas into a carbon monoxide-rich stream and an acetic acid-rich stream.

Hereinafter, one embodiment of the present invention will be illustrated. FIG. 1 illustrates an acetic acid production flow chart (methanol carbonylation process) according to an embodiment of the present invention. Acetic acid production equipment relating to this acetic acid production flow includes a reactor 1, an evaporator 2, a distillation column 3, a decanter 4, a distillation column 5, a distillation column 6, an ion exchange resin column 7, a scrubbing system 8, an acetaldehyde-removing system 9, a distillation column 10, condensers 1a, 2a, 3a, 5a, 6a, and 10a, a heat exchanger 2b, reboilers 3b, 5b, 6b, and 10b, lines 11 to 56 and 58 to 63, and a pump 57. The equipment is configured so as to be capable of continuously producing acetic acid. In an acetic acid production method according to the embodiment, a reaction step, an evaporation step (flash step), a first distillation step, a second distillation step, a third distillation step, a crotonaldehyde-removing step, and an adsorptive removing step are performed respectively in the reactor 1, the evaporator 2, the distillation column 3, the distillation column 5, the distillation column 6, the distillation column 10, and the ion exchange resin column 7. The first distillation step is also referred to as a light ends-removing step, the second distillation step is also referred to as a dehydration step, and the third distillation step is also referred to as a heavy ends-removing step. In addition, a liquid-liquid separation step and an acetaldehyde-removing (acetaldehyde-removing treatment) step are performed respectively in the decanter 4 and in the acetaldehyde-removing system 9. In the present invention, steps are not limited to the above-mentioned steps. For example, the equipment may not include one or more of facilities such as the distillation column 5, the distillation column 6, and the ion exchange resin column 7. The equipment may further include a product column downstream from the ion exchange resin column 7, as described later.

The reactor 1 is a unit with which the reaction step is performed. The reaction step is the step of continuously forming acetic acid through a reaction (methanol-carbonylation reaction) represented by Chemical Formula (1) below. During steady operation of the acetic acid production equipment, the reactor 1 contains or houses a reaction mixture, which is stirred typically with a stirrer. The reaction mixture includes starting materials methanol and carbon monoxide, a metal catalyst, a promoter, water, production target acetic acid, and various by-products. In the reaction mixture, a liquid phase and a gas phase are in an equilibrium state. Chemical Formula (1) is expressed as follows:

$$CH_3OH + CO \rightarrow CH_3COOH \qquad (1)$$

The starting materials in the reaction mixture are liquid methanol and gaseous carbon monoxide. Methanol is fed from a methanol storage unit (not shown) through the line 11 to the reactor 1 continuously at a predetermined flow rate.

Carbon monoxide is fed from a carbon monoxide storage unit (not shown) through the line 12 to the reactor 1 continuously at a predetermined flow rate. The carbon monoxide has not always to be pure carbon monoxide and may include a small amount (typically 5 mass percent or less, and preferably 1 mass percent or less) of one or more other gases such as nitrogen, hydrogen, carbon dioxide, and oxygen.

The metal catalyst in the reaction mixture is used to promote or accelerate the methanol-carbonylation reaction and may be selected typically from rhodium catalysts and iridium catalysts. A non-limiting example of the rhodium catalysts is a rhodium complex represented by the chemical formula: $[Rh(CO)_2I_2]^-$. A non-limiting example of the iridium catalysts is an iridium complex represented by the chemical formula: $[Ir(CO)_2I_2]^-$. The metal catalyst is preferably selected from metal complex catalysts. The catalyst may be present in the reaction mixture in a concentration (in terms of metal) of typically 100 to 10000 ppm by mass, preferably 200 to 5000 ppm by mass, and furthermore preferably 400 to 3000 ppm by mass, relative to the totality of the liquid phase of the reaction mixture.

The promoter is an iodide to assist the action (catalysis) of the catalyst and may be selected typically from methyl iodide and ionic iodides. Methyl iodide can offer the action of promoting the catalysis of the catalyst. Methyl iodide may be present in a concentration of typically 1 to 20 mass percent, relative to the totality of the liquid phase of the reaction mixture. The ionic iodides are iodides that form iodide ions in the liquid reaction mixture, of which ionic metal iodides are typified. The ionic iodides can offer the action of stabilizing the catalyst and/or the action of restraining side reactions. Non-limiting examples of the ionic iodides include alkali metal iodides such as lithium iodide, sodium iodide, and potassium iodide. The ionic iodide(s) may be present in the reaction mixture in a concentration of typically 1 to 25 mass percent, and preferably 5 to 20 mass percent, relative to the totality of the liquid phase of the reaction mixture. For example, when an iridium catalyst is used, a ruthenium compound and/or an osmium compound may be used as the promoter. These compounds may be used in a total amount of typically 0.1 to 30 moles (in terms of metal), and preferably 0.5 to 15 moles (in terms of metal), per mole (in terms of metal) of iridium.

Water in the reaction mixture is a component necessary for the formation of acetic acid, due to the reaction mechanism of the methanol-carbonylation reaction, and is a component necessary for dissolving water-soluble components in the reaction system. The water may be present in the reaction mixture in a concentration of typically 0.1 to 15 mass percent, preferably 0.8 to 10 mass percent, furthermore preferably 1 to 6 mass percent, and particularly preferably 1.5 to 4 mass percent, relative to the totality of the liquid phase of the reaction mixture. The water concentration is preferably 15 mass percent or less, so as to minimize energy necessary for the removal of water in the acetic acid purification process and for performing the acetic acid production more efficiently. To control the water concentration, water may be fed to the reactor 1 continuously at a predetermined flow rate.

Acetic acid in the reaction mixture includes acetic acid that has been charged into the reactor 1 before operation of the acetic acid production equipment; and acetic acid that is formed as a main product of the methanol-carbonylation reaction. Acetic acid as above is capable of functioning as a solvent in the reaction system. Acetic acid may be present in the reaction mixture in a concentration of typically 50 to 90 mass percent, and preferably 60 to 80 mass percent, relative to the totality of the liquid phase of the reaction mixture.

A non-limiting example of main by-products contained in the reaction mixture is methyl acetate. Methyl acetate can be formed from the reaction between acetic acid and methanol. Methyl acetate may be present in the reaction mixture in a concentration of typically 0.1 to 30 mass percent, and preferably 1 to 10 mass percent, relative to the totality of the liquid phase of the reaction mixture. A non-limiting example of the by-products contained in the reaction mixture is hydrogen iodide. When the catalyst with or without the promoter as above is used, hydrogen iodide is unavoidably formed due to the reaction mechanism of the methanol-carbonylation reaction. Hydrogen iodide may be present in the reaction mixture in a concentration of typically 0.01 to 2 mass percent, relative to the totality of the liquid phase of the reaction mixture.

Non-limiting examples of the by-products also include hydrogen, methane, carbon dioxide, acetaldehyde, crotonaldehyde, 2-ethylcrotonaldehyde, butyl acetate, dimethyl ether, alkanes, formic acid, and propionic acid; as well as alkyl iodides such as ethyl iodide, propyl iodide, butyl iodide, hexyl iodide, and decyl iodide.

The liquid reaction mixture has an acetaldehyde concentration of typically 500 ppm by mass or less, preferably 450 ppm by mass or less, more preferably 400 ppm by mass or less, furthermore preferably 350 ppm by mass or less, and particularly preferably 300 ppm by mass or less (for example, 250 ppm by mass or less). The lower limit of the acetaldehyde concentration in the liquid reaction mixture is typically 1 ppm by mass (or 10 ppm by mass).

The liquid reaction mixture has a crotonaldehyde concentration of typically 5 ppm by mass or less, preferably 3 ppm by mass or less, and furthermore preferably 2 ppm by mass or less. The lower limit of the crotonaldehyde concentration in the liquid reaction mixture is 0 ppm, but may be typically 0.1 ppm by mass (or 0.2 ppm by mass). The liquid reaction mixture has an 2-ethylcrotonaldehyde concentration of typically 5 ppm by mass or less, preferably 3 ppm by mass or less, and furthermore preferably 2 ppm by mass or less. The lower limit of the 2-ethylcrotonaldehyde concentration in the liquid reaction mixture is 0 ppm, but may be typically 0.1 ppm by mass or 0.2 ppm by mass.

In the present invention, the crotonaldehyde concentration in the first acetic acid stream, which is drawn from the light ends column, is controlled to a specific level or lower; and/or the reflux ratio at the dehydration column is controlled to a specific level or higher, as described above, to achieve the object to give an acetic acid product yielding a better potassium permanganate test result. In addition, for example, the hydrogen partial pressure in the reactor is increased, and/or the reflux ratio at the light ends column is increased, so as to lower the crotonaldehyde concentration in the first acetic acid stream. When the reflux ratio(s) at the light ends column and/or at the dehydration column is increased, crotonaldehyde is concentrated at the column top of the distillation column. Such concentrated crotonaldehyde, when recycled to the reactor, is hydrogenated into butyl alcohol, and the butyl alcohol in turn reacts with acetic acid to be converted into butyl acetate, and is thus become harmless to the potassium permanganate test. In addition, the increase in hydrogen partial pressure in the reactor facilitates hydrogenation of crotonaldehyde in the reactor, and thus facilitates or promotes conversion of crotonaldehyde through butyl alcohol into harmless butyl acetate, as above. Accordingly, the liquid reaction mixture in the present invention tends to have a higher butyl acetate concentration. However, such increase in butyl acetate concentration may cause the acetic acid product to have a lower purity. To eliminate or minimize this, the butyl acetate concentration in the liquid reaction mixture is preferably controlled to typically 0.1 to 15 ppm by mass (particularly preferably 1 to 12 ppm by mass, and especially preferably 2 to 9 ppm by mass).

In the present invention, the reflux ratio at the light ends column is controlled to a specific level or higher so as to give an acetic acid product yielding a better potassium permanganate test result, as described above. At a higher reflux ratio at the light ends column, crotonaldehyde is more concentrated at the column top. Such concentrated crotonaldehyde, when recycled to the reactor, is hydrogenated into butyl alcohol, and the butyl alcohol in turn reacts with acetic acid to give butyl acetate, which is harmless to the potassium permanganate test. Accordingly, the butyl acetate concentration in the liquid reaction mixture tends to increase in the present invention. However, such increase in butyl acetate concentration may cause the acetic acid product to have lower quality. To eliminate or minimize this, the butyl acetate concentration in the liquid reaction mixture is preferably controlled to typically 0.1 to 15 ppm by mass (particularly preferably 1 to 12 ppm by mass, and especially preferably 2 to 9 ppm by mass).

The reaction mixture may include metals exemplified by corrodible metals (also called corrosible metals) such as iron, nickel, chromium, manganese, and molybdenum, where the corrodible metals are metals resulting from corrosion of the equipment; and other metals such as cobalt, zinc, and copper. Hereinafter, the metals such as corrodible metals are also generically referred to as "corrodible metals and other metals".

In the reactor 1, in which the reaction mixture as above is present, the reaction temperature is set typically to 150° C. to 250° C., the reaction pressure as a total pressure is set typically to 2.0 to 3.5 MPa (absolute pressure), and the carbon monoxide partial pressure is set typically to 0.4 to 1.8 MPa (absolute pressure), and preferably to 0.6 to 1.5 MPa (absolute pressure).

In a preferred embodiment, in the reactor 1 housing the reaction mixture as above, the reaction temperature is set typically to 150° C. to 250° C., the reaction pressure as a total pressure is set typically to 2.0 to 3.5 MPa (absolute pressure), and the carbon monoxide partial pressure is set typically to 0.4 to 1.8 MPa (absolute pressure), preferably to 0.6 to 1.6 MPa (absolute pressure), and furthermore preferably to 0.9 to 1.4 MPa (absolute pressure).

Vapors in the gas phase in the reactor 1 during operation of the equipment typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. The vapors can be drawn from the reactor 1 through the line 13. The inside pressure of the reactor 1 can be controlled by regulating the amount of vapors to be drawn, and is typically maintained at a constant level. The vapors drawn from the reactor 1 are introduced into the condenser 1*a*.

In a preferred embodiment, vapors in the gas phase in the reactor 1 during operation of the equipment typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. Hydrogen is not only contained in the starting material carbon monoxide, but also formed by a shift reaction ($CO+H_2O \rightarrow H_2+CO_2$) which occurs in the reactor 1. The hydrogen partial pressure in the reactor 1 is typically 0.001 MPa (absolute pressure) or more (for example, 0.005 MPa or more), preferably 0.01 MPa (absolute pressure) or more (for example, 0.015 MPa or more), more preferably 0.02 MPa (absolute pressure) or more, furthermore preferably 0.04 MPa (absolute pressure) or more, and particularly preferably 0.06 MPa (absolute pressure) or more (for example, 0.07 MPa (absolute pressure) or more). An excessively high hydrogen partial pressure in the reactor may cause increase in amount of acetaldehyde formation, and increase in amount of crotonaldehyde by aldol condensation; and, conversely, an excessively low hydrogen partial pressure may impede the reaction of crotonaldehyde into butyl alcohol, and, in this case, the reaction rate significantly varies with a small variation in hydrogen, and this unstabilizes the operation. The vapors in the gas phase in the reactor 1 can be drawn from the reactor 1 through the line 13. The inside pressure of the reactor 1 may be controlled by regulating the amount of the vapors to be drawn out, and is typically maintained at a constant level. The vapors drawn from the reactor 1 are introduced into the condenser 1*a*.

The condenser 1*a* cools and partially condenses the vapors from the reactor 1 to separate the vapors into condensates and gases. The condensates typically include methyl iodide, hydrogen iodide, water, methyl acetate, acetic acid, dimethyl ether, methanol, acetaldehyde, formic acid, and propionic acid. The condensates are introduced and recycled from the condenser 1*a* through the line 14 to the reactor 1. The gases typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gases are fed from the condenser 1*a* through the line 15 to the scrubbing system 8. In the scrubbing system 8, useful components (such as methyl iodide, water, methyl acetate, and acetic acid) are separated and recovered from the gases fed from the condenser 1a. In the embodiment, the separation and recovery employs a wet process using an absorbing liquid (absorbent) for collecting useful components from the gases. The absorbing liquid is preferably selected from absorbing solvents containing at least one of acetic acid and methanol. The absorbing liquid may contain methyl acetate. For example, condensates derived from vapors from the after-mentioned distillation column 6 are usable as the absorbing liquid. The separation and recovery may employ a pressure swing adsorption process. The separated, recovered useful components (such as methyl iodide) are introduced and recycled from the scrubbing system 8 through the recycle line 48 to the reactor 1. Residual gases after the collection of useful components are discarded through the line 49. The gases discharged from the line 49 can be used as a carbon monoxide (CO) source to be introduced into the bottom of the after-mentioned evaporator 2, or into the residue recycle lines 18 and 19. The treatment in the scrubbing system 8, the subsequent recycling to the reactor 1, and the discarding are also applicable to after-mentioned gases fed from other condensers to the scrubbing system 8. The production methods according to the present invention preferably include a scrubbing step in which an offgas from the process is subjected to an absorbing treatment with an absorbing solvent containing acetic acid, to separate the offgas into a carbon monoxide-rich stream and an acetic acid-rich stream.

Acetic acid is continuously formed in the reactor 1 during operation of the equipment, as described above. A reaction mixture containing such acetic acid is continuously drawn from the reactor 1 at a predetermined flow rate, and introduced through the line 16 into the subsequent (downstream) evaporator 2.

The evaporator 2 is a unit with which the evaporation step (flash step) is performed. The evaporation step is the step of partially evaporating the reaction mixture to separate the mixture into a vapor stream (volatile phase) and a residue stream (low volatile phase), where the reaction mixture is continuously introduced through the line 16 (reaction mixture feed line) into the evaporator 2. The evaporation may be performed by decompressing the reaction mixture with or without heating. In the evaporation step, the vapor stream temperature is typically 100° C. to 260° C., and preferably 120° C. to 200° C.; the residue stream temperature is typically 80° C. to 200° C., and preferably 100° C. to 180° C.; and the evaporator internal pressure is typically 50 to 1000 kPa (absolute pressure). The ratio (mass ratio) of the vapor stream to the residue stream, which are separated from each other in the evaporation step, is typically from 10:90 to 50:50.

The vapors formed in this step typically include methyl iodide, hydrogen iodide, water, methyl acetate, acetic acid, dimethyl ether, methanol, acetaldehyde, formic acid, and propionic acid. The vapors are continuously drawn from within the evaporator 2 to the line 17 (vapor stream discharge line). Of the vapor stream drawn from within the evaporator 2, a part is continuously introduced into the condenser 2a; and another part is continuously introduced through the line 21 into the subsequent (downstream) distillation column 3. The vapor stream has an acetic acid concentration of typically 40 to 85 mass percent (preferably 50 to 85 mass percent, and furthermore preferably 50 to 75 mass percent (for example, 55 to 75 mass percent), a methyl iodide concentration of typically 2 to 50 mass percent (preferably 5 to 30 mass percent), a water concentration of typically 0.2 to 20 mass percent (preferably 1 to 15 mass percent), and a methyl acetate concentration of typically 0.2 to 50 mass percent (preferably 2 to 30 mass percent). The residue stream formed in the step includes the catalyst and the promoter (such as methyl iodide or lithium iodide) which have been contained in the reaction mixture; and water, methyl acetate, acetic acid, formic acid, propionic acid, and other substances that remain without volatilization in the step. The residue stream is continuously introduced from the evaporator 2 through the line 18 into the heat exchanger 2b, using the pump 57. The heat exchanger 2b cools the residue stream from the evaporator 2. The cooled residue stream is continuously introduced and recycled from the heat exchanger 2b through the line 19 to the reactor 1. The line 18 and the line 19 are collectively referred to as a "residue recycle line(s)". The residue stream has an acetic acid concentration of typically 55 to 90 mass percent, and preferably 60 to 85 mass percent.

In a preferred embodiment, the vapors formed in the step typically include methyl iodide, hydrogen iodide, water, methyl acetate, acetic acid, dimethyl ether, methanol, acetaldehyde, crotonaldehyde, 2-ethylcrotonaldehyde, butyl acetate, formic acid, and propionic acid; as well as alkyl iodides such as ethyl iodide, propyl iodide, butyl iodide, hexyl iodide, and decyl iodide. The vapors are continuously drawn from within the evaporator 2 to the line 17 (vapor stream discharge line). Of the vapor stream drawn from within the evaporator 2, a part is continuously introduced into the condenser 2a, and another part is continuously introduced through the line 21 into the subsequent (downstream) distillation column 3. The vapor stream has an acetic acid concentration of typically 50 to 85 mass percent (preferably 55 to 75 mass percent), a methyl iodide concentration of typically 2 to 50 mass percent (preferably 5 to 30 mass percent), a water concentration of typically 0.2 to 20 mass percent (preferably 1 to 15 mass percent), and a methyl acetate concentration of typically 0.2 to 50 mass percent (preferably 2 to 30 mass percent). The vapor stream has a crotonaldehyde concentration of typically 0 to 5.0 ppm by mass (for example, 0.01 to 4.0 ppm by mass), preferably 0.1 to 3.0 ppm by mass, and furthermore preferably 0.2 to 2.0 ppm by mass. The vapor stream has an 2-ethylcrotonaldehyde concentration of typically 0 to 3.0 ppm by mass (for example, 0.01 to 2.5 ppm by mass), preferably 0.02 to 2.0 ppm by mass, and more preferably 0.03 to 0.8 ppm by mass. The vapor stream has a butyl acetate concentration of typically 0.1 to 13 ppm by mass, preferably 0.2 to 12 ppm by mass, and furthermore preferably 0.3 to 9 ppm by mass.

The residue stream formed in the step in the embodiment includes the catalyst and the promoter (such as methyl iodide or lithium iodide) which have been contained in the reaction mixture; and water, methyl acetate, acetic acid, crotonaldehyde, 2-ethylcrotonaldehyde, butyl acetate, formic acid, propionic acid, and other substances that remain without volatilization in the step. The residue stream is continuously introduced from the evaporator 2 through the line 18 into the heat exchanger 2b, using the pump 57. The heat exchanger 2b cools the residue stream from the evaporator 2. The cooled residue stream is continuously introduced and recycled from the heat exchanger 2b through the line 19 to the reactor 1. The line 18 and the line 19 are collectively referred to as a "residue recycle line(s)". The residue stream has an acetic acid concentration of typically 55 to 90 mass percent, and preferably 60 to 85 mass percent.

To introduce a carbon monoxide-containing gas, the carbon monoxide-containing gas introducing line 54 is preferably coupled to the bottom of the evaporator 2 and/or to the residue recycle line(s) (line 18 and/or line 19). Introduction of carbon monoxide into the residue (bottoms) accumulating in the lower part of the evaporator 2 and/or into the residue stream passing through the residue recycle lines 18 and 19 (in particular, the line 18) allows carbon monoxide to be dissolved in a larger amount in the residue stream and allows the catalyst to be more stable and to resist sedimentation and accumulation. The carbon monoxide-containing gas to be introduced has a carbon monoxide content of typically 10 mass percent or more, preferably 20 mass percent or more, furthermore preferably 40 mass percent or more, and particularly preferably 60 mass percent or more.

The condenser 2a cools and partially condensates the vapor stream from the evaporator 2 to separate the vapor stream into condensates and gases. The condensates typically include methyl iodide, hydrogen iodide, water, methyl acetate, acetic acid, dimethyl ether, methanol, acetaldehyde, formic acid, and propionic acid, and are introduced and recycled from the condenser 2a through the lines 22 and 23 to the reactor 1. The gases typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid, and are fed from the condenser 2a through the lines 20 and 15 to the scrubbing system 8. The acetic acid formation reaction in the reaction step is an exothermic reaction. In the evaporation step (flash step), a part of heat accumulated in the reaction mixture is transferred to the vapors derived from the reaction mixture. The vapors are cooled in the condenser 2a to give condensates, and the condensates are recycled to the reactor 1. Specifically, this acetic acid production equipment enables efficient removal of heat, which is generated in the methanol-carbonylation reaction, by the working of the condenser 2a.

In a preferred embodiment, the condenser 2a cools and partially condensates the vapor stream from the evaporator 2 to separate the vapor stream into condensates and gases. The condensates typically include methyl iodide, hydrogen iodide, water, methyl acetate, acetic acid, dimethyl ether, methanol, acetaldehyde, crotonaldehyde, 2-ethylcrotonaldehyde, butyl acetate, formic acid, and propionic acid. The condensates are introduced and recycled from the condenser 2a through the lines 22 and 23 to the reactor 1. The gases typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gases are fed from the condenser 2a through the lines 20 and 15 to the scrubbing system 8. The acetic acid formation reaction in the reaction step is an exothermic reaction. In the evaporation step (flash step), a part of heat accumulated in the reaction mixture is transferred to the vapors derived from the reaction mixture. The vapors are cooled in the condenser 2a to give condensates, and the condensates are recycled to the reactor 1. Specifically, this acetic acid production equipment enables efficient removal of heat, which is generated in the methanol-carbonylation reaction, by the working of the condenser 2a.

The distillation column 3 is a unit with which the first distillation step is performed. The distillation column 3 in the embodiment is characterized as a so-called light ends column. The first distillation step is the step of subjecting the vapor stream, which is continuously introduced into the distillation column 3, to a distillation treatment to separate and remove light ends therefrom. More specifically, the first distillation step is the step of separating the vapor stream, by distillation, into an overhead stream rich in at least one light end selected from methyl iodide and acetaldehyde, and an acetic acid stream rich in acetic acid. The distillation column 3 may be selected typically from rectification columns such as plate columns and packed columns. A plate column, when employed as the distillation column 3, typically has 5 to 50 theoretical plates, and is operated at a reflux ratio of typically 0.5 to 3000, where the reflux ratio may be determined according to the number of theoretical plates. In the distillation column 3, the column top pressure is set typically to 80 to 160 kPa (gauge pressure); and the column bottom pressure is set higher than the column top pressure and is typically from 85 to 180 kPa (gauge pressure). In the distillation column 3, the column top temperature is set typically to a temperature which is lower than the boiling point of acetic acid at the set column top pressure and which is from 90° C. to 130° C.; and the column bottom temperature is set typically to a temperature which is equal to or higher than the boiling point of acetic acid at the set column bottom pressure and which is from 120° C. to 160° C.

In a preferred embodiment, in the distillation column 3, the column top pressure is set typically to 80 to 160 kPa (gauge pressure); and the column bottom pressure is set higher than the column top pressure and is typically from 85 to 180 kPa (gauge pressure). In the distillation column 3, the column top temperature is set typically to a temperature which is lower than the boiling point of acetic acid at the set column top pressure and which is from 90° C. to 130° C.; and the column bottom temperature is set typically to a temperature which is equal to or higher than the boiling point of acetic acid at the set column bottom pressure and which is from 115° C. to 165° C. (and preferably from 120° C. to 160° C.)

At the distillation column 3, the vapor stream from the evaporator 2 is continuously introduced through the line 21; vapors as an overhead stream are continuously drawn from a column top portion to the line 24; and bottoms are continuously drawn from a column bottom portion to the line 25. There is disposed the reboiler 3b. An acetic acid stream (first acetic acid stream; liquid) as a side stream is continuously drawn, through the line 27, from a portion at a height level between the column top portion and the column bottom portion in the distillation column 3.

The vapors drawn from the column top portion of the distillation column 3 include light ends in larger amounts as compared with the bottoms and side stream from the distillation column 3, where the light ends herein are components having lower boiling points as compared with acetic acid. The vapors typically include methyl iodide, hydrogen iodide, water, methyl acetate, dimethyl ether, methanol, acetaldehyde, and formic acid. The vapors also include acetic acid. The vapors as above are continuously introduced through the line 24 to the condenser 3a.

In a preferred embodiment, the vapors drawn from the column top portion of the distillation column 3 include light ends in larger amounts as compared with the bottoms and side stream from the distillation column 3, where light ends herein are components having lower boiling points as compared with acetic acid. The vapors typically include methyl iodide, hydrogen iodide, water, methyl acetate, dimethyl ether, methanol, acetaldehyde, crotonaldehyde, and formic acid. The vapors also include acetic acid. The vapors as above are continuously introduced through the line 24 into the condenser 3a.

The condenser 3a cools and partially condensates the vapors from the distillation column 3 to separate the vapors into condensates and gases. The condensates typically include methyl iodide, hydrogen iodide, water, methyl acetate, acetic acid, dimethyl ether, methanol, acetaldehyde, and formic acid, and are continuously introduced from the condenser 3a through the line 28 to the decanter 4. The condensates introduced into the decanter 4 are liquid-liquid separated into an aqueous phase (upper phase) and an organic phase (methyl iodide phase; lower phase). The aqueous phase includes water, and other components such as methyl iodide, hydrogen iodide, methyl acetate, acetic acid, dimethyl ether, methanol, acetaldehyde, and formic acid. The organic phase includes methyl iodide, and other components such as hydrogen iodide, water, methyl acetate, acetic acid, dimethyl ether, methanol, acetaldehyde, and formic acid. In the embodiment, of the aqueous phase, a part is refluxed through the line 29 to the distillation column 3; and another part is introduced and recycled through the lines 29, 30, and 23 to the reactor 1. Of the organic phase, a part is introduced and recycled through the lines 31 and 23 to the reactor 1. Another part of the organic phase and/or another part of the aqueous phase is introduced through the lines 31 and 50, and/or through the lines 30 and 51 to the acetaldehyde-removing system 9.

In a preferred embodiment, the condenser 3a cools and partially condensates the vapors from the distillation column 3 to separate the vapors into condensates and gases. The condensates typically include methyl iodide, hydrogen iodide, water, methyl acetate, acetic acid, dimethyl ether, methanol, acetaldehyde, crotonaldehyde, and formic acid, and are continuously introduced from the condenser 3a through the line 28 into the decanter 4. The condensates introduced into the decanter 4 are liquid-liquid separated into an aqueous phase (upper phase) and an organic phase (methyl iodide phase; lower phase). The aqueous phase includes water, and other components such as methyl iodide, hydrogen iodide, methyl acetate, acetic acid, dimethyl ether, methanol, acetaldehyde, crotonaldehyde, and formic acid. The organic phase includes methyl iodide, and other components such as hydrogen iodide, water, methyl acetate, acetic acid, dimethyl ether, methanol, acetaldehyde, crotonaldehyde, and formic acid.

According to the present invention, a phase to be subjected to the acetaldehyde-removing step is determined or selected as follows. Specifically, in the liquid-liquid separation step (for example, liquid-liquid separation in the decanter 4), a process stream including water, acetic acid (AC), methyl iodide (MeI), and acetaldehyde (AD) is liquid-liquid separated into an aqueous phase and an organic phase; and the phase to be subjected to the acetaldehyde-removing step is determined on the basis of a factor or factors selected from the acetaldehyde concentration in the aqueous phase, the acetaldehyde concentration in the organic phase, the methyl acetate concentration in the aqueous phase, the methyl acetate concentration in the organic phase, the totality of the methyl acetate concentration in the aqueous phase and the methyl acetate concentration in the organic phase, the temperature (liquid temperature) in the liquid-liquid separation, the acetaldehyde partition coefficient (AD partition coefficient) determined by an equation as follows, and the methyl acetate partition coefficient (MA partition coefficient) determined by an equation as follows. In another aspect, there are indicated preferred liquid-liquid separation conditions when the organic phase is subjected to the acetaldehyde-removing step, and preferred liquid-liquid separation conditions when the aqueous phase is subjected to the acetaldehyde-removing step. The equations are expressed as follows:

AD partition coefficient={AD concentration (mass percent) in aqueous phase}/{AD concentration (mass percent) in organic phase}

MA partition coefficient={MA concentration (mass percent) in aqueous phase}/{MA concentration (mass percent) in organic phase}

In an embodiment of the acetic acid production methods according to the present invention, the liquid-liquid separation step meets at least one of conditions (b-i) to (b-v), and at least a part of the aqueous phase is subjected to the treatment in the acetaldehyde-removing step, where the conditions (b-i) to (b-v) are expressed as follows:

(b-i) the aqueous phase has an acetaldehyde concentration of 28.1 mass percent or less, and/or the organic phase has an acetaldehyde concentration of 24.8 mass percent or less;

(b-ii) the liquid-liquid separation is performed at a temperature of 70° C. or lower;

(b-iii) the aqueous phase has a methyl acetate concentration of 12.0 mass percent or less, and/or the organic phase has a methyl acetate concentration of 47.6 mass percent or less, and/or the totality of the methyl acetate concentration in the aqueous phase and the methyl acetate concentration in the organic phase is 59.6 mass percent or less;

(b-iv) an acetaldehyde partition coefficient is 1.1 or more, where the acetaldehyde partition coefficient is the ratio of the acetaldehyde concentration (mass percent) in the aqueous phase to the acetaldehyde concentration (mass percent) in the organic phase; and (b-v) a methyl acetate partition coefficient is 0.25 or more, where the methyl acetate partition coefficient is the ratio of the methyl acetate concentration (mass percent) in the aqueous phase to the methyl acetate concentration (mass percent) in the organic phase.

Relating to the condition (b-i), the acetaldehyde concentration in the aqueous phase is typically 0.045 to 28.1 mass percent, preferably 0.098 to 10 mass percent, furthermore preferably 0.098 to 3.0 mass percent, and particularly preferably 0.098 to 1.0 mass percent (for example, 0.15 to 0.9 mass percent); whereas the acetaldehyde concentration in the organic phase is typically 0.013 to 24.8 mass percent, preferably 0.030 to 2.0 mass percent, furthermore preferably 0.030 to 0.50 mass percent, and particularly preferably 0.030 to 0.24 mass percent. Relating to the condition (b-i), it is preferred that the aqueous phase has an acetaldehyde concentration of 28.1 mass percent or less, and the organic phase has an acetaldehyde concentration of 24.8 mass percent or less. When the condition (b-i) is met, the liquid-liquid separation step feed liquid (such as the liquid to be fed to the decanter 4) has an acetaldehyde concentration of typically 26.0 mass percent or less (for example, 0.026 to 26.0 mass percent), preferably 0.057 to 10 mass percent, furthermore preferably 0.057 to 3.0 mass percent, and particularly preferably 0.057 to 1.0 mass percent (for example, 0.057 to 0.42 mass percent). If the aqueous phase has an acetaldehyde concentration of greater than 28.1 mass percent, and the organic phase has an acetaldehyde concentration of greater than 24.8 mass percent, the AD partition coefficient becomes low (for example, less than 1.1). Thus, the treatment of the aqueous phase in the acetaldehyde-removing step has very small advantages, in comparisons and considerations between the acetaldehyde recovery amount and the need for equipment that has very high corrosion resistance and is therefore expensive.

Relating to the condition (b-ii), the temperature (liquid temperature) in the liquid-liquid separation is typically −5° C. to 70° C., preferably −5° C. to 60° C., more preferably −5° C. to 51° C. (for example, −5° C. to 45° C.), and furthermore preferably −5° C. to 41° C. (for example, −5° C. to 31° C.). The liquid-liquid separation, if performed at a temperature (liquid temperature) of higher than 70° C., causes the AD partition coefficient to be very low, and this leads to very small advantages of the treatment of the aqueous phase in the acetaldehyde-removing step.

Relating to the condition (b-iii), the methyl acetate concentration in the aqueous phase is typically 1.2 to 12.0 mass percent, preferably 2.0 to 12.0 mass percent, and furthermore preferably 5.0 to 12.0 mass percent (for example, 6.0 to 12.0 mass percent); whereas the methyl acetate concentration in the organic phase is typically 2.2 to 47.6 mass percent, preferably 5.0 to 42 mass percent, and furthermore preferably 8.0 to 35 mass percent (for example, 10 to 30 mass percent). Relating to the condition (b-iii), it is preferred that the aqueous phase has a methyl acetate concentration of 12.0 mass percent or less, and the organic phase has a methyl acetate concentration of 47.6 mass percent or less. The totality of the methyl acetate concentration (mass percent) in the aqueous phase and the methyl acetate concentration (mass percent) in the organic phase is typically 59.6 mass percent or less (for example, 4.2 to 59.6 mass percent), preferably 6.0 to 54 mass percent, more preferably 8.0 to 54 mass percent, furthermore preferably 10.0 to 54 mass percent, and particularly preferably 14.0 to 47 mass percent (for example, 16 to 42 mass percent). When the condition (b-iii) is met, the liquid-liquid separation step feed liquid (such as the liquid to be fed to the decanter 4) has a methyl acetate concentration of typically 38.2 mass percent or less (for example, 2.0 to 38.2 mass percent), preferably 5.0 to 31 mass percent, more preferably 8.0 to 25 mass percent, and furthermore preferably 10.0 to 25 mass percent. Assume that the aqueous phase has a methyl acetate concentration of greater than 12.0 mass percent, the organic phase has a methyl acetate concentration of greater than 47.6 mass percent, and the totality of the methyl acetate concentration (mass percent) in the aqueous phase and the methyl acetate concentration (mass percent) in the organic phase is greater than 59.6 mass percent. In this case, the AD partition coefficient becomes typically less than 1.1, and this leads to very small advantages of the treatment of the aqueous phase in the acetaldehyde-removing step, for reasons as above.

Relating to the condition (b-iv), the AD partition coefficient is typically 1.1 to 8.0, preferably 1.5 to 6.0, and furthermore preferably 1.9 to 5.0. If the AD partition coefficient is less than 1.1, the aqueous phase has a low acetaldehyde concentration. This causes the acetaldehyde-removing treatment of the aqueous phase to be industrially very disadvantageous, because the treatment requires much energy and often causes corrosion of the equipment. In contrast, when the AD partition coefficient is 1.1 or more (preferably 1.5 or more, and furthermore preferably 1.9 or more), the acetaldehyde-removing treatment of the aqueous phase has large advantages for higher acetaldehyde removal efficiency, even upon the use of equipment that has high corrosion resistance.

Relating to the condition (b-v), the MA partition coefficient is 0.25 or more (for example, 0.25 to 0.70), preferably 0.26 or more (for example, 0.26 to 0.65), and furthermore preferably 0.28 or more (for example, 0.28 to 0.60). As described above, the distribution ratio of methyl acetate (MA) between the aqueous phase and the organic phase varies depending on the temperature and the chemical compositions (including not only water and methyl iodide, but also other components such as acetic acid), and can therefore also serve as an index for the control of the acetaldehyde partition coefficient.

In the acetic acid production methods according to the embodiment of the present invention, the liquid-liquid separation step has only to meet at least one of the conditions (b-i) to (b-v), but may meet two or more of the conditions together. Examples of combinations of two or more of the conditions which are preferably met together include the combinations of: (b-i) and (b-ii); (b-i) and (b-iii); (b-i) and (b-iv); (b-i) and (b-v); (b-ii) and (b-iii); (b-ii) and (b-iv); (b-ii) and (b-v); (b-iii) and (b-iv); (b-iii) and (b-v); (b-iv) and (b-v); (b-i), (b-ii), and (b-iii); (b-i), (b-ii), and (b-iv); (b-i), (b-ii), and (b-v); (b-i), (b-iii), and (b-iv); (b-i), (b-iii), and (b-v); (b-i), (b-iv), and (b-v); (b-ii), (b-iii), and (b-iv); (b-ii), (b-iii), and (b-v); (b-ii), (b-iv), and (b-v); (b-iii), (b-iv), and (b-v); (b-i), (b-ii), (b-iii), and (b-iv); (b-i), (b-ii), (b-iii), and (b-v); (b-i), (b-iii), (b-iv), and (b-v); (b-ii), (b-iii), (b-iv), and (b-v); and (b-i), (b-ii), (b-iii), (b-iv), and (b-v). Among them, the liquid-liquid separation step particularly preferably meets at least the conditions (b-i), (b-ii), and (b-iii) together; or at least the conditions (b-i), (b-ii), (b-iii), and (b-iv) together; or all the conditions (b-i), (b-ii), (b-iii), (b-iv), and (b-v) together.

In another embodiment of the acetic acid production methods according to the present invention, the liquid-liquid separation step meets at least one of conditions (b'-i) to (b'-v), and at least a part of the organic phase is treated in the acetaldehyde-removing step, where the conditions (b'-i) to (b'-v) are expressed as follows:

(b'-i) the aqueous phase has an acetaldehyde concentration of 0.045 mass percent or more, and/or the organic phase has an acetaldehyde concentration of 0.013 mass percent or more;

(b'-ii) the liquid-liquid separation is performed at a temperature of −5° C. or higher;

(b'-iii) the aqueous phase has a methyl acetate concentration of 1.2 mass percent or more, and/or the organic phase has a methyl acetate concentration of 2.2 mass percent or more, and/or the totality of the methyl acetate concentration in the aqueous phase and the methyl acetate concentration in the organic phase is 3.4 mass percent or more;

(b'-iv) an acetaldehyde partition coefficient is 4.1 or less, where the acetaldehyde partition coefficient is the ratio of the acetaldehyde concentration (mass percent) in the aqueous phase to the acetaldehyde concentration (mass percent) in the organic phase; and (b'-v) a methyl acetate partition coefficient is 0.8 or less, where the methyl acetate partition coefficient is the ratio of the methyl acetate concentration (mass percent) in the aqueous phase to the methyl acetate concentration (mass percent) in the organic phase.

Relating to the condition (b'-i), the acetaldehyde concentration in the aqueous phase is typically 0.045 to 35 mass percent, preferably 0.15 to 10 mass percent, and furthermore preferably 0.2 to 2.0 mass percent; whereas the acetaldehyde concentration in the organic phase is typically 0.013 to 30 mass percent, preferably 0.05 to 5.0 mass percent, and furthermore preferably 0.1 to 1.0 mass percent. Relating to the condition (b'-i), it is preferred that the aqueous phase has an acetaldehyde concentration of 0.045 mass percent or more, and the organic phase has an acetaldehyde concentration of 0.013 mass percent or more. When the condition (b'-i) is met, the liquid-liquid separation step feed liquid (such as the liquid to be fed to the decanter 4) has an acetaldehyde concentration of typically 0.026 mass percent or more (for example, 0.026 to 32 mass percent), preferably 0.10 to 8.0 mass percent, and furthermore preferably 0.15 to 1.8 mass percent. Assume that the aqueous phase has an acetaldehyde concentration of less than 0.045 mass percent, and the organic phase has an acetaldehyde concentration of less than 0.013 mass percent. In this case, the AD partition coefficient becomes high, and this leads to very small advantages of the treatment of the organic phase in the acetaldehyde-removing step.

Relating to the condition (b'-ii), the temperature (liquid temperature) in the liquid-liquid separation is −5° C. or higher (for example, −5° C. to 90° C.), preferably 0° C. or higher (for example, 0° C. to 90° C.), more preferably 10° C. or higher (for example, 10° C. to 90° C.), furthermore preferably 20° C. or higher (for example, 25° C. to 90° C.), a temperature higher than 30° C. (for example, from higher than 30° C. to 90° C.)), a temperature higher than 35° C. (for example, from higher than 35° C. to 90° C.), a temperature higher than 40° C. (for example, from higher than 40° C. to 90° C.), and particularly preferably a temperature higher than 70° C. (for example, from higher than 70° C. to 90° C.). The liquid-liquid separation, if performed at a temperature (liquid temperature) of lower than −5° C., causes the AD partition coefficient to be typically higher than 4.3. This leads to very small advantages of the treatment of the organic phase in the acetaldehyde-removing step.

Relating to the condition (b'-iii), the methyl acetate concentration in the aqueous phase is typically 1.2 to 20 mass percent, preferably 2.5 to 18 mass percent, more preferably 4.0 to 15 mass percent, furthermore preferably 6.0 to 13 mass percent, and particularly preferably 7.0 to 12 mass percent; whereas the organic phase has a methyl acetate concentration of typically 2.2 to 60 mass percent, preferably 5.8 to 48 mass percent, more preferably 8.0 to 40 mass percent, furthermore preferably 10.0 to 30.0 mass percent, and particularly preferably 11.0 to 25.0 mass percent. Relating to the condition (b'-iii), it is preferred that the aqueous phase has a methyl acetate concentration of 1.2 mass percent or more, and the organic phase has a methyl acetate concentration of 2.2 mass percent or more. The totality of the methyl acetate concentration (mass percent) in the aqueous phase and the methyl acetate concentration (mass percent) in the organic phase is typically 3.4 to 75 mass percent, preferably 8.3 to 60 mass percent (for example, 10 to 40 mass percent), more preferably 15.0 to 50 mass percent, and furthermore preferably 25 to 53 mass percent. When the condition (b'-iii) is met, the liquid-liquid separation step feed liquid (such as the liquid to be fed to the decanter 4) has a methyl acetate concentration of typically 2.0 to 50 mass percent, preferably 5.0 to 38 mass percent, more preferably 8.0 to 35 mass percent, furthermore preferably 10.0 to 32 mass percent, and particularly preferably 15.0 to 31 mass percent. Assume that the aqueous phase has a methyl acetate concentration of less than 1.2 mass percent, the organic phase has a methyl acetate concentration of less than 2.2 mass percent, and the totality of the methyl acetate concentration (mass percent) in the aqueous phase and the methyl acetate concentration (mass percent) in the organic phase is less than 3.4 mass percent. In this case, the AD partition coefficient becomes high, and this leads to small advantages of the treatment of the organic phase in the acetaldehyde-removing step.

Relating to the condition (b'-iv), the AD partition coefficient is 4.1 or less (for example, 0.5 to 4.1), preferably 3.35 or less (for example, 0.6 to 3.35), more preferably 3 or less (0.7 to 3), furthermore preferably 2.8 or less (for example, 0.8 to 2.8), particularly preferably 2.5 or less (for example, 0.8 to 2.5), especially preferably 2.3 or less (for example, 0.9 to 2.3), and still especially preferably 2.0 or less (for example, 1.0 to 2.0). If the AD partition coefficient is greater than 4.1, the organic phase has a very low acetaldehyde concentration. This leads to very small advantages of the treatment of the organic phase in the acetaldehyde-removing step. Non-limiting examples of the way to give a most preferred AD partition coefficient (less than 1.1) for the acetaldehyde-removing treatment of the organic phase include control of the acetaldehyde concentration in the aqueous phase to greater than 28.1 mass percent; control of the acetaldehyde concentration in the organic phase to greater than 24.8 mass percent; control of the acetaldehyde concentration in the liquid-liquid separation step feed liquid to greater than 26.0 mass percent; control of the liquid-liquid separation temperature to higher than 70° C.; control of the methyl acetate concentration in the aqueous phase to greater than 12.0 mass percent; control of the methyl acetate concentration in the organic phase to greater than 47.6 mass percent; and control of the methyl acetate concentration in the liquid-liquid separation step feed liquid to greater than 38.2 mass percent.

Relating to the condition (b'-v), the MA partition coefficient is 0.8 or less (for example, 0.15 to 0.80), preferably 0.7 or less (for example, 0.20 to 0.70), more preferably 0.6 or less (for example, 0.20 to 0.60), furthermore preferably 0.44 or less (for example, 0.20 to 0.44), and particularly preferably less than 0.25 (for example, from 0.20 to less than 0.25). The distribution ratio of methyl acetate (MA) between the aqueous phase and the organic phase varies depending on the temperature and the chemical compositions (including not only water and methyl iodide, but also other components such as acetic acid), and can therefore also serve as an index for control of the acetaldehyde partition coefficient.

In the acetic acid production methods according to the embodiment of the present invention, the liquid-liquid separation step has only to meet at least one of the conditions (b'-i) to (b'-v), but may meet two or more of the conditions together. Examples of combinations of two or more of the conditions which are preferably met together include the combinations of: (b'-i) and (b'-ii); (b'-i) and (b'-iii); (b'-i) and (b'-iv); (b'-i) and (b'-v); (b'-ii) and (b'-iii); (b'-ii) and (b'-iv); (b'-ii) and (b'-v); (b'-iii) and (b'-iv); (b'-iii) and (b'-v); (b'-iv) and (b'-v); (b'-i), (b'-ii), and (b'-iii); (b'-i), (b'-ii), and (b'-iv); (b'-i), (b'-ii), and (b'-v); (b'-i), (b'-iii), and (b'-iv); (b'-i), (b'-iii), and (b'-v); (b'-i), (b'-iv), and (b'-v); (b'-ii), (b'-iii), and (b'-iv); (b'-ii), (b'-iii), and (b'-v); (b'-ii), (b'-iv), and (b'-v); (b'-iii), (b'-iv), and (b'-v); (b'-i), (b'-ii), (b'-iii), and (b'-iv); (b'-i), (b'-ii), (b'-iii), and (b'-v); (b'-i), (b'-iii), (b'-iv), and (b'-v); (b'-ii), (b'-iii), (b'-iv), and (b'-v); and (b'-i), (b'-ii), (b'-iii), (b'-iv), and (b'-v). Among them, the liquid-liquid separation step particularly preferably meets at least the conditions (b'-i), (b'-ii), and (b'-iii) together, or at least the conditions (b'-i), (b'-ii), (b'-iii), and (b'-iv) together, or all the conditions (b'-i), (b'-ii), (b'-iii), (b'-iv), and (b'-v) together.

The acetaldehyde concentrations and the methyl acetate concentrations in the aqueous phase and the organic phase depend on the chemical composition of the liquid-liquid separation step feed liquid, and the temperature in liquid-liquid separation. With an increasing acetaldehyde concentration in the liquid-liquid separation step feed liquid, the acetaldehyde concentrations in the aqueous phase and the organic phase increase. With an increasing methyl acetate concentration in the liquid-liquid separation step feed liquid, the methyl acetate concentrations in the aqueous phase and the organic phase increase. As demonstrated in the experimental examples, the distribution ratio of acetaldehyde to the organic phase becomes relatively higher with an elevating temperature in the liquid-liquid separation. The acetaldehyde concentration and methyl acetate concentration in the liquid-liquid separation step feed liquid can be controlled typically by one or more of reaction conditions in the reactor 1, evaporation conditions in the evaporator 2, and distillation conditions in the distillation column 3. In general, the acetaldehyde concentration and the methyl acetate concentration in the liquid-liquid separation step feed liquid increase respectively with an increasing acetaldehyde concentration and with an increasing methyl acetate concentration in the reaction mixture. The acetaldehyde concentration in the reaction mixture tends to increase with each of increasing (elevating) reaction temperature, hydrogen partial pressure, methyl iodide concentration, water concentration, catalyst concentration, and lithium iodide concentration in the reaction system; and tends to decrease with each of increasing carbon monoxide (CO) partial pressure and methyl acetate concentration in the reaction system (see JP-A No. 2006-182691). In addition, the methyl acetate concentration in the reaction mixture increases with each of increasing acetic acid concentration and methanol concentration in the reaction system; and decreases with an increasing water concentration in the reaction system. This is because methyl acetate is formed through esterification between acetic acid and methanol. Thus, regulation of reaction conditions in the reactor, and operation conditions in the evaporation step and the distillation step, which steps are performed prior to the liquid-liquid separation step, can adjust the chemical composition of the liquid-liquid separation step feed liquid, and consequently, can adjust the acetaldehyde concentrations and the methyl acetate concentrations in the aqueous phase and the organic phase.

The methyl acetate concentration in the light ends column charge is controlled or adjusted by controlling the methyl acetate concentration in the reactor. For example, assume that methanol and carbon monoxide (CO) are charged into the reactor in constant amounts (at constant rates). In this case, the methyl acetate concentration in the reactor can be adjusted by increasing or decreasing one or more of factors that affect the reaction rate. Non-limiting examples of the factors include, each in the reactor, inside temperature, rhodium complex (Rh) quantity, methyl iodide (MeI) quantity, $H_2O$ quantity, hydrogen partial pressure, carbon monoxide partial pressure, and lithium iodide (LiI) quantity. Specifically, the methyl acetate concentration in the reactor is decreased by increasing one or more of the factors such as temperature, Rh concentration, MeI concentration, $H_2O$ concentration, hydrogen partial pressure, carbon monoxide partial pressure, and LiI concentration; and is increased by decreasing one or more of these factors. In contrast, assume that these conditions (factors) are set constant, namely the conditions such as temperature, Rh quantity, MeI quantity, $H_2O$ quantity, hydrogen partial pressure, carbon monoxide partial pressure, and LiI quantity are set constant. In this case, the methyl acetate concentration is increased by increasing the charge amounts of methanol and CO; and is decreased by decreasing the charge amounts of these components. The methyl acetate concentration in the vapors (light ends column charge) varies in proportion to the methyl acetate concentration in the liquid reaction mixture, where the light ends column charge results from evaporation of the liquid reaction mixture by the working of the evaporator. This is because the evaporator is operated at a constant (predetermined) evaporation rate. When the evaporator is heated or cooled, the evaporation rate varies, and this causes the methyl acetate concentration to vary. For example, when the evaporator is heated, the acetic acid concentration increases, and the methyl acetate concentration decreases in the evaporator vapors. In contrast, when the evaporator is cooled, an inverse phenomenon occurs. Namely, the acetic acid concentration decreases, and the methyl acetate concentration increases in the evaporator vapors.

In the acetaldehyde-removing step using the acetaldehyde-removing system 9, acetaldehyde derived from the process stream including water, acetic acid (AC), methyl iodide (MeI), and acetaldehyde (AD) is separated and removed. Acetaldehyde can be removed by a known technique, such as distillation, or extraction, or both in combination. The separated acetaldehyde is discharged through the line 53 out of the equipment. Useful components (such as methyl iodide) contained in at least one of the organic phase and the aqueous phase are recycled through the lines 52 and 23 to the reactor 1.

In the embodiment, of the aqueous phase, a part is refluxed through the line 29 to the distillation column 3; and another part is introduced and recycled through the lines 29, 30, and 23 to the reactor 1. A part of the organic phase is introduced and recycled through the lines 31 and 23 to the reactor 1. Another part of the organic phase and/or another part of the aqueous phase is introduced through the lines 31 and 50, and/or the lines 30 and 51 into the acetaldehyde-removing system 9. In addition to, or instead of refluxing of the aqueous phase, a part of the organic phase may be refluxed to the distillation column 3.

A reflux ratio at the distillation column 3 will be described below. Assume that the aqueous phase alone is refluxed to the distillation column 3, where the aqueous phase is of the condensates derived from the overhead stream (first overhead stream). In this case, the reflux ratio for the aqueous phase is desirably controlled to typically 2 or more, preferably 3 or more, more preferably 4 or more, furthermore preferably 8 or more, and particularly preferably 10 or more, where the reflux ratio for the aqueous phase is the ratio of the aqueous phase reflux amount to the aqueous phase distillate amount. Also assume that the organic phase alone of the condensates derived from the overhead stream is refluxed to the distillation column 3. In this case, the reflux ratio for the organic phase is desirably controlled to typically 1 or more, preferably 1.5 or more, more preferably 2 or more, furthermore preferably 4 or more, and particularly preferably 5 or more, where the reflux ratio for the organic phase is the ratio of the organic phase reflux amount to the organic phase distillate amount. Assume that both the aqueous phase and the organic phase of the condensates derived from the overhead stream are refluxed to the distillation column 3. In this case, the total reflux ratio for the aqueous phase and the organic phase is desirably controlled to typically 1.5 or more, preferably 2.3 or more, more preferably 3 or more, furthermore preferably 6 or more, and particularly preferably 7.5 or more, where the total reflux ratio is the ratio of the totality of the reflux amounts of the aqueous phase and the organic phase to the totality of the distillate amounts of the aqueous phase and the organic phase. When the aqueous phase is refluxed to the distillation column 3, the reflux ratio for the aqueous phase is preferably 2 or more, more preferably 3 or more, furthermore preferably 5 or more, particularly preferably 8 or more, and especially preferably 12 or more, where the reflux ratio for the aqueous phase is the ratio of the aqueous phase reflux amount to the aqueous phase distillate amount. When the reflux ratio at the after-mentioned distillation column 5 is controlled to 0.1 or more (in particular, 0.3 or more, preferably 0.32 or more), the reflux ratio at the distillation column 3 may be typically 0.5 or more, regardless of whichever of the upper phase and the lower phase is refluxed. In any case, the upper limit of the reflux ratio at the distillation column 3 may be typically 3000 (in particular, 1000), or may be 100 (in particular, 30). At a higher reflux ratio at the distillation column 3, crotonaldehyde is more concentrated at the column top of the distillation column 3, because crotonaldehyde has a lower boiling point (104° C.) than the boiling point (117° C.) of acetic acid. This allows the first acetic acid stream, which is obtained typically as a side stream, to have a lower crotonaldehyde concentration. Assume that crotonaldehyde is concentrated in the first overhead stream by the increase in reflux ratio at the distillation column 3, and the condensate (at least one of the aqueous phase and the organic phase) derived from this first overhead stream is recycled to the reactor 1. In this case, crotonaldehyde in the reactor reacts with acetaldehyde to form 2-ethylcrotonaldehyde. Crotonaldehyde in the reactor 1 also reacts with hydrogen to form butyl alcohol, and the butyl alcohol in turn reacts with acetic acid to form butyl acetate. As compared with crotonaldehyde, 2-ethylcrotonaldehyde less affects the potassium permanganate test result, and butyl acetate does not approximately affect the potassium permanganate test result. Thus, acetic acid tends to have still better quality. With a higher reflux ratio at the distillation column 3, 2-ethylcrotonaldehyde and butyl acetate tend to be present in lower concentrations at the column top and to be concentrated at bottoms and/or in sidecuts at height levels higher than the feeding level of the charge liquid to the distillation column 3, because 2-ethylcrotonaldehyde and butyl acetate have boiling points respectively of 137° C. and 126° C., higher than the boiling point (117° C.) of acetic acid.

In the embodiment, a part of the organic phase is introduced through the lines 31, 50, and 58 into the distillation column 10 (crotonaldehyde-removing column), from which crotonaldehyde is removed by distillation. The distillation may be performed continuously (as a continuous operation) or batchwise (as a batch treatment). Crotonaldehyde, when formed in a very small amount in the reaction system, is preferably removed batchwise (as a batch treatment) at the time point(s) when crotonaldehyde accumulates in a certain amount in at least one of the aqueous phase and the organic phase. This is preferred typically for energy cost saving. When crotonaldehyde removal is performed in a continuous operation, quality control and steam saving can be combined with each other by changing the throughput (charge amount (s)). The throughput at the distillation column 10 (crotonaldehyde-removing column) may be typically 0.0001 to 50 parts by mass (for example, 0.001 to 30 parts by mass), or may be 0.01 to 10 parts by mass (for example, 0.1 to 5 parts by mass), per 100 parts by mass of the charge amount at the distillation column 3 (first distillation column; light ends column). The distillation column 10 may be selected typically from rectification columns such as plate columns and packed columns. The distillation column 10 may have typically 1 to 100, preferably 2 to 50, more preferably 4 to 30, and furthermore preferably 5 to 20 theoretical plates (for example, 6 to 15 theoretical plates). When the distillation is performed continuously, the feed liquid is preferably charged into the distillation column 10 at an intermediate level in a height direction of the distillation column (at a height level between the first lower plate from the column top and the first upper plate from the column bottom), but may be fed at a height level lower than the top by 20% to 80% (two-tenths to eight-tenths). If the feed liquid is charged at an excessively low height level, methyl iodide is lost in a larger amount. If the feed liquid is charged at an excessively high height level, crotonaldehyde (and alkanes) is removed in a smaller amount. The feed liquid (charge liquid) to the distillation column 10 has a crotonaldehyde concentration of generally 0.01 to 50 ppm by mass (for example, 0.1 to 50 ppm by mass), preferably 0.3 to 30 ppm by mass, more preferably 0.5 to 10 ppm by mass, and furthermore preferably 0.8 to 7.0 ppm by mass (for example, 1.0 to 5.0 ppm by mass). Overhead vapors from the distillation column 10 are introduced through the line 59 to the condenser 10a and are condensed to give condensates. Of the condensates, a part is refluxed through the line 61 to the distillation column 10, and the remainder is drawn as a distillate through the line 62. The distillate mainly includes methyl iodide and methyl acetate and also includes other components such as dimethyl ether and low-boiling alkanes. The distillate can be recycled typically to at least one of the decanter 4 and the reactor 1. Of the overhead vapors, gas components which are not condensed in the condenser 10a are fed through the line 63 typically to the scrubbing system 8. Bottoms are drawn from the column bottom of the distillation column 10 through the line 60. The bottoms mainly include high-boiling impurities such as crotonaldehyde, 2-ethylcrotonaldehyde, butyl acetate, and alkanes; and acetic acid. The bottoms are generally discarded. Water contained in a trace amount in the organic phase may be concentrated at the column top, or may be drawn from the column bottom. In addition to, or instead of introduction of the organic phase into the distillation column 10, the aqueous phase may be introduced through the lines 30, 51, and 58 into the distillation column 10. In this case, at the distillation column 10, a distillate including water is obtained from the column top, and bottoms including crotonaldehyde and other high-boiling impurities, and acetic acid are obtained from the column bottom. As described above, the treatment of at least one of the aqueous phase and the organic phase in the distillation column 10 enables efficient removal of crotonaldehyde, and this allows the acetic acid product to yield a better potassium permanganate test result, and leads to elimination or downsizing of large-scale facilities such as ozone treatment facilities, and to reduction in steam cost and electric utility expense. The reflux ratio at the distillation column 10 is typically 0.01 or more, preferably 0.05 or more, more preferably 0.5 or more, furthermore preferably 5 or more, and particularly preferably 20 or more (for example, 30 or more), where the reflux ratio is the ratio of the reflux amount to the distillate amount. The upper limit of the reflux ratio at the distillation column 10 is typically 1000 (or 100). With an excessively high reflux ratio at the distillation column 10, crotonaldehyde, which would be concentrated at the column bottom, is concentrated at the column top contrarily, and this causes acetic acid, which has a higher boiling point, to be concentrated in a higher concentration at the column top. To eliminate or minimize this, the reflux ratio at the distillation column 10 is preferably controlled to 100 or less. As crotonaldehyde is drawn from the column bottom, at the distillation column 10, the ratio of the crotonaldehyde concentration (ppm by mass) in the distillate to the crotonaldehyde concentration (ppm by mass) in the charge liquid is typically less than 1, preferably 0.95 or less, more preferably 0.80 or less, furthermore preferably 0.70 or less, and particularly preferably 0.60 or less (for example, 0.50 or less, especially preferably 0.30 or less, and particularly 0.20 or less). Also at the distillation column 10, the ratio of the crotonaldehyde concentration (ppm by mass) in the bottoms to the crotonaldehyde concentration (ppm by mass) in the charge liquid is typically greater than 1, preferably 1.2 or more, more preferably 1.5 or more, furthermore preferably 2.0 or more, particularly preferably 3.0 or more (for example, 4.0 or more, especially preferably 5.0 or more), and still especially preferably 10 or more (for example, 20 or more).

In a preferred embodiment, the acetaldehyde-removing step using the acetaldehyde-removing system 9 removes acetaldehyde from at least one of the organic phase and the aqueous phase by a known technique such as distillation, or extraction, or both in combination. The separated acetaldehyde is discharged through the line 53 out of the equipment. Useful components (such as methyl iodide) contained in at least one of the organic phase and the aqueous phase are recycled through the lines 52 and 23 to the reactor 1.

FIG. 2 is a schematic flow chart illustrating an acetaldehyde-removing system according to an embodiment. For example, assume that the organic phase is treated in the acetaldehyde-removing step according to the flow. In this case, the organic phase is treated typically by a procedure as follows. The organic phase is fed through a line 101 to a distillation column (first acetaldehyde-removing column) 91 and is separated by distillation into an acetaldehyde-rich overhead stream (line 102), and a methyl iodide-rich residue stream (residual liquid stream; bottoms stream) (line 103). The overhead stream is condensed in a condenser 91a to give a condensate. Of the condensate, a part (line 104) is refluxed to a column top portion of the distillation column 91; and the remainder (line 105) is fed to an extraction column 92. The condensate fed to the extraction column 92 is extracted with water introduced from a line 109, to give an extract. The extract resulting from the extraction is fed through a line 107 to a distillation column (second acetaldehyde-removing column) 93 and is separated by distillation into an acetaldehyde-rich overhead stream (line 112) and a water-rich residue stream (line 113). The acetaldehyde-rich overhead stream is condensed in a condenser 93a to give a condensate. Of the condensate, a part (line 114) is refluxed to a column top portion of the distillation column 93; and the remainder (line 115) is discharged out of the system. The methyl iodide-rich residue stream as bottoms from the first acetaldehyde-removing column 91, a methyl iodide-rich raffinate (line 108) from the extraction column 92, and the water-rich residue stream as bottoms from the second acetaldehyde-removing column 93 are recycled respectively through the lines 103, 111, and 113 to the reactor 1, and/or to an appropriate site in the process. For example, the methyl iodide-rich raffinate from the extraction column 92 can be recycled through the line 110 to the distillation column 91. The liquid in the line 113 is generally discharged out as an effluent. Gases (lines 106 and 116), which have not been condensed in the condensers 91a and 93a, are subjected to absorptive treatments in the scrubbing system 8, or discarded.

Also assume that the aqueous phase is treated in the acetaldehyde-removing step according to the flow illustrated in FIG. 2. In this case, the aqueous phase is treated typically by a procedure as follows. The aqueous phase is fed through the line 101 to the distillation column (first acetaldehyde-removing column) 91, and is separated by distillation into an acetaldehyde-rich overhead stream (line 102) and a water-rich residue stream (line 103). The overhead stream is condensed in the condenser 91a to give a condensate. Of the condensate, a part (line 104) is refluxed to the column top portion of the distillation column 91; and the remainder (line 105) is fed to the extraction column 92. The condensate fed to the extraction column 92 is extracted with water introduced from the line 109, to give an extract. The extract resulting from the extraction is fed through the line 107 to the distillation column (second acetaldehyde-removing column) 93, and is separated by distillation into an acetaldehyde-rich overhead stream (line 112) and a water-rich residue stream (line 113). The acetaldehyde-rich overhead stream is condensed in the condenser 93a to give a condensate. Of the condensate, a part (line 114) is refluxed to the column top portion of the distillation column 93; and the remainder (line 115) is discharged out of the system. The water-rich residue stream as bottoms from the first acetaldehyde-removing column 91, a methyl iodide-rich raffinate (line 108) from the extraction column 92, and the water-rich residue stream as bottoms from the second acetaldehyde-removing column 93 are recycled respectively through the lines 103, 111, and 113 to the reactor 1, and/or to an appropriate site in the process. For example, the methyl iodide-rich raffinate from the extraction column 92 can be recycled through the line 110 to the distillation column 91. The liquid in the line 113 is generally discharged out as an effluent. Gases (lines 106 and 116), which have not been condensed in the condensers 91a and 93a, are subjected to absorptive treatments in the scrubbing system 8, or discarded.

Instead of, or in addition to the technique, acetaldehyde derived from the process stream including water, acetic acid (AC), methyl iodide (MeI), and acetaldehyde (AD) can also be removed by utilizing extractive distillation. For example, acetaldehyde can be discharged out of the system by the following procedure. The process stream is liquid-liquid separated into an organic phase and an aqueous phase, and at least one of the organic phase and the aqueous phase is fed as a charge liquid to a distillation column (extractive distillation column). With this, an extractant (generally, water) is introduced into a concentrated zone in the distillation column, where the concentrated zone is a zone in which methyl iodide and acetaldehyde are concentrated, and is exemplified typically by space ranging from the column top to the charge liquid feeding level. A liquid (extract) falling down from the concentrated zone is drawn as a side stream (sidecut stream), the side stream is liquid-liquid separated into an aqueous phase and an organic phase, and the aqueous phase is subjected to distillation. Thus, acetaldehyde is discharged out of the system. When a relatively large amount of water is present in the distillation column, a liquid falling down from the concentrated zone may be drawn as a side stream without introduction of the extractant to the distillation column. For example, it is acceptable that this distillation column is provided with a unit (such as a chimney tray) capable of receiving the liquid (extract) falling down from the concentrated zone, and the liquid (extract) received by the unit is drawn as a side stream. The extractant is preferably introduced into a portion at a height level higher than the charge liquid feeding level and is more preferably introduced into a portion adjacent to the column top. The side stream is preferably drawn from a portion at a level lower than the extractant introducing level and higher than the charge liquid feeding level, where the levels are height levels at the distillation column. This technique enables high-concentration extraction of acetaldehyde with the extractant (generally, water) from the concentrate of methyl iodide and acetaldehyde. In addition, the technique enables efficient extraction of acetaldehyde with a small amount of the extractant, because of using, as an extraction zone, space between the extractant introducing level and the sidecut level. The technique can therefore significantly reduce the number of plates in the distillation column and can reduce the required steam amount, as compared typically with a technique of drawing an extract resulting from extractive distillation from a column bottom portion of a distillation column (extractive distillation column). Further, the technique enables removal of acetaldehyde under such conditions as to restrain or minimize the loss of methyl iodide out of the system, because the technique, as using a small amount of the extractant, can reduce the ratio (MeI/AD ratio) of methyl iodide to acetaldehyde in the aqueous extract as compared with the technique illustrated in FIG. 2, which employs acetaldehyde-removing distillation and aqueous extraction in combination. The acetaldehyde concentration in the side stream is significantly higher than the acetaldehyde concentrations in the charge liquid and in the bottoms (bottom liquid). The ratio of acetaldehyde to methyl iodide in the side stream is higher than the ratios of acetaldehyde to methyl iodide in the charge liquid and in the bottoms. An organic phase (methyl iodide phase) resulting from liquid-liquid separation of the side stream may be recycled to this distillation column. In this case, the organic phase resulting from liquid-liquid separation of the side stream is preferably recycled at a level lower than the side stream drawing level and higher than the charge liquid feeding level, where the levels are height levels at the distillation column. In addition, a miscible solvent may be introduced into the distillation column (extractive distillation column), where the miscible solvent is miscible with a component or components (such as methyl acetate) constituting the organic phase resulting from liquid-liquid separation of the process stream. Non-limiting examples of the miscible solvent include acetic acid and ethyl acetate. The miscible solvent is preferably introduced at a level lower than the side stream drawing level and higher than the charge liquid feeding level, where the levels are height levels at the distillation column. When the organic phase resulting from liquid-liquid separation of the side stream is recycled to this distillation column, the miscible solvent is preferably introduced at a height level lower the organic phase recycling level. Recycling of the organic phase resulting from liquid-liquid separation of the side stream to the distillation column and/or the introduction of the miscible solvent to the distillation column can lower the methyl acetate concentration in the extract drawn as the side stream, can lower the methyl acetate concentration in an aqueous phase resulting from liquid-liquid separation of the extract, and, consequently, can restrain or minimize the contamination of the aqueous phase with methyl iodide.

The distillation column (extractive distillation column) has typically 1 to 100, preferably 2 to 50, furthermore preferably 3 to 30, and particularly preferably 5 to 20 theoretical plates. Thus, the distillation column according to the technique enables efficient separation and removal of acetaldehyde with a smaller number of plates (theoretical plates), as compared with the number of plates (80 to 100 theoretical plates) in distillation columns and extractive distillation columns for use in conventional acetaldehyde removal. The ratio by mass of the flow rate of the extractant to the flow rate of the charge liquid may be selected within the range of from 0.0001:100 to 100:100, but is generally from 0.0001:100 to 20:100, preferably from 0.001:100 to 10:100, more preferably from 0.01:100 to 8:100, and furthermore preferably from 0.1:100 to 5:100, where the charge liquid is at least one of the organic phase and the aqueous phase resulting from liquid-liquid separation of the process stream. At the distillation column (extractive distillation column), the column top temperature is typically 15° C. to 120° C., preferably 20° C. to 90° C., more preferably 20° C. to 80° C., and furthermore preferably 25° C. to 70° C.; and the column top pressure is typically about 0.1 to about 0.5 MPa (absolute pressure). Other conditions for the distillation column (extractive distillation column) may be as with conditions for distillation columns and extractive distillation columns for use in conventional acetaldehyde removal.

FIG. 3 is a schematic flow chart illustrating an acetaldehyde-removing system using the extractive distillation according to an embodiment. In this embodiment, at least one of the organic phase and the aqueous phase resulting from liquid-liquid separation of the process stream is fed as a charge liquid through a feed line 201 to an intermediate plate (at a height level between the column top and the column bottom) of a distillation column 94, and water is introduced through a line 202 into a portion adjacent to the column top. Thus, extractive distillation is performed in the distillation column 94 (extractive distillation column). The distillation column 94 is provided with a chimney tray 200 at a height level higher than the charge liquid feeding level, where the chimney tray 200 is capable of receiving a liquid (extract) falling down from a concentrated zone in the column, and where methyl iodide and acetaldehyde are concentrated in the concentrated zone. In this extractive distillation, a liquid on the chimney tray 200 is drawn, preferably in the whole quantity, through a line 208 and introduced into, and liquid-liquid separated in a decanter 95 to give an aqueous phase and an organic phase. The aqueous phase (including acetaldehyde) is fed from the decanter 95 through a line 212 and introduced into and cooled in a cooler 95*a*. Thus, methyl iodide dissolved in the aqueous phase is two-phase separated, followed by liquid-liquid separation in a decanter 96 to give an aqueous phase and an organic phase. The aqueous phase is fed from the decanter 96 through a line 216 to a distillation column 97 (acetaldehyde-removing column) for distillation. Vapors from the column top are fed through a line 217 and introduced into and condensed in a condenser 97*a* to give a condensate (mainly including acetaldehyde and methyl iodide). Of the condensate, a part is refluxed to the column top of the distillation column 97; and the remainder is discarded, or fed through a line 220 to a distillation column 98 (extractive distillation column). Water is introduced through a line 222 into the distillation column 98 at a portion adjacent to the column top, to perform extractive distillation. Vapors from the column top are brought through a line 223 into a condenser 98*a* and are condensed therein to give a condensate (mainly including methyl iodide). Of the condensate, a part is refluxed to the column top portion; and the remainder is recycled through a line 226 to the reaction system, or may be removed (discharged) out of the system. The organic phase (methyl iodide phase) from the decanter 95 is recycled, preferably in the whole quantity, through lines 209 and 210 to the distillation column 94 at a height level lower than the level of the chimney tray 200. A part of the aqueous phase from the decanter 95, and the organic phase from the decanter 96 are recycled respectively through lines 213 and 210 and through lines 214 and 210 to the distillation column 94, but this recycling is not necessarily performed. A part of the aqueous phase from the decanter 95 may be used as the extractant (water) in the distillation column 94. A part of the aqueous phase from the decanter 96 may be recycled through the line 210 to the distillation column 94. In some cases (for example, in the case where the charge liquid includes methyl acetate), the distillation efficiency can be improved by charging a miscible solvent through a line 215 to the distillation column 94, where the miscible solvent is miscible with a component or components (such as methyl acetate) constituting the organic phase resulting from liquid-liquid separation of the process stream, and where the miscible solvent herein is exemplified by acetic acid and ethyl acetate. The miscible solvent is fed to the distillation column 94 at a height level higher than the charge liquid feeding level (line 201 coupling level) and lower than the recycle line 210 coupling level. Bottoms from the distillation column 94 are recycled to the reaction system. Vapors from the column top of the distillation column 94 are fed through a line 203 and brought into and condensed in a condenser 94a to give a condensate, and the condensate is liquid-liquid separated in a decanter 99 into an aqueous phase and an organic phase. The organic phase is refluxed through a line 206 to the column top portion of the distillation column 94, and the aqueous phase is brought through a line 207 to the decanter 95. Bottoms (containing water as a principal component) from the distillation column 97 and bottoms (water containing a small amount of acetaldehyde) from the distillation column 98 (extractive distillation column) are transferred respectively through lines 218 and 224 and removed from the system, or recycled to the reaction system. Gases (lines 211, 221, and 227), which have not been condensed in the condensers 94a, 97a, and 98a, are each subjected to an absorption treatment in the scrubbing system 8, or discarded.

FIG. 4 is a schematic flow chart illustrating an acetaldehyde-removing system using the extractive distillation, according to another embodiment. In this embodiment, the condensate derived from the vapors from the column top of the distillation column 94 is brought into a hold tank 100, and the whole quantity of the vapor condensate is refluxed through a line 206 to a column top portion of the distillation column 94. The other configurations than this are as in the embodiment illustrated in FIG. 3.

FIG. 5 is a schematic flow chart illustrating an acetaldehyde-removing system using the extractive distillation, according to yet another embodiment. In this embodiment, the whole quantity of the liquid on the chimney tray 200 is drawn, introduced through the line 208 directly to the cooler 95a without passing through the decanter 95, and cooled in the cooler 95a and fed to the decanter 96. The other configurations than this are as in the embodiment illustrated in FIG. 4.

Referring back to FIG. 1, the gases formed by the working of the condenser 3a typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gases are fed from the condenser 3a through the lines 32 and 15 to the scrubbing system 8. Of the gases that reach the scrubbing system 8, components such as methyl iodide, hydrogen iodide, water, methyl acetate, acetic acid, dimethyl ether, methanol, acetaldehyde, and formic acid are absorbed by the absorbing liquid in the scrubbing system 8. Hydrogen iodide reacts with methanol or methyl acetate in the absorbing liquid to form methyl iodide. The resulting liquid containing useful components such as the methyl iodide is recycled from the scrubbing system 8 through the recycle lines 48 and 23 to the reactor 1.

The bottoms drawn from the column bottom portion of the distillation column 3 include larger amounts of heavy ends as compared with the overhead stream and the side stream from the distillation column 3, and typically include propionic acid, as well as the catalyst and the promoter as being entrained, where heavy ends herein are components having higher boiling points as compared with acetic acid. The bottoms also include acetic acid, methyl iodide, methyl acetate, and water. In the embodiment, of the bottoms as above, a part is continuously introduced through the lines 25 and 26 to the evaporator 2; and another part is continuously introduced and recycled through the lines 25 and 23 to the reactor 1.

In a preferred embodiment, the bottoms drawn from the column bottom portion of the distillation column 3 include larger amounts of heavy ends as compared with the overhead stream and the side stream from the distillation column 3 and typically include propionic acid, as well as the catalyst and the promoter as being entrained, where the heavy ends are components having higher boiling points as compared with acetic acid. The bottoms also include other components such as acetic acid, methyl iodide, methyl acetate, crotonaldehyde, 2-ethylcrotonaldehyde, butyl acetate, and water. In this embodiment, of the bottoms as above, a part is continuously introduced and recycled through the lines 25 and 26 to the evaporator 2; and another part is continuously introduced and recycled through the lines 25 and 23 to the reactor 1.

The first acetic acid stream, which is continuously drawn as a side stream from the distillation column 3, is enriched with acetic acid as compared with the vapor stream continuously introduced into the distillation column 3. Specifically, the acetic acid concentration in the first acetic acid stream is higher than the acetic acid concentration in the vapor stream. The acetic acid concentration in the first acetic acid stream is typically 90 to 99.9 mass percent, and preferably 93 to 99 mass percent. In addition to acetic acid, the first acetic acid stream may include other components such as methyl iodide, hydrogen iodide, water, methyl acetate, dimethyl ether, methanol, acetaldehyde, formic acid, and propionic acid. The first acetic acid stream has a methyl iodide concentration of typically 8 mass percent or less (for example, 0.1 to 8 mass percent), and preferably 0.2 to 5 mass percent; a water concentration of typically 8 mass percent or less (for example, 0.1 to 8 mass percent), and preferably 0.2 to 5 mass percent; and a methyl acetate concentration of typically 8 mass percent or less (for example, 0.1 to 8 mass percent), and preferably 0.2 to 5 mass percent. The line 27 may be coupled to the distillation column 3 at a level lower than the level at which the line 21 is coupled to the distillation column 3, as illustrated in FIG. 1, but may be coupled at a level lower than or equal to the level at which the line 21 is coupled to the distillation column 3, where the levels are height levels at the distillation column 3. The first acetic acid stream from the distillation column 3 is introduced through the line 27 to the subsequent (downstream) distillation column 5 continuously at a predetermined flow rate. The first acetic acid stream, which is drawn as the side stream from the distillation column 3, and/or the bottoms from the distillation column 3 or a condensate of vapors from the column bottom portion of the distillation column 3 may serve as an acetic acid product without further treatment, or may be continuously introduced directly into the distillation column 6 without passing through the distillation column 5.

In a preferred embodiment, the first acetic acid stream, which is continuously drawn as a side stream from the distillation column 3, is enriched with acetic acid as compared with the vapor stream continuously introduced into the distillation column 3. Specifically, the acetic acid concentration in the first acetic acid stream is higher than the acetic acid concentration in the vapor stream. The acetic acid concentration in the first acetic acid stream is typically 90 to 99.9 mass percent, and preferably 93 to 99 mass percent. The first acetic acid stream includes not only acetic acid, but also other components such as methyl iodide, hydrogen iodide, water, methyl acetate, dimethyl ether, methanol, acetaldehyde, crotonaldehyde, 2-ethylcrotonaldehyde, butyl acetate, formic acid, and propionic acid, as well as alkyl iodides such as ethyl iodide, propyl iodide, butyl iodide, hexyl iodide, and decyl iodide. The first acetic acid stream has a methyl iodide concentration of typically 0.1 to 8 mass percent, and preferably 0.2 to 5 mass percent; a water concentration of typically 0.1 to 8 mass percent, and preferably 0.2 to 5 mass percent; and a methyl acetate concentration of typically 0.1 to 8 mass percent, and preferably 0.2 to 5 mass percent.

In the embodiment of the present invention, the crotonaldehyde concentration in the first acetic acid stream is controlled to 2.2 ppm by mass or less. This allows the second acetic acid stream to have a lower crotonaldehyde concentration and to yield a better potassium permanganate test result, where the second acetic acid stream results from separation and removal of water by the dehydration step. This can downsize or eliminate acetaldehyde-removing facilities and ozone treatment facilities, which are conventionally used for better potassium permanganate test results. In addition, acetic acid yielding a good potassium permanganate test result can be obtained simply through the light ends column and the dehydration column, and this can downsize or eliminate downstream facilities such as a heavy ends column and a product column (finishing column). The crotonaldehyde concentration in the first acetic acid stream is preferably 2.0 ppm by mass or less, more preferably 1.8 ppm by mass or less, furthermore preferably 1.5 ppm by mass or less, and particularly preferably 1.2 ppm by mass or less (for example, 1.0 ppm by mass or less, or 0.8 ppm by mass or less, and especially preferably 0.5 ppm by mass or less). Assume that the reflux ratio at the distillation column 5 is controlled to 0.1 or more (in particular, 0.3 or more, and preferably 0.32 or more). In this case, the crotonaldehyde concentration in the first acetic acid stream is not limited within the range, and may be typically 5 ppm by mass or less (in particular, 2.5 ppm by mass or less), but preferably falls within the range.

The first acetic acid stream has an 2-ethylcrotonaldehyde concentration of typically 3.0 ppm by mass or less, preferably 2.0 ppm by mass or less, more preferably 1.0 ppm by mass or less, and furthermore preferably 0.8 ppm by mass or less (for example, 0.5 ppm by mass or less). The first acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less, preferably 35 or less, more preferably 25 or less, furthermore preferably 20 or less, and particularly preferably 15 or less. The lower limit of the ratio may be typically 0.5, 0.3, 0.1, 0.05, or 0.01. In the present invention, the crotonaldehyde concentration and the 2-ethylcrotonaldehyde concentration in the first acetic acid stream may be controlled together, to regulate the ratio ($C_{CR}/C_{ECR}$) of the crotonaldehyde concentration $C_{CR}$ (ppm by mass) to the 2-ethylcrotonaldehyde concentration $C_{ECR}$ (ppm by mass). Specifically, it is acceptable that, by efficient separation in the separation step using the difference in boiling point from acetic acid, crotonaldehyde is concentrated in the overhead condensate from the light ends column (first distillation column); and thereby the crotonaldehyde concentration is lowered, and the 2-ethylcrotonaldehyde concentration is regulated in the first acetic acid stream, where the first acetic acid stream is obtained as a side stream or bottoms stream from the light ends column. Thus, both the crotonaldehyde concentration and the 2-ethylcrotonaldehyde concentration in the first acetic acid stream can be controlled together. With a decreasing ratio ($C_{CR}/C_{ECR}$), the acetic acid product tends to yield a better potassium permanganate test result, because crotonaldehyde more adversely affects the potassium permanganate test result as compared with 2-ethylcrotonaldehyde.

The first acetic acid stream has a butyl acetate concentration of typically 15 ppm by mass or less, preferably 12 ppm by mass or less, more preferably 10 ppm by mass or less, and furthermore preferably 8 ppm by mass or less. The lower limit of the butyl acetate concentration in the first acetic acid stream is typically 0 ppm by mass (or 0.1 ppm by mass). The first acetic acid stream has a ratio ($C_{CR}/C_{BA}$) of the crotonaldehyde concentration $C_{CR}$ (ppm by mass) to the butyl acetate concentration $C_{EA}$ (ppm by mass) of typically 2.0 or less, preferably 1.5 or less, more preferably 1.0 or less, and furthermore preferably 0.6 or less. The lower limit of the ratio may be typically 0.1, 0.05, 0.02, 0.01, or 0.001. With a decreasing ratio ($C_{CR}/C_{BA}$), the acetic acid product tends to yield a better potassium permanganate test result, because butyl acetate is approximately harmless to the potassium permanganate test.

In addition, according to the present invention, the reflux ratio at the first distillation column is controlled to a specific level or higher, and this causes crotonaldehyde to be concentrated in a column top portion of the distillation column; and allows the first acetic acid stream to have a lower crotonaldehyde concentration, where the first acetic acid stream is drawn as a side stream from the first distillation column. The first acetic acid stream has a crotonaldehyde concentration of typically 1.3 ppm by mass or less, preferably 1.0 ppm by mass or less, more preferably 0.85 ppm by mass or less, and particularly preferably 0.5 ppm by mass or less (for example, 0.25 ppm by mass or less). Control of the crotonaldehyde concentration in the first acetic acid stream to 1.3 ppm by mass or less allows the after-mentioned second acetic acid stream to have a significantly lower crotonaldehyde concentration and to yield a significantly better potassium permanganate test result. The lower limit of the crotonaldehyde concentration in the first acetic acid stream may be 0 ppm by mass, or may be typically 0.01 ppm by mass (or 0.10 ppm by mass). The first acetic acid stream has a 2-ethylcrotonaldehyde concentration of typically 1.0 ppm by mass or less, and preferably 0.50 ppm by mass or less. Control of the 2-ethylcrotonaldehyde concentration in the first acetic acid stream to 1.0 ppm by mass or less allows the second acetic acid stream to yield a still better potassium permanganate test result. The lower limit of the 2-ethylcrotonaldehyde concentration in the first acetic acid stream may be typically 0 ppm by mass, or 0.01 ppm by mass (or 0.10 ppm by mass). The first acetic acid stream has a butyl acetate concentration of typically 15 ppm by mass or less, preferably 10 ppm by mass or less, more preferably 8 ppm by mass or less, and particularly preferably 5 ppm by mass or less (for example, 3 ppm by mass or less). Control of the butyl acetate concentration in the first acetic acid stream to 15 ppm by mass or less allows the second acetic acid stream to have a higher purity. The lower limit of the butyl acetate Concentration in the first acetic acid stream may be typically 0 ppm by mass, or 0.1 ppm by mass (for example, 0.3 ppm by mass or 1.0 ppm by mass).

In a preferred embodiment, the line 27 may be coupled to the distillation column 3 at a level higher than the coupling level of the line 21 as illustrated in the figure, but may also be coupled at a level lower than, or equal to the coupling level of the line 21 to the distillation column 3, where the levels are height levels at the distillation column 3. The first acetic acid stream from the distillation column 3 is introduced through the line 27 into the subsequent (downstream) distillation column 5 continuously at a predetermined flow rate. The line 27 and the distillation column 5 (at least portions that are to be in contact with a liquid and/or a gas) may be made of stainless steel, but are preferably made of a material selected from highly corrosion-resistant metals such as nickel-base alloys and zirconium, so as to restrain corrosion of the interior of the piping, where the corrosion will be caused by hydrogen iodide and/or acetic acid.

In a preferred embodiment, the bottoms drawn from the column bottom portion of the distillation column 3, or the first acetic acid stream drawn as a side stream from the distillation column 3 may also serve as an acetic acid product without further treatment, as long as its quality is acceptable.

Potassium hydroxide may be fed or added through the line 55 (potassium hydroxide introducing line) to the first acetic acid stream passing through the line 27. The potassium hydroxide may be fed or added typically as a solution such as an aqueous solution. The feeding or addition of potassium hydroxide to the first acetic acid stream can decrease hydrogen iodide in the first acetic acid stream. Specifically, hydrogen iodide reacts with potassium hydroxide to give potassium iodide and water. This can decrease hydrogen iodide-induced corrosion of the equipment such as distillation columns. In this process, potassium hydroxide can be fed or added to an appropriate site where hydrogen iodide is present. The potassium hydroxide added in the process also reacts with acetic acid to give potassium acetate.

The distillation column 5 is a unit with which the second distillation step is performed. The distillation column 5 in the embodiment is characterized as a so-called dehydration column. The second distillation step is the step of subjecting the first acetic acid stream, which is continuously introduced into the distillation column 5, to a distillation treatment to further purify acetic acid. The distillation column 5 (at least portions that are to be in contact with a liquid and/or a gas) is preferably made of a material selected from nickel-base alloys and zirconium. The use of the material as above can restrain or minimize corrosion of the interior of the distillation column and can restrain dissolution of corrodible metal ions, where the corrosion will be caused by hydrogen iodide and/or acetic acid.

The charge liquid to the distillation column 5 includes at least a part of the first acetic acid stream (line 27) and may further include one or more streams other than the first acetic acid stream, where non-limiting examples of the other streams include streams recycled from downstream steps, such as a stream from the line 42.

The distillation column 5 may be selected typically from rectification columns such as plate columns and packed columns. A plate column, when employed as the distillation column 5, typically has 5 to 50 theoretical plates. In an embodiment of the present invention, the reflux ratio at the distillation column 5 is controlled to 0.1 or more (in particular, 0.3 or more, and preferably 0.32 or more). Control of the reflux ratio at the distillation column 5 to 0.1 or more (in particular, 0.3 or more, and preferably 0.32 or more) allows crotonaldehyde flowing into the dehydration column to be concentrated at the column top, because crotonaldehyde has a lower boiling point as compared with acetic acid. This allows the second acetic acid stream to have a significantly lower crotonaldehyde concentration, where the second acetic acid stream is obtained as a side stream or bottoms stream from the distillation column 5. When the overhead stream (second overhead stream) containing such concentrated crotonaldehyde is recycled from the column top of the distillation column 5 to the reactor 1, the crotonaldehyde is converted into 2-ethylcrotonaldehyde and butyl acetate, and this allows acetic acid to have still better quality, because 2-ethylcrotonaldehyde and butyl acetate are respectively less harmful and approximately harmless to the potassium permanganate test result, as described above.

The reflux ratio at the distillation column 5 is preferably 0.1 or more (in particular, 0.3 or more, for example, 0.32 or more), more preferably 0.35 or more, furthermore preferably 0.4 or more, particularly preferably 1 or more, and especially preferably 2 or more. When the crotonaldehyde concentration in the first acetic acid stream is controlled to 2.2 ppm by mass or less, the reflux ratio at the distillation column 5 may be typically 0.1 or more (for example, 0.2 or more, in particular, 0.3 or more, and typically 0.32 or more). The upper limit of the reflux ratio at the distillation column 5 is typically 3000 (in particular, 1000), and may be about 100 or about 10.

In a preferred embodiment, the reflux ratio at the distillation column 5 is typically 0.1 or more (in particular, 0.3 or more, typically 0.32 or more), preferably 1.0 or more, more preferably 5.0 or more, and furthermore preferably 10 or more (for example, 12 or more). The upper limit of the reflux ratio at the distillation column 5 may be typically about 3000 (or about 1000), or about 200 (or about 100). Control of the reflux ratio at the distillation column 5 to 0.1 or more (in particular, 0.3 or more, and preferably 0.32 or more) allows crotonaldehyde flowing into the distillation column 5 to be concentrated at the column top, because crotonaldehyde has a lower boiling point as compared with acetic acid. This allows the second acetic acid stream to have a significantly lower crotonaldehyde concentration, where the second acetic acid stream is obtained as a side stream or bottoms stream from the distillation column 5. In addition, recycling of the overhead stream (second overhead stream) containing such concentrated crotonaldehyde from the column top of the distillation column 5 to the reactor 1 allows acetic acid to have still better quality, because the crotonaldehyde is converted into 2-ethylcrotonaldehyde and butyl acetate, which are respectively less harmful and approximately harmless to the potassium permanganate test result as compared with crotonaldehyde, as described above.

In the distillation column 5 during the second distillation step, the column top pressure is typically 0.01 to 0.50 MPa (gauge pressure), preferably 0.10 to 0.28 MPa (gauge pressure), more preferably 0.15 to 0.23 MPa (gauge pressure), and furthermore preferably 0.17 to 0.21 MPa (gauge pressure); and the column bottom pressure is higher than the column top pressure and is typically 0.13 to 0.31 MPa (gauge pressure), preferably 0.18 to 0.26 MPa (gauge pressure), and furthermore preferably 0.20 to 0.24 MPa (gauge pressure). In the distillation column 5 during the second distillation step, the column top temperature is preferably lower than 175° C. (and more preferably lower than 165° C.); and the column bottom temperature is preferably lower than 185° C. (and more preferably lower than 175° C.) Control of the column top temperature and the column bottom temperature in the distillation column 5 within the ranges can more restrain or minimize corrosion of the inside of the distillation column and can more restrain the dissolution of corrodible metal ions, where the corrosion will be caused by hydrogen iodide and/or acetic acid. The column top temperature is more preferably lower than 163° C., furthermore preferably lower than 161° C., particularly preferably lower than 160° C., and especially preferably lower than 155° C. The lower limit of the column top temperature is typically 110° C. The column bottom temperature is more preferably lower than 173° C., furthermore preferably lower than 171° C., and particularly preferably lower than 166° C. The lower limit of the column bottom temperature is typically 120° C.

In a preferred embodiment, the distillation column 5 is a unit with which the second distillation step is performed. The distillation column 5 in the embodiment is characterized as a so-called dehydration column. The second distillation step is the step of subjecting the first acetic acid stream, which is continuously introduced into the distillation column 5, to a distillation treatment so as to further purify acetic acid. The distillation column 5 may be selected typically from rectification columns such as plate columns and packed columns. A plate column, when employed as the distillation column 5, typically has 5 to 50 theoretical plates, and is operated at a reflux ratio of typically 0.2 to 3000, where the reflux ratio may be determined according to the number of theoretical plates. In the distillation column 5 during the second distillation step, the column top pressure is set typically to 150 to 250 kPa (gauge pressure); and the column bottom pressure is set higher than the column top pressure and is typically from 160 to 290 kPa (gauge pressure). In the distillation column 5 during the second distillation step, the column top temperature is typically set to a temperature which is higher than the boiling point of water and lower than the boiling point of acetic acid each at the set column top pressure and which is from 130° C. to 160° C.; and the column bottom temperature is typically set to a temperature which is equal to or higher than the boiling point of acetic acid at the set column bottom pressure and which is from 150° C. to 175° C.

At the distillation column 5, vapors as an overhead stream (second overhead stream) are continuously drawn from a column top portion to the line 33; and bottoms are continuously drawn from a column bottom portion to the line 34. There is disposed the reboiler 5b. A side stream (liquid or gas) may be continuously drawn from a portion of the distillation column 5 to the line 34, where the portion is at a height level between the column top portion and the column bottom portion.

The vapors drawn from the column top portion of the distillation column 5 include larger amounts of light ends as compared with the bottoms from the distillation column 5 and typically include methyl iodide, hydrogen iodide, water, methyl acetate, acetic acid, dimethyl ether, methanol, acetaldehyde, and formic acid, where the light ends herein are components having lower boiling points as compared with acetic acid. The vapors as above are continuously introduced through the line 33 into the condenser 5a.

In a preferred embodiment, the vapors drawn from the column top portion of the distillation column 5 include larger amounts of light ends as compared with the bottoms from the distillation column 5, and typically include methyl iodide, hydrogen iodide, water, methyl acetate, acetic acid, dimethyl ether, methanol, acetaldehyde, crotonaldehyde, and formic acid, where the light ends herein are components having lower boiling points as compared with acetic acid. The vapors as above are continuously introduced through the line 33 to the condenser 5a.

The condenser 5a cools and partially condenses the vapors from the distillation column 5 to separate the vapors into condensates and gases. The condensates typically include water and acetic acid. Of the condensates, a part is continuously refluxed from the condenser 5a through the line 35 to the distillation column 5; and another part is introduced and recycled from the condenser 5a through the lines 35, 36, and 23 to the reactor 1. The gases from the condenser 5a typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid, and are fed from the condenser 5a through the lines 37 and 15 to the scrubbing system 8. Hydrogen iodide in the gases that reach the scrubbing system 8 is absorbed by the absorbing liquid in the scrubbing system 8, and hydrogen iodide in the absorbing liquid reacts with methanol or methyl acetate to give methyl iodide. The resulting liquid containing the methyl iodide and other useful components is recycled from the scrubbing system 8 through the recycle lines 48 and 23 to the reactor 1.

The bottoms drawn from the column bottom portion of the distillation column 5 (or a side stream) include larger amounts of heavy ends as compared with the overhead stream from the distillation column 5 and typically include propionic acid, potassium acetate (when potassium hydroxide is fed typically to the line 27), and the catalyst and the promoter as being entrained, where the heavy ends are components having higher boiling points as compared with acetic acid. The bottoms may also include acetic acid. The bottoms as above are continuously introduced, as a second acetic acid stream, through the line 34 to the subsequent (downstream) distillation column 6.

The second acetic acid stream is enriched with acetic acid as compared with the first acetic acid stream which is continuously introduced into the distillation column 5. The acetic acid concentration in the second acetic acid stream is higher than the acetic acid concentration in the first acetic acid stream. The acetic acid concentration in the second acetic acid stream is typically 99.1 to 99.99 mass percent, as long as being higher than the acetic acid concentration in the first acetic acid stream. The second acetic acid stream may include, in addition to acetic acid, other components such as propionic acid and hydrogen iodide, as described above. In the embodiment, the side stream, when to be drawn, is drawn from the distillation column 5 at a level lower than the level at which the first acetic acid stream is introduced into the distillation column 5, where the levels are height levels at the distillation column 5.

In a preferred embodiment, the second acetic acid stream, which is the bottoms drawn from the column bottom portion of the distillation column 5 or the side stream drawn from a portion at an intermediate level of the column, is enriched with acetic acid as compared with the first acetic acid stream which is continuously introduced into the distillation column 5. The acetic acid concentration in the second acetic acid stream is higher than the acetic acid concentration in the first acetic acid stream. The acetic acid concentration in the second acetic acid stream is typically 99.1 to 99.99 mass percent, as long as being higher than the acetic acid concentration in the first acetic acid stream. In the embodiment, the side stream, when to be drawn, is drawn from the distillation column 5 at a level lower than the level at which the first acetic acid stream is introduced into the distillation column 5, where the levels are height levels at the distillation column 5.

In the present invention, the second acetic acid stream yields a good potassium permanganate test result and can serve as intact as an acetic acid product. However, the second acetic acid stream may include trace amounts of impurities (such as crotonaldehyde, 2-ethylcrotonaldehyde, butyl acetate, propionic acid, potassium acetate (when potassium hydroxide is fed typically to the line 27), hydrogen iodide, and the catalyst and the promoter as being entrained. Accordingly, the bottoms or side stream may be continuously introduced through the line 34 into the distillation column 6 and be subjected to distillation therein.

The second acetic acid stream has a crotonaldehyde concentration of typically 2.0 ppm by mass or less, preferably 1.8 ppm by mass or less, more preferably 1.5 ppm by mass or less, furthermore preferably 1.2 ppm by mass or less, and particularly preferably 0.7 ppm by mass or less (for example, 0.5 ppm by mass or less). The second acetic acid stream has an 2-ethylcrotonaldehyde concentration of typically 3.0 ppm by mass or less, preferably 2.0 ppm by mass or less, more preferably 1.0 ppm by mass or less, and furthermore preferably 0.8 ppm by mass or less (for example, 0.5 ppm by mass or less). The second acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of typically 50 or less, preferably 35 or less, more preferably 25 or less, furthermore preferably 20 or less, and still more preferably 15 or less. The lower limit of the ratio may be typically 0.5, 0.3, 0.1, 0.05, or 0.01. In the present invention, the ratio ($C_{CR}/C_{ECR}$) of the crotonaldehyde concentration $C_{CR}$ (ppm by mass) to the 2-ethylcrotonaldehyde concentration $C_{ECR}$ (ppm by mass) may be regulated by controlling both the crotonaldehyde concentration and the 2-ethylcrotonaldehyde concentration in the second acetic acid stream together. Specifically, it is acceptable that, by efficient separation in the separation step using the difference in boiling point from acetic acid, crotonaldehyde is concentrated in the overhead condensate from the dehydration column (second distillation column), and thereby the crotonaldehyde concentration is lowered and the 2-ethylcrotonaldehyde concentration is regulated in the second acetic acid stream, where the second acetic acid stream is obtained as a side stream or bottoms stream from the dehydration column. Thus, both the crotonaldehyde concentration and the 2-ethylcrotonaldehyde concentration in the second acetic acid stream can be controlled together. With a decreasing ratio ($C_{CR}/C_{ECR}$), the acetic acid product has a better potassium permanganate test result, because crotonaldehyde more adversely affects the potassium permanganate test result as compared with 2-ethylcrotonaldehyde.

The second acetic acid stream has a butyl acetate concentration of typically 15 ppm by mass or less, preferably 12 ppm by mass or less, more preferably 10 ppm by mass or less, and furthermore preferably 8 ppm by mass or less. The lower limit of the butyl acetate concentration in the second acetic acid stream is typically 0 ppm by mass (or 0.1 ppm by mass). The second acetic acid stream has a ratio ($C_{CR}/C_{BA}$) of the crotonaldehyde concentration $C_{CR}$ (ppm by mass) to the butyl acetate concentration $C_{EA}$ (ppm by mass) of typically 2.0 or less, preferably 1.5 or less, more preferably 1.0 or less, and furthermore preferably 0.6 or less. The lower limit of the ratio may be typically 0.1, 0.05, 0.02, 0.01, or 0.001. With a decreasing ratio ($C_{CR}/C_{BA}$), the acetic acid product has a better potassium permanganate test result, because butyl acetate is approximately harmless to the potassium permanganate test.

In a preferred embodiment, the second acetic acid stream has a crotonaldehyde concentration of typically 0.98 ppm by mass or less, preferably 0.80 ppm by mass or less, more preferably 0.50 ppm by mass or less, furthermore preferably 0.30 ppm by mass or less, and particularly preferably 0.17 ppm by mass or less. The second acetic acid stream, when controlled to have a crotonaldehyde concentration of 0.98 ppm by mass or less, can not only have a significantly lower crotonaldehyde concentration, but also yield a significantly better potassium permanganate test result. The lower limit of the crotonaldehyde concentration in the second acetic acid stream may be 0 ppm by mass, or may be typically 0.01 ppm by mass (or 0.10 ppm by mass). In a preferred embodiment, the second acetic acid stream has an 2-ethylcrotonaldehyde concentration of typically 1.0 ppm by mass or less, preferably 0.50 ppm by mass or less, more preferably 0.30 ppm by mass or less, and furthermore preferably 0.20 ppm by mass or less. The second acetic acid stream, when controlled to have an 2-ethylcrotonaldehyde concentration of 1.0 ppm by mass or less, can yield a still better potassium permanganate test result. The lower limit of the 2-ethylcrotonaldehyde concentration in the second acetic acid stream may be typically 0 ppm by mass, or 0.01 ppm by mass (for example, 0.10 ppm by mass).

In a preferred embodiment, the second acetic acid stream has a butyl acetate concentration of typically 15 ppm by mass or less, preferably 10 ppm by mass or less, more preferably 8 ppm by mass or less, and particularly preferably 5 ppm by mass or less (for example, 3 ppm by mass or less). The second acetic acid stream, when controlled to have a butyl acetate concentration of 15 ppm by mass or less, can have higher quality. The lower limit of the butyl acetate concentration in the second acetic acid stream may be typically 0 ppm by mass, or 0.1 ppm by mass (for example, 0.3 ppm by mass or 1.0 ppm by mass).

The second acetic acid stream yields a potassium permanganate test result of preferably longer than 50 minutes, more preferably 60 minutes or longer, furthermore preferably 100 minutes or longer, and particularly preferably 120 minutes or longer (for example, 180 minutes or longer, especially preferably 240 minutes or longer, and particularly 360 minutes or longer).

Potassium hydroxide may be fed or added through the line 56 (potassium hydroxide introducing line) to the second acetic acid stream passing through the line 34. The potassium hydroxide may be fed or added as a solution such as an aqueous solution. The feeding or addition of potassium hydroxide to the second acetic acid stream can decrease hydrogen iodide in the second acetic acid stream. Specifically, hydrogen iodide reacts with potassium hydroxide to form potassium iodide and water. This can decrease corrosion of the equipment such as distillation columns, where the corrosion will be caused by hydrogen iodide.

The distillation column 6 is a unit with which the third distillation step is performed. The distillation column 6 in the embodiment is characterized as a so-called heavy ends column. The third distillation step is the step of subjecting the second acetic acid stream, which is continuously introduced into the distillation column 6, to a purification treatment to further purify acetic acid. This step is not indispensable in the embodiment. The distillation column 6 may be selected typically from rectification columns such as plate columns and packed columns. A plate column, when employed as the distillation column 6, typically has 5 to 50 theoretical plates and is operated at a reflux ratio of typically 0.2 to 3000, where the reflux ratio may be determined according to the number of theoretical plates. In the distillation column 6 during the third distillation step, the column top pressure is set typically to −100 to 150 kPa (gauge pressure); and the column bottom pressure is set higher than the column top pressure and is typically −90 to 180 kPa (gauge pressure). In the distillation column 6 during the third distillation step, the column top temperature is set typically to a temperature which is higher than the boiling point of water and lower than the boiling point of acetic acid at the set column top pressure and which is from 50° C. to 150° C.; and the column bottom temperature is set typically to a temperature which is higher than the boiling point of acetic acid at the set column bottom pressure and which is from 70° C. to 160° C.

At the distillation column 6, vapors as an overhead stream are continuously drawn from a column top portion to the line 38; and bottoms are continuously drawn from a column bottom portion to the line 39. There is disposed the reboiler 6b. A side stream (liquid or gas) is continuously drawn, to the line 46, from a portion at a height level between the column top portion and the column bottom portion in the distillation column 6. The line 46 may be coupled to the distillation column 6 at a level higher than the coupling level of the line 34 to the distillation column 6, as illustrated in the figure, but may be coupled at a level lower than, or equal to, the coupling level of the line 34 to the distillation column 6, where the levels are height levels at the distillation column 6.

The vapors drawn from the column top portion of the distillation column 6 include larger amounts of light ends as compared with the bottoms from the distillation column 6, where the light ends are components having lower boiling points as compared with acetic acid. The vapors include acetic acid, and other components such as methyl iodide, hydrogen iodide, water, methyl acetate, dimethyl ether, methanol, and formic acid. The vapors as above are continuously introduced through the line 38 into the condenser 6a.

The condenser 6a cools and partially condensates the vapors from the distillation column 6 to separate the vapors into condensates and gases. The condensates include acetic acid, and other components such as methyl iodide, hydrogen iodide, water, methyl acetate, dimethyl ether, methanol, and formic acid. At least a part of the condensates is continuously refluxed from the condenser 6a through the line 40 to the distillation column 6. A part (distillate) of the condensates can be recycled from the condenser 6a through the lines 40, 41, and 42 to the first acetic acid stream in the line 27 before the introduction of the stream into the distillation column 5. In addition to, or instead of this, a part (distillate) of the condensates can be recycled from the condenser 6a through the lines 40, 41, and 43 to the vapor stream in the line 21 before the introduction of the stream into the distillation column 3. A part (distillate) of the condensates may be recycled from the condenser 6a through the lines 40, 44, and 23 to the reactor 1. A part of the distillate from the condenser 6a can be fed to the scrubbing system 8 and be used as the absorbing liquid in the system, as described above. A gas after absorption of useful components in the scrubbing system 8 is discharged out of the equipment. The resulting liquid containing the useful components is introduced or recycled from the scrubbing system 8 through the recycle lines 48 and 23 to the reactor 1. In addition, a part of the distillate from the condenser 6a may be brought through lines (not shown) to various pumps (not shown) operated in the equipment and be used as a sealing liquid for the pumps. Further, a part of the distillate from the condenser 6a may be drawn out of the system through a draw line attached to the line 40 steadily, or non-steadily at the time of need. When a part (distillate) of the condensates is removed from the distillation treatment system in the distillation column 6, the amount of the distillate (distillate amount) is typically 0.01 to 30 mass percent, preferably 0.1 to 10 mass percent, more preferably 0.3 to 5 mass percent, and furthermore preferably 0.5 to 3 mass percent, of the condensates obtained by the working of the condenser 6a. In contrast, the gases formed in the condenser 6a typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gases are fed from the condenser 6a through the lines 45 and 15 to the scrubbing system 8.

The bottoms drawn from the column bottom portion of the distillation column 6 through the line 39 include larger amounts of heavy ends as compared with the overhead stream from the distillation column 6, where the heavy ends are components having higher boiling points as compared with acetic acid. The bottoms typically include propionic acid, and potassium acetate (when potassium hydroxide is fed typically to the line 34). The bottoms drawn from the column bottom portion of the distillation column 6 through the line 39 also include corrodible metals and other metals exemplified by metals liberated from inner walls of constitutional members of the acetic acid production equipment; and compounds between iodine derived from corrosive iodine and the corrodible metals and other metals. In the embodiment, the bottoms as above are discharged out of the acetic acid production equipment.

In a preferred embodiment, the bottoms drawn from the column bottom portion of the distillation column 6 through the line 39 include larger amounts of heavy ends as compared with the overhead stream from the distillation column 6, where the heavy ends are components having higher boiling points as compared with acetic acid; and typically include propionic acid, and acetates such as potassium acetate (when potassium hydroxide or another alkali is fed typically to the line 34). The bottoms drawn from the column bottom portion of the distillation column 6 through the line 39 also include corrodible metals and other metals, exemplified by metals liberated from inner walls of constitutional members of the acetic acid production equipment; and compounds between iodine derived from corrosive iodine and the corrodible metals and other metals. In the embodiment, the bottoms as above are discharged out of the acetic acid production equipment.

The side stream continuously drawn from the distillation column 6 to the line 46 is continuously introduced, as a third acetic acid stream, into the subsequent ion exchange resin column 7. The third acetic acid stream is enriched with acetic acid as compared with the second acetic acid stream which is continuously introduced into the distillation column 6. Specifically, the acetic acid concentration in the third acetic acid stream is higher than the acetic acid concentration in the second acetic acid stream. The acetic acid concentration in the third acetic acid stream is typically 99.8 to 99.999 mass percent, as long as being higher than the acetic acid concentration in the second acetic acid stream. In the embodiment, the side stream is drawn from the distillation column 6 at a level higher than the level at which the second acetic acid stream is introduced into the distillation column 6, where the levels are height levels at the distillation column 6. In another embodiment, the side stream is drawn from the distillation column 6 at a level equal to or lower than the level at which the second acetic acid stream is introduced into the distillation column 6, where the levels are height levels at the distillation column 6. A simple distillator (evaporator) is usable in place of the distillation column 6. The distillation column 6 can be omitted when impurities have been sufficiently removed by the working of the distillation column 5.

In a preferred embodiment, the side stream continuously drawn from the distillation column 6 to the line 46 is continuously introduced, as a third acetic acid stream, into the subsequent (downstream) ion exchange resin column 7. The third acetic acid stream is enriched with acetic acid as compared with the second acetic acid stream which is continuously introduced into the distillation column 6. Specifically, the acetic acid concentration in the third acetic acid stream is higher than the acetic acid concentration in the second acetic acid stream. The acetic acid concentration in the third acetic acid stream is typically 99.8 to 99.999 mass percent, as long as being higher than the acetic acid concentration in the second acetic acid stream. In the embodiment, the side stream is drawn from the distillation column 6 at a level higher than the level at which the second acetic acid stream is introduced into the distillation column 6, where the levels are height levels at the distillation column 6. In another embodiment, the side stream is drawn from the distillation column 6 at a level equal to or lower than the level at which the second acetic acid stream is introduced into the distillation column 6, where the levels are height levels at the distillation column 6. A simple distillator (evaporator) is usable in place of the distillation column 6. In particular, the present invention can omit the distillation column 6, because the present invention can give acetic acid yielding a very high potassium permanganate test result by the distillation treatment in the distillation column 5.

The ion exchange resin column 7 is a purification unit with which the adsorptive removing step is performed. The adsorptive removing step is the step of adsorptively removing mainly alkyl iodides (such as hexyl iodide and decyl iodide) contained in trace amounts in the third acetic acid stream, so as to further purify acetic acid, where the third acetic acid stream is continuously introduced into the ion exchange resin column 7. In the ion exchange resin column 7, an ion exchange resin capable of adsorbing alkyl iodides is packed and forms an ion exchange resin bed. Non-limiting examples of the ion exchange resin as above include cation-exchange resins with part of leaving protons in exchange groups being substituted or replaced with a metal such as silver or copper, where the exchange groups are exemplified typically by sulfonic groups, carboxy groups, and phosphonate groups. In the adsorptive removing step, the third acetic acid stream (liquid) passes through the inside of the ion exchange resin column 7 packed typically with the ion exchange resin as above, and, during the passing process, alkyl iodides and other impurities in the third acetic acid stream are adsorbed by the ion exchange resin and removed from the third acetic acid stream. In the ion exchange resin column 7 during the adsorptive removing step, the inside temperature is typically 18° C. to 100° C., and the acetic acid stream flow rate is typically 3 to 15 m$^3$/h·m$^3$ (resin volume), where the acetic acid stream flow rate is the acetic acid throughput (m$^3$/h) per cubic meter of the resin volume.

In a preferred embodiment, the ion exchange resin column 7 is a purification unit with which an adsorptive removing step is performed. This adsorptive removing step is the step of adsorptively removing mainly alkyl iodides contained in trace amounts in the third acetic acid stream to further purify acetic acid, where the third acetic acid stream is continuously introduced into the ion exchange resin column 7. Non-limiting examples of the alkyl iodides include ethyl iodide, propyl iodide, butyl iodide, hexyl iodide, and decyl iodide. It is also acceptable that the distillation column 6 is omitted, and the second acetic acid stream from the distillation column 5 is fed to the ion exchange resin column 7. The adsorptive removing step using the ion exchange resin column 7 is not indispensable.

In a preferred embodiment, the ion exchange resin column 7 is packed with an ion exchange resin capable of adsorbing alkyl iodides, where the ion exchange resin forms an ion exchange resin bed in the column. Non-limiting examples of the ion exchange resin as above include cation-exchange resins with part of leaving protons in exchange groups being substituted or replaced with a metal such as silver or copper, where the exchange groups are exemplified typically by sulfonic groups, carboxy groups, and phosphonate groups. In the adsorptive removing step, the third acetic acid stream (liquid) passes through the inside of the ion exchange resin column 7 packed typically with the ion exchange resin as above, and, during the passing process, alkyl iodides and other impurities in the third acetic acid stream are adsorbed by the ion exchange resin and removed from the third acetic acid stream. At the ion exchange resin column 7 during the adsorptive removing step, the inside temperature is typically 18° C. to 100° C., and the flow rate of the acetic acid stream is typically 3 to 15 m$^3$/h·m$^3$ (resin volume), where the flow rate is the acetic acid throughput (m$^3$/h) per cubic meter of the resin volume.

A fourth acetic acid stream is continuously brought from a bottom portion of the ion exchange resin column 7 to the line 47. The fourth acetic acid stream has a higher acetic acid concentration than the acetic acid concentration in the third acetic acid stream. Specifically, the fourth acetic acid stream is enriched with acetic acid as compared with the third acetic acid stream which is continuously introduced into the ion exchange resin column 7. The acetic acid concentration in the fourth acetic acid stream is typically 99.9 to 99.999 mass percent, or more, as long as being higher than the acetic acid concentration in the third acetic acid stream. In the production method, the fourth acetic acid stream can be stored in a product tank (not shown).

This acetic acid production equipment may include a so-called product column or finishing column, which is a distillation column, as a purification unit for further purifying the fourth acetic acid stream from the ion exchange resin column 7. The product column as above, when provided, may be selected typically from rectification columns such as plate columns and packed columns. A plate column, when employed as the product column, typically has 5 to 50 theoretical plates and is operated at a reflux ratio of typically 0.5 to 3000, where the reflux ratio may be determined according to the number of theoretical plates. In the product column during the purification step, the column top pressure is set typically to −195 to 150 kPa (gauge pressure); and the column bottom pressure is set at a pressure which is higher than the column top pressure and is typically −190 to 180 kPa (gauge pressure). In the product column, the column top temperature is typically set to a temperature which is higher than the boiling point of water and lower than the boiling point of acetic acid at the set column top pressure, and which is from 50° C. to 150° C.; and the column bottom temperature is typically set to a temperature which is higher than the boiling point of acetic acid at the set column bottom pressure and which is from 70° C. to 160° C. In place of the product column or finishing column, a simple distillator (evaporator) may be used.

Into the product column, when provided, all or a part of the fourth acetic acid stream (liquid) from the ion exchange resin column 7 is continuously introduced. At the product column as above, vapors as an overhead stream are continuously drawn from a column top portion, where the vapors include trace amounts of light ends such as methyl iodide, water, methyl acetate, dimethyl ether, crotonaldehyde, acetaldehyde, and formic acid. The vapors are separated, using a predetermined condenser, into condensates and gases. Of the condensates, a part is continuously refluxed to the product column; and another part may be recycled to the reactor 1, or be discharged to the outside of the system, or both. The gases are fed to the scrubbing system 8. At the product column, bottoms including trace amounts of heavy ends are continuously drawn from a column bottom portion, and are typically recycled to the second acetic acid stream in the line 34 before the introduction of the stream into the distillation column 6. At the product column, a side stream (liquid) as a fifth acetic acid stream is continuously drawn from a portion at a height level between the column top portion and the column bottom portion. The side stream is drawn from the product column typically at a level lower than the level at which the fourth acetic acid stream is introduced into the product column, where the levels are height levels at the product column. The fifth acetic acid stream is enriched with acetic acid as compared with the fourth acetic acid stream which is continuously introduced into the product column. Specifically, the acetic acid concentration in the fifth acetic acid stream is higher than the acetic acid concentration in the fourth acetic acid stream. The acetic acid concentration in the fifth acetic acid stream is typically 99.9 to 99.999 mass percent, or more, as long as being higher than the acetic acid concentration in the fourth acetic acid stream. The fifth acetic acid stream is stored typically in a product tank. Instead of, or in addition to being arranged downstream from the distillation column 6, the ion exchange resin column 7 may be arranged downstream from the product column, for the treatment of the acetic acid stream from the product column.

EXAMPLES

The present invention will be illustrated in further detail with reference to several examples below. It should be noted, however, that the examples are by no means intended to limit the scope of the present invention. All parts, percentages, parts per million (ppm), and parts per billion (ppb) are by mass. Water concentrations were measured by the Karl Fischer method (moisture measurement method), metal ion concentrations were measured by ICP analysis (or atomic absorption spectrometry), potassium permanganate test results were determined in accordance with the procedure for visual colorimetry prescribed in JIS K 1351:1993, and concentrations of other components were measured by gas chromatography. The terms "AD" represents acetaldehyde, "MeI" represents methyl iodide, "MA" represents methyl acetate, and "AC" represents acetic acid. AD partition coefficients between an aqueous phase and an organic phase, and MA partition coefficients between an aqueous phase and an organic phase were determined according to equations as follows:

AD partition coefficient={AD concentration (mass percent) in aqueous phase}/{AD concentration (mass percent) in organic phase}

MA partition coefficient={MA concentration (mass percent) in aqueous phase}/{MA concentration (mass percent) in organic phase}

Initially, experiments as follows were performed to investigate conditions for a liquid-liquid separation step.

Experimental Examples 1 to 10

Experimental Examples 1 to 10 are experiments to investigate how the concentrations of components in the resulting aqueous phase and the organic phase, and the AD partition coefficient vary at different AD concentrations in a charge liquid (liquid-liquid separation step feed liquid) subjected to the liquid-liquid separation step. The experiments were performed using a pressurization-capable liquid-liquid equilibrium measuring apparatus 300. With reference to FIG. 6, the apparatus 300 includes a pressure-tight glass vessel 301 (inner capacity: 100 cc), a stirring chip 302 (spindle shaped), a lower phase sampling pipe 303, an upper phase sampling pipe 304, a thermometer 305, a magnetic stirrer 306, a water bath 307, a thermoregulator 308, a thermometer 309, a lower phase sampling tube 310, an upper phase sampling tube 311, a pressure gauge 312, a pressure control valve 313, valves 314, 315, 316, and 317, a safety valve 318, a lower phase sampling line 319, an upper phase sampling line 320, a nitrogen gas inlet line 321, a pressure release line 322, and an exhaust line 323. The dotted line represents a liquid level or an interface.

Into the pressure-tight glass vessel 301, AD, MeI, and water in amounts given in "Actual charge amount" in Table 1 were charged, the stirring chip 302 was placed, and the lid was closed. After nitrogen purge in the vessel, the temperature of the vessel was regulated, on the water bath 307, to the temperature given in "Temperature" in Table 1, followed by stirring at 300 rpm for 30 minutes. After the stirring was stopped, the resulting mixture was left stand for 10 minutes. After checking complete liquid-liquid separation, the resulting aqueous phase and organic phase (methyl iodide phase) were sampled respectively into the sampling tubes 311 and 310, and were each examined so as to measure the concentrations of AD, MeI, and water and to determine AD partition coefficients. The results are given in Table 1.

Experimental Examples 11 to 15

Experimental Examples 11 to 15 are experiments to investigate how the concentrations of components in the aqueous phase and the organic phase, and the AD partition coefficient vary at different temperatures (liquid temperatures) in the liquid-liquid separation step, when the AD concentration in the charge liquid is set constant.

A procedure similar to that in Experimental Examples 1 to 10 was performed, except for charging AD, MeI, and water into the pressure-tight glass vessel 301 in the amounts given in Table 1, and performing the liquid-liquid separation step at the temperature given in Table 1. The concentrations of components in the aqueous phase and the organic phase were measured, and the AD partition coefficient was determined. The results are given in Table 1.

Experimental Examples 16 to 21

Experimental Examples 16 to 21 are experiments to investigate how the concentrations of components in the aqueous phase and the organic phase and the AD partition coefficient vary at different temperatures (liquid temperatures) in the liquid-liquid separation step, when the AD concentration and MA concentration in the charge liquid are set constant.

A procedure similar to that in Experimental Examples 1 to 10 was performed, except for charging AD, MeI, MA, and water into the pressure-tight glass vessel 301 in the amounts given in Table 2, and performing the liquid-liquid separation step at the temperature given in Table 2. The concentrations of components in the aqueous phase and the organic phase were measured, and the AD partition coefficient and the MA partition coefficient were determined. The results are given in Table 2.

Experimental Examples 22 to 26

Experimental Examples 22 to 26 are experiments to investigate how the concentrations of components in the aqueous phase and the organic phase, and the AD partition coefficient vary at different MA concentrations in the charge liquid.

A procedure similar to that in Experimental Examples 1 to 10 was performed, except for charging AD, MeI, MA, and water into the pressure-tight glass vessel 301 in the amounts given in Table 2, and performing the liquid-liquid separation step at the temperature given in Table 2. The concentrations of components in the aqueous phase and the organic phase were measured, and the AD partition coefficient and the MA partition coefficient were determined. The results are given in Table 2.

Referential Examples 1 and 2

Referential Examples 1 and 2 are experiments to investigate how the concentrations of components in the aqueous phase and the organic phase, and the AD partition coefficient vary at different AC concentrations in the charge liquid.

A procedure similar to that in Experimental Examples 1 to 10 was performed, except for charging AD, MeI, water, and AC into the pressure-tight glass vessel 301 in the amounts given in Table 2, and performing the liquid-liquid separation step at the temperature given in Table 2. The concentrations of components in the aqueous phase and the organic phase were measured, and the AD partition coefficient was determined. The results are given in Table 2.

TABLE 1

| | | | Experimental Examples | | | | | | | |
|---|---|---|---|---|---|---|---|---|---|---|
| | | | Exp. Ex. 1 | Exp. Ex. 2 | Exp. Ex. 3 | Exp. Ex. 4 | Exp. Ex. 5 | Exp. Ex. 6 | Exp. Ex. 7 | Exp. Ex. 8 |
| Actual charge amount (g) | | AD | 0.05 | 0.11 | 0.20 | 0.39 | 0.81 | 1.62 | 5.63 | 21.20 |
| | | MeI | 132.15 | 132.02 | 132.10 | 132.95 | 131.91 | 132.05 | 128.04 | 115.06 |
| | | MA | | | | | | | | |
| | | $H_2O$ | 60.09 | 60.09 | 60.11 | 60.23 | 59.85 | 60.15 | 54.01 | 41.05 |
| | | AC | | | | | | | | |
| | | Total | 192.29 | 192.22 | 192.41 | 193.57 | 192.57 | 193.82 | 187.68 | 177.31 |
| Temperature | | (° C.) | 40 | 40.2 | 40.1 | 40.2 | 40.2 | 40.2 | 40.1 | 40.1 |
| Pressure | | (MPaG) | 0.05 | 0.05 | 0.05 | 0.05 | 0.05 | 0.05 | 0.05 | 0.07 |
| Actual charge (wt %) | | AD | 0.026% | 0.057% | 0.104% | 0.201% | 0.42% | 0.84% | 3.0% | 12.0% |
| | | MeI | 68.7% | 68.7% | 68.7% | 68.7% | 68.5% | 68.1% | 68.2% | 64.9% |
| | | MA | | | | | | | | |
| | | $H_2O$ | 31.2% | 31.3% | 31.2% | 31.1% | 31.1% | 31.0% | 28.8% | 23.2% |
| | | AC | | | | | | | | |
| | | Total | 100.0% | 100.0% | 100.0% | 100.0% | 100.0% | 100.0% | 100.0% | 100.0% |
| Aqueous phase (wt %) | | AD | 0.045% | 0.098% | 0.190% | 0.371% | 0.76% | 1.539% | 5.22% | 16.78% |
| | | MeI | 2.45% | 2.45% | 2.45% | 2.46% | 2.47% | 2.49% | 2.53% | 3.09% |
| | | MA | | | | | | | | |
| | | $H_2O$ | 97.50% | 97.45% | 97.36% | 97.17% | 96.77% | 95.97% | 92.24% | 80.14% |
| | | AC | | | | | | | | |
| | | Total | 100.0% | 100.0% | 100.0% | 100.0% | 100.0% | 100.0% | 100.0% | 100.0% |
| Organic phase (wt %) | | AD | 0.013% | 0.030% | 0.058% | 0.115% | 0.240% | 0.495% | 1.95% | 9.48% |
| | | MeI | 99.49% | 99.47% | 99.44% | 99.39% | 99.26% | 99.01% | 97.18% | 90.06% |
| | | MA | | | | | | | | |
| | | $H_2O$ | 0.50% | 0.50% | 0.50% | 0.50% | 0.50% | 0.50% | 0.87% | 0.46% |
| | | AC | | | | | | | | |
| | | Total | 100.0% | 100.0% | 100.0% | 100.0% | 100.0% | 100.0% | 100.0% | 100.0% |
| AD partition coefficient (aqueous phase/organic phase) | | | 3.35 | 3.30 | 3.26 | 3.22 | 3.17 | 3.11 | 2.68 | 1.8 |

| | | | Experimental Examples | | | | | | |
|---|---|---|---|---|---|---|---|---|---|
| | | | Exp. Ex. 9 | Exp. Ex. 10 | Exp. Ex. 11 | Exp. Ex. 12 | Exp. Ex. 13 | Exp. Ex. 14 | Exp. Ex. 15 |
| Actual charge amount (g) | | AD | 24.80 | 35.21 | 0.41 | 0.39 | 0.41 | 0.39 | 0.42 |
| | | MeI | 101.12 | 66.04 | 104.03 | 104.03 | 111.33 | 112.87 | 114.12 |
| | | MA | | | | | | | |
| | | $H_2O$ | 29.01 | 33.99 | 37.00 | 37.00 | 39.42 | 39.90 | 40.41 |
| | | AC | | | | | | | |
| | | Total | 154.93 | 135.24 | 141.44 | 141.42 | 151.16 | 153.16 | 154.95 |
| Temperature | | (° C.) | 40.2 | 40.2 | 70.0 | 50.0 | 30.6 | 20.6 | 11.1 |
| Pressure | | (MPaG) | 0.08 | 0.10 | 0.13 | 0.13 | 0.07 | 0.03 | 0.01 |
| Actual charge (wt %) | | AD | 16.0% | 26.0% | 0.3% | 0.3% | 0.3% | 0.3% | 0.3% |
| | | MeI | 65.3% | 48.8% | 73.6% | 73.6% | 73.7% | 73.7% | 73.6% |
| | | MA | | | | | | | |
| | | $H_2O$ | 18.7% | 25.1% | 26.2% | 26.2% | 26.1% | 26.1% | 26.1% |
| | | AC | | | | | | | |
| | | Total | 100.0% | 100.0% | 100.0% | 100.0% | 100.0% | 100.0% | 100.0% |

TABLE 1-continued

|  |  | | | | | | | |
|---|---|---|---|---|---|---|---|---|
| Aqueous phase (wt %) | AD | 20.64% | 28.10% | 0.44% | 0.51% | 0.54% | 0.50% | 0.60% |
|  | Mel | 3.98% | 5.43% | 2.47% | 2.46% | 3.37% | 2.40% | 2.30% |
|  | MA | | | | | | | |
|  | H$_2$O | 75.37% | 66.47% | 97.09% | 97.03% | 96.09% | 97.10% | 97.10% |
|  | AC | | | | | | | |
|  | Total | 100.0% | 100.0% | 100.0% | 100.0% | 100.0% | 100.0% | 100.0% |
| Organic phase (wt %) | AD | 14.06% | 24.80% | 0.230% | 0.181% | 0.153% | 0.122% | 0.143% |
|  | Mel | 85.18% | 73.34% | 99.13% | 99.18% | 99.45% | 99.56% | 99.57% |
|  | MA | | | | | | | |
|  | H$_2$O | 0.77% | 1.86% | 0.64% | 0.64% | 0.40% | 0.32% | 0.28% |
|  | AC | | | | | | | |
|  | Total | 100.0% | 100.0% | 100.0% | 100.0% | 100.0% | 100.0% | 100.0% |
| AD partition coefficient (aqueous phase/organic phase) | | 1.5 | 1.1 | 1.9 | 2.8 | 3.5 | 4.1 | 4.2 |

TABLE 2

| | | Experimental Example | | | | | | |
|---|---|---|---|---|---|---|---|---|
| | | Exp. Ex. 16 | Exp. Ex. 17 | Exp. Ex. 18 | Exp. Ex. 19 | Exp. Ex. 20 | Exp. Ex. 21 | Exp. Ex. 22 |
| Actual charge amount (g) | AD | 0.40 | 0.41 | 0.41 | 0.39 | 0.40 | 0.44 | 0.42 |
| | Mel | 88.49 | 89.68 | 94.94 | 98.18 | 101.08 | 105.53 | 127.09 |
| | MA | 7.43 | 7.55 | 7.98 | 8.21 | 8.55 | 8.43 | 3.80 |
| | H$_2$O | 34.21 | 34.66 | 36.72 | 37.59 | 39.01 | 40.50 | 59.01 |
| | AC | | | | | | | |
| | Total | 130.53 | 132.30 | 140.05 | 144.37 | 149.04 | 154.90 | 190.32 |
| Temperature | (° C.) | 50.3 | 40.6 | 30.5 | 21.0 | 11.3 | −5.1 | 40.3 |
| Pressure | (MPaG) | 0.14 | 0.11 | 0.07 | 0.05 | 0.02 | 0.02 | 0.06 |
| Actual charge (wt %) | AD | 0.31% | 0.31% | 0.29% | 0.27% | 0.27% | 0.28% | 0.22% |
| | Mel | 67.8% | 67.8% | 67.8% | 68.0% | 67.8% | 68.1% | 66.8% |
| | MA | 5.7% | 5.7% | 5.7% | 5.7% | 5.7% | 5.4% | 2.0% |
| | H$_2$O | 26.2% | 26.2% | 26.2% | 26.0% | 26.2% | 26.1% | 31.0% |
| | AC | | | | | | | |
| | Total | 100.0% | 100.0% | 100.0% | 100.0% | 100.0% | 100.0% | 100.0% |
| Aqueous phase (wt %) | AD | 0.55% | 0.60% | 0.61% | 0.55% | 0.54% | 0.56% | 0.46% |
| | Mel | 3.72% | 2.83% | 2.62% | 2.58% | 2.97% | 2.88% | 2.31% |
| | MA | 2.28% | 2.18% | 2.25% | 2.30% | 2.48% | 2.51% | 1.21% |
| | H$_2$O | 93.45% | 94.40% | 94.53% | 94.57% | 94.01% | 94.05% | 96.03% |
| | AC | | | | | | | |
| | Total | 100.0% | 100.0% | 100.0% | 100.0% | 100.0% | 100.0% | 100.0% |
| Organic phase (wt %) | AD | 0.190% | 0.194% | 0.179% | 0.145% | 0.132% | 0.124% | 0.134% |
| | Mel | 93.00% | 93.16% | 93.25% | 93.45% | 93.47% | 93.60% | 95.71% |
| | MA | 5.94% | 5.92% | 5.96% | 5.92% | 5.99% | 5.90% | 2.29% |
| | H$_2$O | 0.87% | 0.73% | 0.60% | 0.48% | 0.42% | 0.38% | 1.87% |
| | AC | | | | | | | |
| | Total | 100.0% | 100.0% | 100.0% | 100.0% | 100.0% | 100.0% | 100.0% |
| AD partition coefficient (aqueous phase/organic phase) | | 2.9 | 3.1 | 3.4 | 3.8 | 4.1 | 4.5 | 3.4 |
| Aqueous phase MA concentration + organic phase MA concentration (wt %) | | 8.22% | 8.01% | 8.21% | 8.22% | 8.47% | 8.41% | 3.50% |
| MA partition coefficient (aqueous phase/organic phase) | | 0.38 | 0.37 | 0.38 | 0.39 | 0.41 | 0.43 | 0.53 |

| | | Experimental Example | | | | | |
|---|---|---|---|---|---|---|---|
| | | Exp. Ex. 23 | Exp. Ex. 24 | Exp. Ex. 25 | Exp. Ex. 26 | Ref. Ex. 1 | Ref. Ex. 2 |
| Actual charge amount (g) | AD | 0.40 | 0.43 | 0.42 | 0.42 | 0.41 | 0.40 |
| | Mel | 109.12 | 78.01 | 46.03 | 46.03 | 113.01 | 92.02 |
| | MA | 8.68 | 23.03 | 39.03 | 56.00 | | |
| | H$_2$O | 55.97 | 50.01 | 44.02 | 44.02 | 58.00 | 57.00 |
| | AC | | | | | 9.01 | 17.02 |
| | Total | 174.17 | 151.48 | 129.50 | 146.47 | 180.43 | 166.44 |

TABLE 2-continued

|  |  |  |  |  |  |  |  |
|---|---|---|---|---|---|---|---|
| Temperature | (° C.) | 40.3 | 40.3 | 40.5 | 40.5 | 40.0 | 40.0 |
| Pressure | (MPaG) | 0.06 | 0.06 | 0.06 | 0.06 | 0.06 | 0.06 |
| Actual charge (wt %) | AD | 0.23% | 0.28% | 0.32% | 0.29% | 0.23% | 0.24% |
|  | Mel | 62.7% | 51.5% | 35.5% | 31.4% | 62.6% | 55.3% |
|  | MA | 5.0% | 15.2% | 30.1% | 38.2% |  |  |
|  | $H_2O$ | 32.1% | 33.0% | 34.0% | 30.1% | 32.1% | 34.2% |
|  | AC |  |  |  |  | 5.0% | 10.2% |
|  | Total | 100.0% | 100.0% | 100.0% | 100.0% | 100.0% | 100.0% |
| Aqueous phase (wt %) | AD | 0.42% | 0.41% | 0.37% | 0.30% | 0.40% | 0.39% |
|  | Mel | 2.23% | 1.68% | 1.45% | 1.20% | 3.09% | 3.37% |
|  | MA | 2.56% | 6.01% | 10.36% | 12.00% |  |  |
|  | $H_2O$ | 94.79% | 91.90% | 87.82% | 86.50% | 84.90% | 73.89% |
|  | AC |  |  |  |  | 11.61% | 22.35% |
|  | Total | 100.0% | 100.0% | 100.0% | 100.0% | 100.0% | 100.0% |
| Organic phase (wt %) | AD | 0.136% | 0.21% | 0.29% | 0.28% | 0.127% | 0.125% |
|  | Mel | 93.50% | 79.34% | 56.63% | 49.15% | 98.88% | 98.75% |
|  | MA | 5.81% | 19.57% | 41.08% | 47.57% |  |  |
|  | $H_2O$ | 0.55% | 0.88% | 2.00% | 3.00% | 0.24% | 0.28% |
|  | AC |  |  |  |  | 0.75% | 0.85% |
|  | Total | 100.0% | 100.0% | 100.0% | 100.0% | 100.0% | 100.0% |
| AD partition coefficient (aqueous phase/organic phase) |  | 3.1 | 1.9 | 1.3 | 1.1 | 3.1 | 3.1 |
| Aqueous phase MA concentration + organic phase MA concentration (wt %) |  | 8.37% | 25.58% | 51.44% | 59.57% |  |  |
| MA partition coefficient (aqueous phase/organic phase) |  | 0.44 | 0.31 | 0.25 | 0.25 |  |  |

Consideration of Results

The results in Experimental Examples 1 to 10 demonstrate that the AD partition coefficient tends to decrease and the distribution ratio of AD to the organic phase tends to be relatively higher with an increasing AD concentration in the charge liquid and with increasing AD concentrations in the aqueous phase and the organic phase. Specifically, from the viewpoint of acetaldehyde removal efficiency, the AD removing treatment of the organic phase has large advantages at a high AD concentration in at least one of the aqueous phase and the organic phase; but has small advantages at a low AD concentration in at least one of the aqueous phase and the organic phase. In contrast, the AD removing treatment of the aqueous phase has large advantages at a low AD concentration in at least one of the aqueous phase and the organic phase; but has small advantages at a high AD concentration in at least one of the aqueous phase and the organic phase. From another viewpoint, when a step and facilities for the AD removing treatment of the organic phase are employed, the AD concentration in at least one of the aqueous phase and the organic phase in the liquid-liquid separation step is preferably controlled to be high, typically by regulating one or more of conditions such as reaction conditions in the reactor, evaporation conditions in the evaporator, and distillation conditions for the vapor stream from the evaporation step. In contrast, when a step and facilities for the AD removing treatment of the aqueous phase are employed, the AD concentration in at least one of the aqueous phase and the organic phase in the liquid-liquid separation step is preferably controlled to be low, typically by regulating one or more of conditions such as reaction conditions in the reactor, evaporation conditions in the evaporator, and distillation conditions for the vapor stream from the evaporation step.

The results in Experimental Examples 11 to 15 demonstrate that, at a constant AD concentration, the AD partition coefficient tends to decrease and the distribution ratio of AD to the organic phase tends to be relatively higher, with an elevating temperature in the liquid-liquid separation. Specifically, from the viewpoint of acetaldehyde removal efficiency, the AD removing treatment of the organic phase has large advantages at a high temperature in the liquid-liquid separation; but has small advantages at a low temperature in the liquid-liquid separation. In contrast, the AD removing treatment of the aqueous phase has large advantages at a low temperature in the liquid-liquid separation; but has small advantages at a high temperature in the liquid-liquid separation.

The results in Experimental Examples 16 to 21 demonstrate that, at constant AD and MA concentrations, the AD partition coefficient tends to decrease with an elevating temperature in the liquid-liquid separation; and that the distribution ratio of AD to the organic phase tends to be relatively higher with such an elevating temperature even in a system including methyl acetate. Specifically, from the viewpoint of acetaldehyde removal efficiency, the AD removing treatment of the organic phase has large advantages at a high temperature in the liquid-liquid separation; but has small advantages at a low temperature in the liquid-liquid separation. In contrast, the AD removing treatment of the aqueous phase has large advantages at a low temperature in the liquid-liquid separation even in a system including methyl acetate; but has small advantages at a high temperature in the liquid-liquid separation. From another viewpoint, when a step and facilities for the AD removing treatment of the organic phase are employed, the liquid temperature in the liquid-liquid separation is preferably set high in the liquid-liquid separation step; and when a step and facilities for the AD removing treatment of the aqueous phase are employed, the liquid temperature in the liquid-liquid separation is preferably set low in the liquid-liquid separation step, each regardless of the presence or absence of methyl acetate.

The results in Experimental Examples 22 to 26 and Experimental Examples 4 and 17 demonstrate that the AD partition coefficient tends to decrease, and the distribution ratio of AD to the organic phase tends to be relatively higher, with an increasing MA concentration in the charge liquid and with an increasing MA concentration in at least one of the aqueous phase and the organic phase. Specifically, from the viewpoint of acetaldehyde removal efficiency, the AD removing treatment of the organic phase has large advantages at a high MA concentration in at least one of the aqueous phase and the organic phase; but has small advantages at a low MA concentration in at least one of the aqueous phase and the organic phase. In contrast, the AD removing treatment of the aqueous phase has large advantages at a low MA concentration in at least one of the aqueous phase and the organic phase; but has small advantages at a high MA concentration in at least one of the aqueous phase and the organic phase. In view of another aspect, when a step and facilities for the AD removing treatment of the organic phase are employed, the MA concentration in at least one of the aqueous phase and the organic phase in the liquid-liquid separation step is preferably increased, typically by regulating one or more of conditions such as reaction conditions in the reactor, evaporation conditions in the evaporator, and distillation conditions for the vapor stream from the evaporation step; and when a step and facilities for the AD removing treatment of the aqueous phase are employed, the MA concentration in at least one of the aqueous phase and the organic phase in the liquid-liquid separation step is preferably lowered, typically by regulating one or more of conditions such as reaction conditions in the reactor, evaporation conditions in the evaporator, and distillation conditions for the vapor stream from the evaporation step. The results in Experimental Examples 22 to 26 demonstrate that not only the AD partition coefficient, but also the MA partition coefficient decrease with an increasing MA concentration in the charge liquid and with an increasing MA concentration in at least one of the aqueous phase and the organic phase.

The results in Referential Examples 1 and 2 demonstrate that the AD partition coefficient does not so much vary depending on the AC concentrations in the charge liquid, the aqueous phase, and the organic phase. Namely, from the viewpoint of acetaldehyde removal efficiency, there is not so much point in employing the AC concentrations as parameters in comparisons in advantages between the technique of subjecting the organic phase to an AD removing treatment and of the technique of subjecting the aqueous phase to an AD removing treatment.

Next, the present invention will be further illustrated with reference to several examples below. The examples are each on the basis of an exemplary test operation; and conditions, such as chemical compositions and operation conditions, for carrying out the examples are indicated with very specific numerical values. However, these numerical values are never construed to limit the scope of the present invention. The chemical composition in the system is affected by and responds to components such as hydrogen and oxygen and may vary slightly. Accordingly, numerical values for the examples in the tables indicate numerical values at a certain point during the operation.

Comparative Example 1

An experiment as follows was performed in a methanol-carbonylation acetic acid pilot plant (see FIG. 1).

A liquid reaction mixture (400 parts) from a reactor was charged into an evaporator, 25% of which was evaporated (evaporation rate: 25%) with heating of the evaporator. The reactor was operated at a total pressure of 2.8 MPa (absolute pressure), a carbon monoxide partial pressure of 1.4 MPa (absolute pressure), a hydrogen partial pressure of 0.04 MPa (absolute pressure), and a reaction temperature of 187° C. The liquid reaction mixture had a chemical composition of: 7.8% of methyl iodide (MeI), 2.1% of methyl acetate (MA), 2.5% of water ($H_2O$), 910 ppm (in terms of Rh) of a rhodium complex, 14.1% of lithium iodide (LiI), 250 ppm of acetaldehyde (AD), 1.4 ppm of crotonaldehyde (CR), 1.6 ppm of 2-ethylcrotonaldehyde (2ECR), 250 ppm of propionic acid (PA), 40 ppm of formic acid (FA), and 4.8 ppm of butyl acetate (BA), with the remainder being acetic acid (but including trace amounts of impurities). Vapors from the evaporator had a chemical composition of: 28.1% of methyl iodide, 4.9% of methyl acetate, 1.9% of water, 651 ppm of acetaldehyde, 1.5 ppm of crotonaldehyde, 0.23 ppm of 2-ethylcrotonaldehyde, 73 ppm of propionic acid, 85 ppm of formic acid, and 0.7 ppm of butyl acetate, with the remainder being acetic acid (but including trace amounts of impurities). The vapors (100 parts) were charged into a light ends column, where the light ends column had 20 actual plates and was operated at a column top pressure of 250 kPa (absolute pressure) and a column top temperature of 140° C., and where the vapors were charged at the 2nd plate from the bottom. Overhead vapors from the column were condensed to give a condensate, and the condensate was separated into an aqueous phase and an organic phase using a decanter, where the decanter was operated at a temperature of 40° C. and a pressure of 0.13 MPaG. A part (11 parts) of the organic phase was fed to an acetaldehyde-removing column, from which acetaldehyde was separated and removed out of the system, where the acetaldehyde-removing column had 80 actual plates and was operated at a column top pressure of 280 kPa (absolute pressure) and a column top temperature of 52° C., and where the part of the organic phase was charged at the 11th plate from the bottom. Bottoms (11 parts, in approximately the same amount as the charge liquid) after the acetaldehyde removal were recycled to the reaction system. The remainder (41 parts) of the organic phase was directly recycled to the reactor. Of the aqueous phase, a part was refluxed to the light ends column, and the remainder (1.5 parts) was recycled, as a distillate, to the reactor. A reflux ratio was set to 2, where the reflux ratio was defined as the ratio of the aqueous phase reflux amount to the distillate amount. Bottoms (3 parts) were drawn from the column bottom of the light ends column and recycled to the reaction system. A sidecut (SC) stream (65 parts) was drawn from an intermediate portion (4th plate from the bottom) of the light ends column and charged into a dehydration column, where the dehydration column had 50 actual plates and was operated at a column top pressure of 295 kPa (absolute pressure) and a column top temperature of 150° C., and where the sidecut stream was charged at the 34th plate from the bottom. Of an overhead vapor condensate from the dehydration column, a part was refluxed (recycled) to the dehydration column; and the remainder (19 parts) as a distillate was recycled to the reaction system. A reflux ratio at the dehydration column was controlled to 0.3, where the reflux ratio is the ratio of the reflux amount to the distillate amount. As a result, 46 parts of an acetic acid product were obtained as bottoms from the column bottom of the dehydration column. The acetic acid product had a crotonaldehyde content of 0.99 ppm, an 2-ethylcrotonaldehyde content of 0.29 ppm, and a butyl acetate content of 0.76 ppm. The acetic acid product was examined and found to have a permanganate time of 50 minutes. The results are given in Table 3.

Comparative Example 2

An experiment was performed by a procedure similar to that in Comparative Example 1, except for operating the reactor at a hydrogen partial pressure of 0.02 MPa, and operating the decanter at a temperature of −5.2° C. The resulting acetic acid product had a crotonaldehyde content of 2.3 ppm, an 2-ethylcrotonaldehyde content of 1.5 ppm, and a butyl acetate content of 1.8 ppm. The acetic acid product was examined and found to have a permanganate time of 10 minutes. The results are given in Table 3.

Comparative Example 3

An experiment was performed by a procedure similar to that in Comparative Example 1, except for operating the dehydration column at a reflux ratio of 0.05. The resulting acetic acid product had a crotonaldehyde content of 1.1 ppm, an 2-ethylcrotonaldehyde content of 0.28 ppm, and a butyl acetate content of 0.72 ppm. The acetic acid product was examined and found to have a permanganate time of 40 minutes. The results are given in Table 3.

Example 1

An experiment was performed by a procedure similar to that in Comparative Example 1, except following conditions. Specifically, the decanter was operated at a temperature of −5.2° C. to separate the condensate into an aqueous phase and an organic phase. On the basis of the acetaldehyde partition coefficient, a part (11 parts) of the organic phase was fed to the acetaldehyde-removing column, from which acetaldehyde was separated and removed out of the system, where the acetaldehyde-removing column had 80 actual plates and was operated at a column top pressure of 280 kPa (absolute pressure) and a column top temperature of 52° C., and where the part of the organic phase was charged at the 11th plate from the bottom. Bottoms (11 parts, in approximately the same amount as the charge liquid) after the acetaldehyde removal were recycled to the reaction system. Of 41 parts of the organic phase, which were recycled directly to the reactor in Comparative Example 1, 20 parts were charged into a crotonaldehyde-removing column, and 21 parts were directly recycled to the reactor. The organic phase had a chemical composition of: 0.3% of alkanes, 1300 ppm of acetaldehyde, 12.5% of methyl acetate, 0.7% of water, 1.9% of acetic acid, 1.7 ppm of crotonaldehyde, 0.1 ppm of 2-ethylcrotonaldehyde, and 0.3 ppm of butyl acetate, with the remainder being methyl iodide (but including trace amounts of impurities). The crotonaldehyde-removing column was a packed column, had 10 theoretical plates, and was operated at a column top pressure of 280 kPa (absolute pressure) and a column top temperature of 52° C., where the 20 parts of the organic phase were charged at the 5th theoretical plate from the bottom. The crotonaldehyde-removing column was operated at a reflux ratio of 0.01, to distill 19.48 parts as a distillate. The distillate had a chemical composition of: 1305 ppm of acetaldehyde, 12.5% of methyl acetate, 0.7% of water, 0.1% of acetic acid, 1.5 ppm of crotonaldehyde, 0.05 ppm of 2-ethylcrotonaldehyde, and 0.2 ppm of butyl acetate, with the remainder being methyl iodide (but including trace amounts of impurities). The distillate was circulated to the decanter, and 0.52 part of bottoms was drawn from the column bottom, where the bottoms had a chemical composition of: 2.1% of methyl acetate, 1.5% of water, 5.5% of methyl iodide, 6.5 ppm of crotonaldehyde, 13.3 ppm of 2-ethylcrotonaldehyde, 6.9 ppm of butyl acetate, and 1.2% of alkanes, with the remainder being acetic acid (but including trace amounts of impurities). These changes caused changes in chemical compositions of process liquids. The resulting acetic acid product obtained as bottoms from the column bottom of the dehydration column had a crotonaldehyde content of 0.92 ppm, an 2-ethylcrotonaldehyde content of 0.27 ppm, and a butyl acetate content of 0.71 ppm. The acetic acid product was examined and found to have a permanganate time of 70 minutes. The results are given in Table 3.

Example 2

An experiment was performed by a procedure similar to that in Example 1, except for operating the decanter at a temperature of 11.0° C., operating the light ends column at a reflux ratio of 15, and operating the dehydration column at a reflux ratio of 10. These changes caused changes in chemical compositions of process liquids. The resulting acetic acid product from the column bottom of the dehydration column had a crotonaldehyde content of 0.23 ppm, an 2-ethylcrotonaldehyde content of 0.56 ppm, and a butyl acetate content of 2.1 ppm. The acetic acid product was examined and found to have a permanganate time of 200 minutes. The results are given in Table 3.

Example 3

An experiment was performed by a procedure similar to that in Example 2, except for operating the decanter at a temperature of 22° C., and operating the crotonaldehyde-removing column at a reflux ratio of 0.1. These changes caused changes in chemical compositions of process liquids. The changes also caused the distillate amount and the bottoms amount at the crotonaldehyde-removing column to be changed respectively to 19.52 parts and 0.48 part. This is because water, which would be distilled at the column top without the changes, was separated more efficiently to the bottoms. The resulting acetic acid product from the column bottom of the dehydration column had a crotonaldehyde content of 0.21 ppm, an 2-ethylcrotonaldehyde content of 0.55 ppm, and a butyl acetate content of 2 ppm. The acetic acid product was examined and found to have a permanganate time of 220 minutes. The results are given in Table 3.

Example 4

An experiment was performed by a procedure similar to that in Example 2, except for operating the decanter at a temperature of 29° C., and operating the crotonaldehyde-removing column at a reflux ratio of 1. These changes caused changes in chemical compositions of process liquids. The changes also caused the distillate amount and the bottoms amount at the crotonaldehyde-removing column to be changed respectively to 19.56 parts and 0.44 part. This is because water, which would be distilled at the column top without the changes, was separated more efficiently to the bottoms. The resulting acetic acid product from the column bottom of the dehydration column had a crotonaldehyde content of 0.19 ppm, an 2-ethylcrotonaldehyde content of 0.4 ppm, and a butyl acetate content of 1.8 ppm. The acetic acid product was examined and found to have a permanganate time of 280 minutes. The results are given in Table 3.

Example 5

An experiment was performed by a procedure similar to that in Example 2, except for operating the decanter at a temperature of 40.8° C., and operating the crotonaldehyde-removing column at a reflux ratio of 10. These changes caused changes in chemical compositions of process liquids. The changes also caused the distillate amount and the bottoms amount at the crotonaldehyde-removing column to be changed respectively to 19.6 parts and 0.4 part. This is because water, which would be distilled at the column top without the changes, was separated more efficiently to the bottoms. The resulting acetic acid product from the column bottom of the dehydration column had a crotonaldehyde content of 0.15 ppm, an 2-ethylcrotonaldehyde content of 0.28 ppm, and a butyl acetate content of 1.8 ppm. The acetic acid product was examined and found to have a permanganate time of 360 minutes. The results are given in Table 3.

Example 6

An experiment was performed by a procedure similar to that in Example 2, except for operating the decanter at a temperature of 49.9° C., and operating the crotonaldehyde-removing column at a reflux ratio of 50. These changes caused changes in chemical compositions of process liquids. The changes also caused the distillate amount and the bottoms amount at the crotonaldehyde-removing column to be changed respectively to 19.6 parts and 0.4 part. This is because water, which would be distilled at the column top without the changes, was separated more efficiently to the bottoms. The resulting acetic acid product from the column bottom of the dehydration column had a crotonaldehyde content of 0.09 ppm, an 2-ethylcrotonaldehyde content of 0.14 ppm, and a butyl acetate content of 1.6 ppm. The acetic acid product was examined and found to have a permanganate time of 450 minutes. The results are given in Table 4.

Example 7

An experiment was performed by a procedure similar to that in Example 5, except for operating the decanter at a temperature of 40.2° C., selecting the organic phase and feeding the organic phase to the acetaldehyde-removing column in an amount of 11 parts, wherein the selection was performed on the basis of the temperature upon the liquid-liquid separation of the light ends column overhead condensate, changing the methyl acetate concentration in the light ends column charge, and changing the methyl acetate concentration and the AD partition coefficient in the decanter. These changes caused changes in chemical compositions of process liquids. The resulting acetic acid product obtained as bottoms from the column bottom of the dehydration column had a crotonaldehyde content of 0.3 ppm, an 2-ethylcrotonaldehyde content of 0.56 ppm, and a butyl acetate content of 2.2 ppm. The acetic acid product was examined and found to have a permanganate time of 150 minutes. The results are given in Table 4.

Example 8

An experiment was performed by a procedure similar to that in Example 5, except for operating the decanter at a temperature of 40.5° C., changing the methyl acetate concentration in the light ends column charge, and changing the methyl acetate concentration and the AD partition coefficient in the decanter. These changes caused changes in chemical compositions of process liquids. The resulting acetic acid product obtained as bottoms from the column bottom of the dehydration column had a crotonaldehyde content of 0.22 ppm, an 2-ethylcrotonaldehyde content of 0.53 ppm, and a butyl acetate content of 2 ppm. The acetic acid product was examined and found to have a permanganate time of 220 minutes. The results are given in Table 4.

Example 9

An experiment was performed by a procedure similar to that in Example 5, except for operating the decanter at a temperature of 39.9° C., changing the methyl acetate concentration in the light ends column charge, and changing the methyl acetate concentration and the AD partition coefficient in the decanter. These changes caused changes in chemical compositions of process liquids. The resulting acetic acid product obtained as bottoms from the column bottom of the dehydration column had a crotonaldehyde content of 0.18 ppm, an 2-ethylcrotonaldehyde content of 0.28 ppm, and a butyl acetate content of 1.7 ppm. The acetic acid product was examined and found to have a permanganate time of 290 minutes. The results are given in Table 4.

Example 10

An experiment was performed by a procedure similar to that in Example 5, except for operating the decanter at a temperature of 40.7° C., changing the methyl acetate concentration in the light ends column charge, and changing the methyl acetate concentration and the AD partition coefficient in the decanter. These changes caused changes in chemical compositions of process liquids. The resulting acetic acid product obtained as bottoms from the column bottom of the dehydration column had a crotonaldehyde content of 0.12 ppm, an 2-ethylcrotonaldehyde content of 0.26 ppm, and a butyl acetate content of 1.6 ppm. The acetic acid product was examined and found to have a permanganate time of 400 minutes. The results are given in Table 4.

Example 11

An experiment was performed by a procedure similar to that in Example 5, except for operating the decanter at a temperature of 40.1° C., changing the methyl acetate concentration in the light ends column charge, and changing the methyl acetate concentration and the AD partition coefficient in the decanter. These changes caused changes in chemical compositions of process liquids. The resulting acetic acid product obtained as bottoms from the column bottom of the dehydration column had a crotonaldehyde content of 0.07 ppm, an 2-ethylcrotonaldehyde content of 0.14 ppm, and a butyl acetate content of 1.4 ppm. The acetic acid product was examined and found to have a permanganate time of longer than 540 minutes. The results are given in Table 4.

Example 12

An experiment was performed by a procedure similar to that in Example 1, except for operating the reactor at a hydrogen partial pressure of 0.07 MPa, and operating the decanter at a temperature of −5.3° C. These changes caused changes in chemical compositions of process liquids. The resulting acetic acid product obtained as bottoms from the column bottom of the dehydration column had a crotonaldehyde content of 0.85 ppm, an 2-ethylcrotonaldehyde content of 0.29 ppm, and a butyl acetate content of 0.85 ppm. The acetic acid product was examined and found to have a permanganate time of 80 minutes. The results are given in Table 4.

Example 13

An experiment was performed by a procedure similar to that in Example 1, except for operating the decanter at a temperature of 40.1° C. This change caused changes in chemical compositions of process liquids. The resulting acetic acid product obtained as bottoms from the column bottom of the dehydration column had a crotonaldehyde content of 0.8 ppm, an 2-ethylcrotonaldehyde content of 0.26 ppm, and a butyl acetate content of 0.68 ppm. The acetic acid product was examined and found to have a permanganate time of 90 minutes. The results are given in Table 4.

Example 14

An experiment was performed by a procedure similar to that in Example 6, except for operating the decanter at a temperature of 40.3° C., changing the methyl acetate concentration in the light ends column charge, changing the methyl acetate concentration and the AD partition coefficient in the decanter, and selecting the aqueous phase and feeding the aqueous phase to the acetaldehyde-removing column in an amount of 11 parts, where the selection was performed on the basis of the temperature in liquid-liquid separation of the light ends column overhead condensate. These changes caused changes in chemical compositions of process liquids. The resulting acetic acid product obtained as bottoms from the column bottom of the dehydration column had a crotonaldehyde content of 0.08 ppm, an 2-ethylcrotonaldehyde content of 0.12 ppm, and a butyl acetate content of 1.3 ppm. The acetic acid product was examined and found to have a permanganate time of 530 minutes. The results are given in Table 4.

In Tables 3 and 4, "$C_{OR}$" represents the crotonaldehyde concentration, "$C_=$" represents the 2-ethylcrotonaldehyde concentration, "$C_{BA}$" represents the butyl acetate concentration, "AD" represents acetaldehyde, "MeI" represents methyl iodide, "MA" represents methyl acetate, and "AC" represents acetic acid. The numerical values regarding components represent concentrations. The "Distillate [CR]/charge liquid [CR]" represents the ratio of the crotonaldehyde concentration (ppm by mass) in the distillate to the crotonaldehyde concentration (ppm by mass) in the charge liquid. The "Bottoms [CR]/charge liquid [CR]" represents the ratio of the crotonaldehyde concentration (ppm by mass) in the bottoms to the crotonaldehyde concentration (ppm by mass) in the charge liquid.

TABLE 3

| | | | Comparative Examples | | | Examples | | | | |
|---|---|---|---|---|---|---|---|---|---|---|
| | | | 1 | 2 | 3 | 1 | 2 | 3 | 4 | 5 |
| Hydrogen partial pressure in reactor (MPa) | | | 0.04 | 0.02 | 0.04 | 0.04 | 0.04 | 0.04 | 0.04 | 0.04 |
| Reflux ratio at light ends column | | | 2 | 2 | 2 | 2 | 15 | 15 | 15 | 15 |
| Reflux ratio at dehydration column | | | 0.3 | 0.3 | 0.05 | 0.3 | 10 | 10 | 10 | 10 |
| Reflux ratio at crotonaldehyde-removing column | | | (note 2) | (note 2) | (note 2) | 0.01 | 0.01 | 0.1 | 1 | 10 |
| Liquid reaction mixture | | $C_{CR}$ | 1.4 | 2.9 | 1.3 | 1.1 | 1.2 | 1.1 | 1 | 0.9 |
| (ppm) | | $C_{ECR}$ | 1.6 | 3.3 | 1.6 | 1.4 | 1.5 | 1.3 | 1.3 | 1.2 |
| | | $C_{BA}$ | 4.8 | 8.1 | 4.8 | 4.4 | 9.0 | 8.7 | 8.2 | 8.0 |
| Light ends | (ppm) | $C_{CR}$ | 1.5 | 3.2 | 1.4 | 1.4 | 1.5 | 1.1 | 1.1 | 1 |
| column | | $C_{ECR}$ | 0.23 | 0.47 | 0.2 | 0.22 | 0.33 | 0.30 | 0.29 | 0.28 |
| charge | | $C_{BA}$ | 0.7 | 1.5 | 0.6 | 1.2 | 1.4 | 1.3 | 1.1 | 1.1 |
| | (wt %) | AD | 0.07 | 0.11 | 0.07 | 0.07 | 0.07 | 0.07 | 0.07 | 0.07 |
| | | MeI | 28.0 | 27.9 | 28.2 | 28.4 | 27.9 | 28.0 | 27.8 | 28.2 |
| | | MA | 4.9 | 5.0 | 5.1 | 5.0 | 4.8 | 4.9 | 4.7 | 4.8 |
| | | $H_2O$ | 1.9 | 1.9 | 2.0 | 2.0 | 1.9 | 2.1 | 1.8 | 2.0 |
| | | AC | 63.9 | 63.9 | 63.9 | 63.4 | 64.3 | 63.7 | 64.7 | 63.8 |
| | | Others | 1.2 | 1.3 | 1.3 | 1.1 | 1.0 | 1.2 | 0.9 | 1.1 |
| | | Total | 100.0 | 100.0 | 100.0 | 100.0 | 100.0 | 100.0 | 100.0 | 100.0 |
| Decanter | Temperature | (° C.) | 40.0 | −5.2 | 39.8 | −5.2 | 11.0 | 22.0 | 29.0 | 40.8 |
| | Pressure | (MPaG) | 0.13 | 0.13 | 0.13 | 0.13 | 0.13 | 0.13 | 0.13 | 0.13 |
| | Aqueous | AD | (note 1) | (note 1) | (note 1) | 0.55 | 0.48 | 0.42 | 0.38 | 0.34 |
| | phase | MeI | (note 1) | (note 1) | (note 1) | 3.2 | 3.4 | 3.1 | 3.3 | 3.3 |
| | (wt %) | MA | (note 1) | (note 1) | (note 1) | 6.4 | 6.1 | 6.3 | 6.0 | 6.1 |
| | | $H_2O$ | (note 1) | (note 1) | (note 1) | 69.8 | 70.8 | 70.5 | 71.6 | 71.0 |
| | | AC | (note 1) | (note 1) | (note 1) | 19.1 | 18.4 | 18.8 | 18.0 | 18.4 |
| | | Others | (note 1) | (note 1) | (note 1) | 0.9 | 0.8 | 1.0 | 0.7 | 0.8 |
| | | Total | (note 1) | (note 1) | (note 1) | 100.0 | 100.0 | 100.0 | 100.0 | 100.0 |
| | Organic | AD | (note 1) | (note 1) | (note 1) | 0.15 | 0.16 | 0.16 | 0.17 | 0.17 |
| | phase | MeI | (note 1) | (note 1) | (note 1) | 62.2 | 63.0 | 63.1 | 63.8 | 63.5 |
| | (wt %) | MA | (note 1) | (note 1) | (note 1) | 14.8 | 14.5 | 14.4 | 14.2 | 14.3 |
| | | $H_2O$ | (note 1) | (note 1) | (note 1) | 0.7 | 0.6 | 0.7 | 0.6 | 0.6 |
| | | AC | (note 1) | (note 1) | (note 1) | 21.0 | 20.3 | 20.7 | 20.0 | 20.3 |
| | | Others | (note 1) | (note 1) | (note 1) | 1.1 | 1.4 | 1.0 | 1.2 | 1.1 |
| | | Total | (note 1) | (note 1) | (note 1) | 100.0 | 100.0 | 100.0 | 100.0 | 100.0 |
| | AD partition coefficient (aqueous phase/organic phase) | | (note 1) | (note 1) | (note 1) | 3.6 | 3.0 | 2.6 | 2.3 | 2.0 |
| | Aqueous phase MA concentration + organic phase MA concentration (wt %) | | (note 1) | (note 1) | (note 1) | 21.2 | 20.6 | 20.7 | 20.2 | 20.4 |
| | MA partition coefficient (aqueous phase/organic phase) | | (note 1) | (note 1) | (note 1) | 0.43 | 0.42 | 0.43 | 0.42 | 0.43 |

TABLE 3-continued

|  |  | Comparative Examples | | | Examples | | | | |
| --- | --- | --- | --- | --- | --- | --- | --- | --- | --- |
|  |  | 1 | 2 | 3 | 1 | 2 | 3 | 4 | 5 |
| Sidecut liquid from light ends column (ppm) | $C_{CR}$ | 1.1 | 2.5 | 1.1 | 0.9 | 0.4 | 0.4 | 0.3 | 0.2 |
|  | $C_{ECR}$ | 0.2 | 1.1 | 0.2 | 0.2 | 0.4 | 0.4 | 0.3 | 0.2 |
|  | $C_{BA}$ | 0.6 | 1.2 | 0.5 | 0.6 | 1.6 | 1.4 | 1.2 | 1.1 |
|  | $C_{CR}/C_{ECR}$ | 5.5 | 2.3 | 5.5 | 4.5 | 1.0 | 1.0 | 1.0 | 1.0 |
|  | $C_{CR}/C_{BA}$ | 1.8 | 2.1 | 2.2 | 1.5 | 0.3 | 0.3 | 0.3 | 0.2 |
| Crotonaldehyde-removing column (ppm) | Charge liquid CR | (note 2) | (note 2) | (note 2) | 1.7 | 2.8 | 2.8 | 2.8 | 2.7 |
|  | Distillate CR | (note 2) | (note 2) | (note 2) | 1.5 | 2.6 | 2.4 | 1 | 0.3 |
|  | Bottoms CR | (note 2) | (note 2) | (note 2) | 6.5 | 7.7 | 18 | 82 | 109 |
|  | Distillate [CR]/charge liquid [CR] | (note 2) | (note 2) | (note 2) | 0.88 | 0.93 | 0.86 | 0.36 | 0.11 |
|  | Bottoms [CR]/charge liquid [CR] | (note 2) | (note 2) | (note 2) | 3.8 | 2.8 | 6.4 | 29 | 40 |
| Bottoms from dehydration column (product) (ppm) | $C_{CR}$ | 0.99 | 2.3 | 1.1 | 0.92 | 0.23 | 0.21 | 0.19 | 0.15 |
|  | $C_{ECR}$ | 0.29 | 1.5 | 0.28 | 0.27 | 0.56 | 0.55 | 0.4 | 0.28 |
|  | $C_{BA}$ | 0.76 | 1.8 | 0.72 | 0.71 | 2.1 | 2 | 1.8 | 1.8 |
|  | $C_{CR}/C_{ECR}$ | 3.4 | 1.5 | 3.9 | 3.4 | 0.4 | 0.4 | 0.5 | 0.5 |
|  | $C_{CR}/C_{BA}$ | 1.3 | 1.3 | 1.5 | 1.3 | 0.1 | 0.1 | 0.1 | 0.1 |
| Product permanganate time (min) |  | 50 | 10 | 40 | 70 | 200 | 220 | 280 | 360 |

(note 1): Unmeasured
(note 2): The step is not performed.
Since numbers are rounded off to the significant figures, the total may not be 100 (wt %).

TABLE 4

|  |  |  | Examples | | | | | | | | |
| --- | --- | --- | --- | --- | --- | --- | --- | --- | --- | --- | --- |
|  |  |  | 6 | 7 | 8 | 9 | 10 | 11 | 12 | 13 | 14 |
| Hydrogen partial pressure in reactor (MPa) |  |  | 0.04 | 0.04 | 0.04 | 0.04 | 0.04 | 0.04 | 0.07 | 0.04 | 0.04 |
| Reflux ratio at light ends column |  |  | 15 | 15 | 15 | 15 | 15 | 15 | 2 | 2 | 15 |
| Reflux ratio at dehydration column |  |  | 10 | 10 | 10 | 10 | 10 | 10 | 0.3 | 0.3 | 10 |
| Reflux ratio at crotonaldehyde-removing column |  |  | 50 | 10 | 10 | 10 | 10 | 10 | 0.01 | 0.01 | 50 |
| Liquid reaction mixture (ppm) | $C_{CR}$ |  | 0.8 | 1.2 | 1.1 | 1 | 0.8 | 0.7 | 1 | 1.1 | 0.7 |
|  | $C_{ECR}$ |  | 1.1 | 1.5 | 1.3 | 1.2 | 1.1 | 1 | 1.3 | 1.4 | 1 |
|  | $C_{BA}$ |  | 7.8 | 8.5 | 8.3 | 8.2 | 7.9 | 7.6 | 4.7 | 4.4 | 7.5 |
| Light ends column charge | (ppm) | $C_{CR}$ | 0.9 | 1.3 | 1.2 | 1.1 | 0.9 | 0.7 | 1.2 | 1.4 | 0.8 |
|  |  | $C_{ECR}$ | 0.26 | 0.33 | 0.34 | 0.30 | 0.25 | 0.21 | 0.22 | 0.22 | 0.20 |
|  |  | $C_{BA}$ | 1.0 | 1.2 | 1.2 | 1.1 | 1.0 | 0.9 | 1.5 | 1.2 | 0.9 |
|  | (wt %) | AD | 0.07 | 0.07 | 0.07 | 0.07 | 0.07 | 0.07 | 0.07 | 0.07 | 0.07 |
|  |  | MeI | 27.8 | 28.4 | 28.0 | 27.7 | 27.7 | 28.4 | 27.9 | 28.2 | 28.5 |
|  |  | MA | 4.9 | 1.3 | 2.2 | 3.1 | 6.0 | 6.5 | 4.7 | 4.9 | 6.5 |
|  |  | $H_2O$ | 2.1 | 1.9 | 1.9 | 2.0 | 2.1 | 1.8 | 2.0 | 2.0 | 1.9 |
|  |  | AC | 64.1 | 67.0 | 66.4 | 66.2 | 62.9 | 62.1 | 64.1 | 63.7 | 62.0 |
|  |  | Others | 1.0 | 1.3 | 1.4 | 0.9 | 1.2 | 1.1 | 1.2 | 1.1 | 1.0 |
|  |  | Total | 100.0 | 100.0 | 100.0 | 100.0 | 100.0 | 100.0 | 100.0 | 100.0 | 100.0 |
| Decanter | Temperature | (° C.) | 49.9 | 40.2 | 40.5 | 39.9 | 40.7 | 40.1 | −5.3 | 40.1 | 40.3 |
|  | Pressure | (MPaG) | 0.13 | 0.13 | 0.13 | 0.13 | 0.13 | 0.13 | 0.13 | 0.13 | 0.13 |
|  | Aqueous phase (wt %) | AD | 0.30 | 0.62 | 0.54 | 0.41 | 0.28 | 0.20 | 0.51 | 0.34 | 0.20 |
|  |  | MeI | 3.2 | 3.3 | 3.4 | 3.0 | 3.5 | 3.2 | 3.3 | 3.2 | 3.2 |
|  |  | MA | 6.3 | 1.7 | 2.8 | 4.0 | 7.7 | 8.3 | 6.0 | 6.3 | 8.3 |
|  |  | $H_2O$ | 70.6 | 88.6 | 83.8 | 79.8 | 64.8 | 62.4 | 71.4 | 70.5 | 62.4 |
|  |  | AC | 18.8 | 5.0 | 8.4 | 11.9 | 23.0 | 24.9 | 18.0 | 18.8 | 24.9 |
|  |  | Others | 0.9 | 0.8 | 1.0 | 1.0 | 0.8 | 1.0 | 0.8 | 0.9 | 1.0 |
|  |  | Total | 100.0 | 100.0 | 100.0 | 100.0 | 100.0 | 100.0 | 100.0 | 100.0 | 100.0 |
|  | Organic phase (wt %) | AD | 0.18 | 0.14 | 0.15 | 0.17 | 0.18 | 0.19 | 0.16 | 0.17 | 0.19 |
|  |  | MeI | 62.8 | 88.3 | 81.3 | 74.7 | 53.5 | 45.9 | 64.0 | 62.9 | 45.9 |
|  |  | MA | 14.4 | 2.9 | 5.7 | 8.8 | 20.2 | 25.9 | 14.0 | 14.5 | 25.9 |
|  |  | $H_2O$ | 0.6 | 0.5 | 0.5 | 0.5 | 0.7 | 0.8 | 0.6 | 0.7 | 0.8 |
|  |  | AC | 20.7 | 7.2 | 10.9 | 14.3 | 24.3 | 25.9 | 20.0 | 20.7 | 25.9 |
|  |  | Others | 1.3 | 1.0 | 1.4 | 1.5 | 1.1 | 1.3 | 1.2 | 1.1 | 1.3 |
|  |  | Total | 100.0 | 100.0 | 100.0 | 100.0 | 100.0 | 100.0 | 100.0 | 100.0 | 100.0 |
|  | AD partition coefficient (aqueous phase/organic phase) |  | 1.7 | 4.3 | 3.6 | 2.5 | 1.6 | 1.1 | 3.3 | 2.0 | 1.1 |
|  | Aqueous phase MA concentration + organic phase MA concentration (wt %) |  | 20.7 | 4.5 | 8.5 | 12.8 | 27.8 | 34.2 | 20.0 | 20.8 | 34.2 |
|  | MA partition coefficient (aqueous phase/organic phase) |  | 0.43 | 0.58 | 0.49 | 0.45 | 0.38 | 0.32 | 0.43 | 0.43 | 0.32 |
| Sidecut liquid from light ends column (ppm) | $C_{CR}$ |  | 0.1 | 0.5 | 0.4 | 0.3 | 0.2 | 0.1 | 0.9 | 0.9 | 0.1 |
|  | $C_{ECR}$ |  | 0.1 | 0.4 | 0.4 | 0.2 | 0.2 | 0.1 | 0.2 | 0.2 | 0.1 |
|  | $C_{BA}$ |  | 1.0 | 1.5 | 1.4 | 1.3 | 1.0 | 0.9 | 0.8 | 0.6 | 0.9 |
|  | $C_{CR}/C_{ECR}$ |  | 1.0 | 1.3 | 1.0 | 1.5 | 1.0 | 1.0 | 4.5 | 4.5 | 1.0 |
|  | $C_{CR}/C_{BA}$ |  | 0.1 | 0.3 | 0.3 | 0.2 | 0.2 | 0.1 | 1.1 | 1.5 | 0.1 |

TABLE 4-continued

|  |  | Examples | | | | | | | | |
| --- | --- | --- | --- | --- | --- | --- | --- | --- | --- | --- |
|  |  | 6 | 7 | 8 | 9 | 10 | 11 | 12 | 13 | 14 |
| Crotonaldehyde-removing column (ppm) | Charge liquid CR | 2.6 | 2.6 | 2.6 | 2.6 | 2.5 | 2.5 | 1.7 | 1.7 | 2.5 |
|  | Distillate CR | 0.01 | 0.1 | 0.1 | 0.1 | 0.1 | 0.1 | 1.4 | 1.5 | 0.1 |
|  | Bottoms CR | 120 | 119 | 118 | 120 | 119 | 120 | 6.6 | 6.5 | 119 |
|  | Distillate [CR]/charge liquid [CR] | 0.04 | 0.04 | 0.04 | 0.04 | 0.04 | 0.04 | 0.82 | 0.88 | 0.04 |
|  | Bottoms [CR]/charge liquid [CR] | 48 | 48 | 48 | 48 | 48 | 48 | 3.9 | 3.8 | 48 |
| Bottoms from dehydration column (product) (ppm) | $C_{CR}$ | 0.09 | 0.3 | 0.22 | 0.18 | 0.12 | 0.07 | 0.85 | 0.8 | 0.08 |
|  | $C_{ECR}$ | 0.14 | 0.56 | 0.53 | 0.28 | 0.26 | 0.14 | 0.29 | 0.26 | 0.12 |
|  | $C_{BA}$ | 1.6 | 2.2 | 2 | 1.7 | 1.6 | 1.4 | 0.85 | 0.68 | 1.3 |
|  | $C_{CR}/C_{ECR}$ | 0.6 | 0.5 | 0.4 | 0.6 | 0.5 | 0.5 | 2.9 | 3.1 | 0.7 |
|  | $C_{CR}/C_{BA}$ | 0.1 | 0.1 | 0.1 | 0.1 | 0.1 | 0.1 | 1.0 | 1.2 | 0.1 |
| Product permanganate time (min) |  | 450 | 150 | 220 | 290 | 400 | >540 | 80 | 90 | 530 |

Since numbers are rounded off to the significant figures, the total may not be 100 (wt %).

Consideration of Results Comparative Examples 1 to 3 are examples in which the crotonaldehyde-removing step was not performed, and the organic phase was merely employed as an object (aqueous phase or organic phase) to be subjected to the acetaldehyde-removing treatment after the liquid-liquid separation, without selection on the basis of a factor or factors such as the AD partition coefficient. As compared with Comparative Example 1, Comparative Example 2 employed a lower hydrogen partial pressure, and this reduced the proportion of crotonaldehyde (CR) to be hydrogenated and, as a result, reduced the decomposition of CR. In addition, Comparative Example 2 employed a lower temperature (−5.2° C.) at the decanter in the liquid-liquid separation step. This probably lowered the AD concentration in the organic phase, reduced the AD removing amount, and caused the acetic acid product to have a higher crotonaldehyde concentration. Probably as a result of these, the acetic acid product according to Comparative Example 2 had a significantly lower (shorter) permanganate time as compared with Comparative Example 1.

Comparative Example 3 is an example in which operations were performed under conditions similar to those in Comparative Example 1, except for operating the dehydration column at a reflux ratio of 0.05. In Comparative Example 3, the dehydration column was operated at a low reflux ratio as low as one-sixths that in Comparative Example 1, thus failed to allow crotonaldehyde flowing into the dehydration column to be concentrated at the column top sufficiently. This caused little decrease in crotonaldehyde concentration in the second acetic acid stream. Comparative Example 3 therefore gave an inferior product permanganate time to Comparative Example 1.

As compared with Comparative Example 3, Comparative Example 2 employed a high reflux ratio at the dehydration column of 0.3, six times as much as the reflux ratio (0.05) in Comparative Example 3, but gave a lower (shorter) product permanganate time. The reason why the effect of the increase in reflux ratio at the dehydration column was canceled was investigated by detailed comparisons on operation conditions. As a result, the cancelation was caused probably because Comparative Example 2 employed the low temperature (−5.2° C.) at the decanter. Specifically, it was conjectured that Comparative Example 2 employed a low decanter temperature, this lowered the acetaldehyde concentration in the organic phase and lowered the amount of acetaldehyde removal; and this increased not only the crotonaldehyde concentration in the sidecut liquid (first acetic acid stream) from the light ends column, but also the crotonaldehyde concentration in the acetic acid product. Probably as a result of this, the acetic acid product according to Comparative Example 2 gave an inferior permanganate time to Comparative Example 3. These results demonstrated that mere increase in reflux ratio at the dehydration column is insufficient for efficiently allowing the acetic acid product to have better quality; but control of the temperature condition (liquid temperature in the liquid-liquid separation) in the decanter serves as one of parameters effective for acetaldehyde-removing treatment with good efficiency.

Comparisons between Comparative Example 2 and Example 1 demonstrate that the second acetic acid stream (dehydration column bottoms) has a CR concentration lowered to one half or less and has a significantly better product permanganate time (as long as 7 times) by synergistic effects of: selecting the object to be subjected to the AD removing treatment on the basis of a factor or factors such as the AD partition coefficient in the liquid-liquid separation step; controlling the CR concentration in the first acetic acid stream to 2.2 ppm or less; and operating the crotonaldehyde-removing column at a reflux ratio of 0.01 or more. According to Example 1, the hydrogen partial pressure in the reactor is increased twice (0.04 MPa) as much as that in Comparative Example 2, so as to control the CR concentration in the first acetic acid stream. This is because of such a mechanism that the increase in hydrogen partial pressure in the reactor causes crotonaldehyde to be hydrogenated, thereby allows the liquid reaction mixture (liquid phase of the reaction mixture; reaction medium) to have a lower CR concentration, and allows the charge liquid to the first distillation column to have a lower CR concentration; and this causes the first acetic acid stream to have a lower CR concentration, where the first acetic acid stream results from light ends removal in the first distillation column.

Comparisons between Example 1 (0.04 MPa) and Example 12 (0.07 MPa) demonstrate that the product permanganate time further increases at a still higher hydrogen partial pressure in the reactor. This is also because of a mechanism as described above.

Comparisons between Comparative Example 3 and Example 1 demonstrate as follows. The acetic acid product has a lower CR concentration and has a better product permanganate time of 70 minutes, about 2 times (1.75 times), by synergistic effects of: selecting an object to be subjected to the AD removing treatment on the basis of a factor or factors such as the AD partition coefficient in the liquid-liquid separation step; controlling the CR concentration in the first acetic acid stream to 2.2 ppm or less;

operating the dehydration column with a reflux ratio at a specific level or higher; and operating the light ends column and the crotonaldehyde-removing column with reflux ratios under specific conditions. The comparisons also demonstrate that, as compared with Comparative Example 3, Example 1 gave lower ratios ($C_{CR}/C_{ECR}$) of the crotonaldehyde concentration $C_{CR}$ (ppm by mass) to the 2-ethylcrotonaldehyde concentration $C_{ECR}$ (ppm by mass) both in the first acetic acid stream and the second acetic acid stream.

Comparisons between Example 1 and Example 2 demonstrate that the acetic acid product has a significantly better permanganate time by increasing the reflux ratios at the light ends column and at the dehydration column, even under common operation conditions for the crotonaldehyde-removing column. The comparisons also demonstrate that, as compared with Example 1, the first acetic acid stream and the second acetic acid stream according to Example 2 each have a significantly lower ratio ($C_{CR}/C_{ECR}$) of the crotonaldehyde concentration $C_{CR}$ (ppm by mass) to the 2-ethylcrotonaldehyde concentration $C_{ECR}$ (ppm by mass), by the working of the separation step.

Comparisons among Examples 2 to 6 demonstrate that the acetic acid product has a better permanganate time by operating the crotonaldehyde-removing column at a higher reflux ratio and thereby allowing crotonaldehyde to be more concentrated at the column bottom of the crotonaldehyde-removing column to increase the amount of crotonaldehyde to be discarded, even under common conditions for the reflux ratio at the light ends column and for the reflux ratio at the dehydration column.

Examples 1 and 2 employ distillation in the crotonaldehyde-removing column performed at an extremely low reflux ratio of 0.01 as compared with ordinary distillation. This distillation, however, causes almost all of the charge liquid to be distilled, gives a distillate in an amount approximately equal to the amount of the charge liquid, and contributes to separation of crotonaldehyde even at such a small reflux amount (reflux ratio). Example 6 could successfully lower the methyl iodide concentration in the bottoms down to the utmost limit, and could lower the discharge amount of useful methyl iodide.

The results in Examples 1 to 6 demonstrate that, with an elevating temperature in the liquid-liquid separation at constant AD and MA concentrations in the light ends column charge liquid, the AD partition coefficient tends to decrease, and the distribution ratio of AD to the organic phase tends to be relatively higher even in a system including methyl acetate. Specifically, from the viewpoint of acetaldehyde removal efficiency, the AD removing treatment of the organic phase has large advantages at a high temperature in the liquid-liquid separation; but has small advantages at a low temperature in the liquid-liquid separation. In contrast, the AD removing treatment of the aqueous phase has large advantages at a low temperature in the liquid-liquid separation even in a system including methyl acetate; but has small advantages at a high temperature in the liquid-liquid separation. From another viewpoint, when a step and facilities for the AD removing treatment of the organic phase are employed, the liquid temperature in the liquid-liquid separation is preferably set high in the liquid-liquid separation step; and, in contrast, when a step and facilities for the AD removing treatment of the aqueous phase are employed, the liquid temperature in the liquid-liquid separation is preferably set low in the liquid-liquid separation step, where these are preferred regardless of the presence or absence of methyl acetate.

The results in Examples 7 to 11 demonstrate that the AD partition coefficient tends to decrease and the distribution ratio of AD to the organic phase tends to be relatively higher with an increasing MA concentration in the light ends column charge liquid and with an increasing MA concentration in at least one of the aqueous phase and the organic phase. Specifically, from the viewpoint of acetaldehyde removal efficiency, the AD removing treatment of the organic phase has large advantages at a high MA concentration in at least one of the aqueous phase and the organic phase; but has small advantages at a low MA concentration in at least one of the aqueous phase and the organic phase. In contrast, the AD removing treatment of the aqueous phase has large advantages at a low MA concentration in at least one of the aqueous phase and the organic phase; but has small advantages at a high MA concentration in at least one of the aqueous phase and the organic phase. From another aspect, when a step and facilities for the AD removing treatment of the organic phase are employed, the MA concentration in at least one of the aqueous phase and the organic phase in the liquid-liquid separation step is preferably increased typically by regulating one or more of conditions such as reaction conditions in the reactor, evaporation conditions in the evaporator, and distillation conditions for the vapor stream from the evaporation step. In contrast, when a step and facilities for the AD removing treatment of the aqueous phase are employed, the MA concentration in at least one of the aqueous phase and the organic phase in the liquid-liquid separation step is preferably lowered typically by regulating one or more of conditions such as reaction conditions in the reactor, evaporation conditions in the evaporator, and distillation conditions for the vapor stream from the evaporation step. The results in Examples 7 to 11 demonstrate that not only the AD partition coefficient, but also the MA partition coefficient decrease with an increasing MA concentration in the charge liquid and with an increasing MA concentration in at least one of the aqueous phase and the organic phase.

In Examples 5, and 7 to 11, operations were performed under common conditions for the hydrogen partial pressure in the reactor, the reflux ratio at the light ends column, the reflux ratio at the dehydration column, the reflux ratio at the crotonaldehyde-removing column, the liquid temperature in the liquid-liquid separation, and the AD removing treatment operation conditions. However, these examples differ in product permanganate time of the second acetic acid stream by about 4 times. Namely, the minimum permanganate time is 150 minutes (Example 7), and the maximum permanganate time is 540 minutes or longer (Example 11). Focusing on AD partition coefficients, the AD partition coefficient is 4.3 in Example 7 which gives the minimum product permanganate time; but the AD partition coefficient is 1.1 in Example 11 which gives the maximum permanganate time. Difference in operation conditions between these examples is difference in MA concentration in the light ends column charge. Owing to this, the MA concentrations in the decanter (in the aqueous phase and the organic phase) are changed to cause the AD partition coefficient also to be changed. The AD removing treatment of the aqueous phase is more advantageous when the AD partition coefficient is at some high level (when acetaldehyde is distributed to the aqueous phase in a relatively large amount); whereas the AD removing treatment of the organic phase is more advantageous when the AD partition coefficient is at some low level (when acetaldehyde is distributed to the organic phase in a relatively large amount). In consideration of these, the results demonstrate that by-produced acetaldehyde can be industrially advantageously removed still more efficiently, because the object to be subjected to the AD removing treatment can be rationally selected from at least a part of at least one of the aqueous phase and the organic phase, by utilizing the AD partition coefficient in the liquid-liquid separation step as one of indices for performing the AD removing step; and that this also contributes to a better product permanganate time.

Comparisons between Example 1 and Example 13 demonstrate that the acetic acid product has a better product permanganate time (90 minutes) as better (longer) as about 1.3 times, when the decanter is operated at a higher temperature and thereby the AD concentration in the organic phase in the decanter is increased, because acetaldehyde is removed in a larger amount, and crotonaldehyde is formed in a smaller amount. This indicates that the temperature condition (liquid temperature in the liquid-liquid separation) in the decanter serves as one of effective parameters for performing the AD removing treatment with high efficiency.

Comparisons between Examples 11 and 14 demonstrate that an organic phase and an aqueous phase having AD concentrations at approximately the same levels, when each subjected to an AD removing treatment, give acetic acid products that are approximately at the same levels with one another in crotonaldehyde concentration, 2-ethylcrotonaldehyde concentration, and permanganate time. Specifically, the comparisons demonstrate that either of the aqueous phase and the organic phase will do as the object to be subjected to the AD removing treatment, at AD concentrations in such an intermediate region. Conditions for Examples 11 and 14 are identical in hydrogen partial pressure in the reactor, reflux ratio at the light ends column, and reflux ratio at the dehydration column, but are different only in reflux ratio at the crotonaldehyde-removing column. Specifically, the reflux ratio in Example 14 is 50, which is 5 times as much as the reflux ratio in Example 11. However, these examples differ little in product permanganate time. This is probably because the acetic acid products have very increased purities, and the index product permanganate time is not so affected by the difference in reflux ratio at the crotonaldehyde-removing column, i.e., the difference between a reflux ratio of 10 (Example 11) and a reflux ratio of 50 (Example 14). The comparisons also demonstrate that an unlimitedly increased reflux ratio at the crotonaldehyde-removing column does not provide further advantageous effects, because the crotonaldehyde separation efficiency approaches a constant value with an increasing reflux ratio at the crotonaldehyde-removing column.

These results and considerations demonstrate that the product quality can be improved by synergistic effects more than expected, where the synergistic effects result from: operating the light ends column at a higher reflux ratio to cause crotonaldehyde to be concentrated at the column top; recycling such concentrated crotonaldehyde to the reactor to cause crotonaldehyde to be converted, in the reactor, into 2-ethylcrotonaldehyde and/or butyl acetate (crotonaldehyde+acetaldehyde→2-ethylcrotonaldehyde, crotonaldehyde+hydrogen→butyl alcohol, butyl alcohol+acetic acid→butyl acetate); and operating the light ends column at a higher reflux ratio to cause crotonaldehyde to be concentrated at the column top and, in addition, subjecting the overhead liquid (for example, the organic phase) to a distillation treatment to efficiently remove crotonaldehyde.

Specifically, the results and considerations demonstrate that by-produced acetaldehyde can be industrially advantageously removed, and this enables industrially still more efficient production of high-quality acetic acid yielding a good potassium permanganate test result, by employing all configurations of: (1) control of the crotonaldehyde concentration in the first acetic acid stream, which is from the light ends column, at a specific level or lower and/or operation of the dehydration column with a reflux ratio at a specific level or higher; (2) operation of the light ends column with a reflux ratio at a specific level or higher to efficiently remove crotonaldehyde by the crotonaldehyde-removing step; and (3) rational selection of the object to be subjected to the acetaldehyde-removing treatment on the basis of a factor or factors such as the acetaldehyde partition coefficient in the liquid-liquid separation step.

As a summary of the above description, configurations of the present invention, as well as variations thereof, will be listed below as appendices.

(1) A method for producing acetic acid, the method including the steps of:

carbonylating methanol with carbon monoxide in a reactor in the presence of a catalytic system, acetic acid, methyl acetate, and water, to form acetic acid in a reaction mixture, where the catalytic system includes a metal catalyst and methyl iodide;

separating the reaction mixture, using at least one selected from evaporators and distillation columns, into a stream including the metal catalyst, an acetic acid stream rich in acetic acid, and a stream richer in light ends than the acetic acid stream;

liquid-liquid separating a process stream including water, acetic acid, methyl iodide, and acetaldehyde into an aqueous phase and an organic phase;

removing acetaldehyde derived from the process stream by a treatment of an object, where the object is selected from at least a part of at least one of the aqueous phase and the organic phase on the basis of a factor or factors selected from the group consisting of a liquid temperature in the liquid-liquid separation in the liquid-liquid separation step, an acetaldehyde concentration in at least one of the aqueous phase and the organic phase, an acetaldehyde partition coefficient, a methyl acetate concentration in at least one of the aqueous phase and the organic phase, and a methyl acetate partition coefficient;

recycling at least a part of at least one of the aqueous phase and the organic phase to the reactor; and removing crotonaldehyde from at least another part of at least one of the aqueous phase and the organic phase by a distillation treatment in a distillation column, wherein the separation step includes the substep of yielding, by separation using a first distillation column, a first acetic acid stream rich in acetic acid, and an overhead stream richer in light ends than the first acetic acid stream, wherein, in the substep, a crotonaldehyde concentration in the first acetic acid stream is controlled to 2.2 ppm by mass or less, wherein a reflux ratio at the first distillation column in the separation step is controlled so that: the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column, and wherein the distillation column in the crotonaldehyde-removing step so as to meet at least one of conditions (a-i) to (a-iii) as follows:

(a-i) a reflux ratio at the distillation column is 0.01 or more;

(a-ii) at the distillation column, the ratio of a crotonaldehyde concentration (ppm by mass) in a distillate to a crotonaldehyde concentration (ppm by mass) in a charge liquid is less than 1; and (a-iii) at the distillation column, the ratio of a crotonaldehyde concentration (ppm by mass) in bottoms to a crotonaldehyde concentration (ppm by mass) in the charge liquid is greater than 1.

(2) A method for producing acetic acid, the method including the steps of:

carbonylating methanol with carbon monoxide in a reactor in the presence of a catalytic system, acetic acid, methyl acetate, and water, to form acetic acid in a reaction mixture, where the catalytic system includes a metal catalyst and methyl iodide;

separating the reaction mixture, using at least one selected from evaporators and distillation columns, into a stream including the metal catalyst, an acetic acid stream rich in acetic acid, and a stream richer in light ends than the acetic acid stream;

liquid-liquid separating a process stream including water, acetic acid, methyl iodide, and acetaldehyde into an aqueous phase and an organic phase;

removing acetaldehyde derived from the process stream by a treatment of an object, where the object is selected from at least a part of at least one of the aqueous phase and the organic phase on the basis of a factor or factors selected from the group consisting of a liquid temperature in the liquid-liquid separation in the liquid-liquid separation step, an acetaldehyde concentration in at least one of the aqueous phase and the organic phase, an acetaldehyde partition coefficient, a methyl acetate concentration in at least one of the aqueous phase and the organic phase, and a methyl acetate partition coefficient;

recycling at least a part of at least one of the aqueous phase and the organic phase to the reactor; and removing crotonaldehyde from at least another part of at least one of the aqueous phase and the organic phase, by a distillation treatment in a distillation column, wherein the separation step includes the substep of yielding, by separation using a first distillation column, a first acetic acid stream rich in acetic acid, and an overhead stream richer in light ends than the first acetic acid stream, wherein, in the substep, a crotonaldehyde concentration in the first acetic acid stream is controlled to 2.2 ppm by mass or less, and a ratio ($C_{CR}/C_{ECR}$) of a crotonaldehyde concentration $C_{CR}$ (ppm by mass) to an 2-ethylcrotonaldehyde concentration $C_{ECR}$ (ppm by mass) in the first acetic acid stream is regulated, wherein a reflux ratio at the first distillation column in the separation step is controlled so that: the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column, and wherein the distillation column in the crotonaldehyde-removing step so as to meet at least one of conditions (a-i) to (a-iii) as follows:

(a-i) a reflux ratio at the distillation column is 0.01 or more;

(a-ii) at the distillation column, the ratio of a crotonaldehyde concentration (ppm by mass) in a distillate to a crotonaldehyde concentration (ppm by mass) in a charge liquid is less than 1; and (a-iii) at the distillation column, the ratio of a crotonaldehyde concentration (ppm by mass) in bottoms to a crotonaldehyde concentration (ppm by mass) in the charge liquid is greater than 1.

(3) A method for producing acetic acid, the method including the steps of:

carbonylating methanol with carbon monoxide in a reactor in the presence of a catalytic system, acetic acid, methyl acetate, and water, to form acetic acid in a reaction mixture, where the catalytic system includes a metal catalyst and methyl iodide;

separating the reaction mixture, using at least one selected from evaporators and distillation columns, into a stream including the metal catalyst, an acetic acid stream rich in acetic acid, and a stream richer in light ends than the acetic acid stream;

liquid-liquid separating a process stream including water, acetic acid, methyl iodide, and acetaldehyde into an aqueous phase and an organic phase;

removing acetaldehyde derived from the process stream by a treatment of an object, where the object is selected from at least a part of at least one of the aqueous phase and the organic phase on the basis of a factor or factors selected from the group consisting of a liquid temperature in the liquid-liquid separation in the liquid-liquid separation step, an acetaldehyde concentration in at least one of the aqueous phase and the organic phase, an acetaldehyde partition coefficient, a methyl acetate concentration in at least one of the aqueous phase and the organic phase, and a methyl acetate partition coefficient;

recycling at least a part of at least one of the aqueous phase and the organic phase to the reactor;

removing crotonaldehyde from at least another part of at least one of the aqueous phase and the organic phase by a distillation treatment in a distillation column, wherein the separation step includes the substeps of yielding, by separation using a first distillation column, a first acetic acid stream rich in acetic acid, and a first overhead stream richer in light ends than the first acetic acid stream; and separating the first acetic acid stream, using a second distillation column, into a second overhead stream rich in water, and a second acetic acid stream richer in acetic acid than the first acetic acid stream, wherein, in the substeps, a crotonaldehyde concentration in the first acetic acid stream is controlled to 2.2 ppm by mass or less, and/or a reflux ratio at the second distillation column is controlled to 0.1 or more, and a reflux ratio at the first distillation column in the separation step is controlled so that: the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column, and wherein the distillation column in the crotonaldehyde-removing step so as to meet at least one of conditions (a-i) to (a-iii) as follows:

(a-i) a reflux ratio at the distillation column is 0.01 or more;

(a-ii) at the distillation column, the ratio of a crotonaldehyde concentration (ppm by mass) in a distillate to a crotonaldehyde concentration (ppm by mass) in a charge liquid is less than 1; and (a-iii) at the distillation column, the ratio of a crotonaldehyde concentration (ppm by mass) in bottoms to a crotonaldehyde concentration (ppm by mass) in the charge liquid is greater than 1.

(4) A method for producing acetic acid, the method including the steps of:

carbonylating methanol with carbon monoxide in a reactor in the presence of a catalytic system, acetic acid, methyl acetate, and water, to form acetic acid in a reaction mixture, where the catalytic system includes a metal catalyst and methyl iodide;

separating the reaction mixture, using at least one selected from evaporators and distillation columns, into a stream including the metal catalyst, an acetic acid stream rich in acetic acid, and a stream richer in light ends than the acetic acid stream;

liquid-liquid separating a process stream including water, acetic acid, methyl iodide, and acetaldehyde into an aqueous phase and an organic phase;

removing acetaldehyde derived from the process stream by a treatment of an object, where the object is selected from at least a part of at least one of the aqueous phase and the organic phase on the basis of a factor or factors selected from the group consisting of a liquid temperature in the liquid-liquid separation in the liquid-liquid separation step, an acetaldehyde concentration in at least one of the aqueous phase and the organic phase, an acetaldehyde partition coefficient, a methyl acetate concentration in at least one of the aqueous phase and the organic phase, and a methyl acetate partition coefficient;

recycling at least a part of at least one of the aqueous phase and the organic phase to the reactor; and removing crotonaldehyde from at least another part of at least one of the aqueous phase and the organic phase by a distillation treatment in a distillation column, wherein the separation step includes the substeps of yielding, by separation using a first distillation column, a first acetic acid stream rich in acetic acid, and a first overhead stream richer in light ends than the first acetic acid stream; and separating the first acetic acid stream, using a second distillation column, into a second overhead stream rich in water, and a second acetic acid stream richer in acetic acid than the first acetic acid stream, wherein, in the substeps, a crotonaldehyde concentration in the first acetic acid stream is controlled to 2.2 ppm by mass or less, and/or a reflux ratio in the second distillation column is controlled to 0.1 or more, and a ratio ($C_{CR}/C_{ECR}$) of a crotonaldehyde concentration $C_{CR}$ (ppm by mass) to an 2-ethylcrotonaldehyde concentration $C_{ECR}$ (ppm by mass) in at least one of the first acetic acid stream and the second acetic acid stream is regulated, wherein a reflux ratio at the first distillation column in the separation step is controlled so that: the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column, and wherein the distillation column in the crotonaldehyde-removing step so as to meet at least one of conditions (a-i) to (a-iii) as follows:

(a-i) a reflux ratio at the distillation column is 0.01 or more;

(a-ii) at the distillation column, the ratio of a crotonaldehyde concentration (ppm by mass) in a distillate to a crotonaldehyde concentration (ppm by mass) in a charge liquid is less than 1; and (a-iii) at the distillation column, the ratio of a crotonaldehyde concentration (ppm by mass) in bottoms to a crotonaldehyde concentration (ppm by mass) in the charge liquid is greater than 1.

(5) The acetic acid production method according to any one of (1) to (4), wherein the liquid-liquid separation step meets at least one of conditions (b-i) to (b-v), and at least a part of the aqueous phase is subjected to the treatment in the acetaldehyde-removing step, where the conditions (b-i) to (b-v) are expressed as follows:

(b-i) the aqueous phase has an acetaldehyde concentration of 28.1 mass percent or less, and/or the organic phase has an acetaldehyde concentration of 24.8 mass percent or less;

(b-ii) the liquid-liquid separation is performed at a temperature of 70° C. or lower;

(b-iii) the aqueous phase has a methyl acetate concentration of 12.0 mass percent or less, and/or the organic phase has a methyl acetate concentration of 47.6 mass percent or less, and/or the totality of the methyl acetate concentration in the aqueous phase and the methyl acetate concentration in the organic phase is 59.6 mass percent or less;

(b-iv) an acetaldehyde partition coefficient is 1.1 or more, where the acetaldehyde partition coefficient is the ratio of the acetaldehyde concentration (mass percent) in the aqueous phase to the acetaldehyde concentration (mass percent) in the organic phase; and (b-v) a methyl acetate partition coefficient is 0.25 or more, where the methyl acetate partition coefficient is the ratio of the methyl acetate concentration (mass percent) in the aqueous phase to the methyl acetate concentration (mass percent) in the organic phase.

(6) The acetic acid production method according to (5), wherein, relating to the condition (b-i), the aqueous phase has an acetaldehyde concentration of 28.1 mass percent or less, and the organic phase has an acetaldehyde concentration of 24.8 mass percent or less.

(7) The acetic acid production method according to one of (5) and (6), wherein, relating to the condition (b-i), the aqueous phase has an acetaldehyde concentration of 0.045 to 28.1 mass percent (preferably 0.098 to 10 mass percent, furthermore preferably 0.098 to 3.0 mass percent, and particularly preferably 0.098 to 1.0 mass percent (for example, 0.15 to 0.9 mass percent)).

(8) The acetic acid production method according to any one of (5) to (7), wherein, relating to the condition (b-i), the organic phase has an acetaldehyde concentration of 0.013 to 24.8 mass percent (preferably 0.030 to 2.0 mass percent, furthermore preferably 0.030 to 0.50 mass percent, and particularly preferably 0.030 to 0.24 mass percent).

(9) The acetic acid production method according to any one of (5) to (8), wherein the condition (b-i) is met, and the liquid to be subjected to the liquid-liquid separation has an acetaldehyde concentration of 26.0 mass percent or less (typically 0.026 to 26.0 mass percent, preferably 0.057 to 10 mass percent, furthermore preferably 0.057 to 3.0 mass percent, and particularly preferably 0.057 to 1.0 mass percent (for example, 0.057 to 0.42 mass percent)).

(10) The acetic acid production method according to any one of (5) to (9), wherein, relating to the condition (b-ii), the liquid-liquid separation is performed at a temperature of −5° C. to 70° C. (preferably −5° C. to 60° C., more preferably −5° C. to 51° C. (for example, −5° C. to 45° C.), and furthermore preferably −5° C. to 41° C. (for example, −5° C. to 31° C.)

(11) The acetic acid production method according to any one of (5) to (10), wherein, relating to the condition (b-iii), the aqueous phase has a methyl acetate concentration of 12.0 mass percent or less, and the organic phase has a methyl acetate concentration of 47.6 mass percent or less.

(12) The acetic acid production method according to any one of (5) to (11), wherein, relating to the condition (b-iii), the aqueous phase has a methyl acetate concentration of 1.2 to 12.0 mass percent (preferably 2.0 to 12.0 mass percent, and furthermore preferably 5.0 to 12.0 mass percent (for example, 6.0 to 12.0 mass percent)).

(13) The acetic acid production method according to any one of (5) to (12), wherein, relating to the condition (b-iii), the organic phase has a methyl acetate concentration of 2.2 to 47.6 mass percent (preferably 5.0 to 42 mass percent, and furthermore preferably 8.0 to 35 mass percent (for example, 10.0 to 30 mass percent)).

(14) The acetic acid production method according to any one of (5) to (13), wherein, relating to the condition (b-iii), the totality of the methyl acetate concentration in the aqueous phase and the methyl acetate concentration in the organic phase is 4.2 to 59.6 mass percent (preferably 6.0 to 54 mass percent, more preferably 8.0 to 54 mass percent, furthermore preferably 10.0 to 54 mass percent, and particularly preferably 14.0 to 47 mass percent (for example, 16.0 to 42 mass percent)).

(15) The acetic acid production method according to any one of (5) to (14), wherein the condition (b-iii) is met, and the liquid to be subjected to the liquid-liquid separation has a methyl acetate concentration of 38.2 mass percent or less (typically 2.0 to 38.2 mass percent, preferably 5.0 to 31 mass percent, more preferably 8.0 to 25 mass percent, and furthermore preferably 10.0 to 25 mass percent).

(16) The acetic acid production method according to any one of (5) to (15), wherein, relating to the condition (b-iv), the acetaldehyde partition coefficient is 1.1 to 8.0 (preferably 1.5 to 6.0, and furthermore preferably 1.9 to 5.0).

(17) The acetic acid production method according to any one of (5) to (16), wherein, relating to the condition (b-v), the methyl acetate partition coefficient is 0.26 or more (typically 0.26 to 0.65, and preferably 0.28 or more (for example, 0.28 to 0.60)).

(18) The acetic acid production method according to any one of (5) to (17), wherein the liquid-liquid separation step meets at least the conditions (b-i), (b-ii), and (b-iii) together.

(19) The acetic acid production method according to any one of (5) to (18), wherein the liquid-liquid separation step meets at least the conditions (b-i), (b-ii), (b-iii), and (b-iv) together.

(20) The acetic acid production method according to any one of (5) to (19), wherein the liquid-liquid separation step meets all the conditions (b-i), (b-ii), (b-iii), (b-iv), and (b-v).

(21) The acetic acid production method according to any one of (1) to (4), wherein the liquid-liquid separation step meets at least one of conditions (b'-i) to (b'-v), and at least a part of the organic phase is subjected to the treatment in the acetaldehyde-removing step, where the conditions (b'-i) to (b'-v) are expressed as follows:

(b'-i) the aqueous phase has an acetaldehyde concentration of 0.045 mass percent or more, and/or the organic phase has an acetaldehyde concentration of 0.013 mass percent or more;

(b'-ii) the liquid-liquid separation is performed at a temperature of −5° C. or higher;

(b'-iii) the aqueous phase has a methyl acetate concentration of 1.2 mass percent or more, and/or the organic phase has a methyl acetate concentration of 2.2 mass percent or more, and/or the totality of the methyl acetate concentration in the aqueous phase and the methyl acetate concentration in the organic phase is 3.4 mass percent or more;

(b'-iv) an acetaldehyde partition coefficient is 4.1 or less, where the acetaldehyde partition coefficient is the ratio of the acetaldehyde concentration (mass percent) in the aqueous phase to the acetaldehyde concentration (mass percent) in the organic phase; and (b'-v) a methyl acetate partition coefficient is 0.8 or less, where the methyl acetate partition coefficient is the ratio of the methyl acetate concentration (mass percent) in the aqueous phase to the methyl acetate concentration (mass percent) in the organic phase.

(22) The acetic acid production method according to (21), wherein, relating to the condition (b'-i), the aqueous phase has an acetaldehyde concentration of 0.045 mass percent or more, and the organic phase has an acetaldehyde concentration of 0.013 mass percent or more.

(23) The acetic acid production method according to one of (21) and (22), wherein, relating to the condition (b'-i), the aqueous phase has an acetaldehyde concentration of 0.045 to 35 mass percent (preferably 0.15 to 10 mass percent, and furthermore preferably 0.2 to 2.0 mass percent).

(24) The acetic acid production method according to any one of (21) to (23), wherein, relating to the condition (b'-i), the organic phase has an acetaldehyde concentration of 0.013 to 30 mass percent (preferably 0.05 to 5.0 mass percent, and furthermore preferably 0.1 to 1.0 mass percent).

(25) The acetic acid production method according to any one of (21) to (24), wherein the condition (b'-i) is met, and the liquid to be subjected to the liquid-liquid separation has an acetaldehyde concentration of 0.026 mass percent or more (typically 0.026 to 32 mass percent, preferably 0.10 to 8.0 mass percent, and furthermore preferably 0.15 to 1.8 mass percent).

(26) The acetic acid production method according to any one of (21) to (25), wherein, relating to the condition (b'-ii), the liquid-liquid separation is performed at a temperature of 0° C. or higher (typically 0° C. to 90° C., preferably 10° C. or higher (for example, 10° C. to 90° C.), more preferably 10° C. or higher (for example, 10° C. to 90° C.), furthermore preferably 20° C. or higher (for example, 25° C. to 90° C.), a temperature higher than 30° C. (for example, from higher than 30° C. to 90° C.)), a temperature higher than 35° C. (for example, from higher than 35° C. to 90° C.), a temperature higher than 40° C. (for example, from higher than 40° C. to 90° C.), and particularly preferably a temperature higher than 70° C. (for example, from higher than 70° C. to 90° C.)

(27) The acetic acid production method according to any one of (21) to (26), wherein, relating to the condition (b'-iii), the aqueous phase has a methyl acetate concentration of 1.2 mass percent or more, and the organic phase has a methyl acetate concentration of 2.2 mass percent or more.

(28) The acetic acid production method according to any one of (21) to (27), wherein, relating to the condition (b'-iii), the aqueous phase has a methyl acetate concentration of 1.2 to 20 mass percent (preferably 2.5 to 18 mass percent, more preferably 4.0 to 15 mass percent, furthermore preferably 6.0 to 13 mass percent, and particularly preferably 7.0 to 12 mass percent).

(29) The acetic acid production method according to any one of (21) to (28), wherein, relating to the condition (b'-iii), the organic phase has a methyl acetate concentration of 2.2 to 60 mass percent (preferably 5.8 to 48 mass percent, more preferably 8.0 to 40 mass percent, furthermore preferably 10.0 to 30 mass percent, and particularly preferably 11.0 to 25 mass percent).

(30) The acetic acid production method according to any one of (21) to (29), wherein, relating to the condition (b'-iii), the totality of the methyl acetate concentration in the aqueous phase and the methyl acetate concentration in the organic phase is 3.4 to 75 mass percent (preferably 8.3 to 60 mass percent (for example, 10.0 to 40 mass percent), more preferably 15.0 to 50 mass percent, and furthermore preferably 25.0 to 53 mass percent).

(31) The acetic acid production method according to any one of (21) to (30), wherein the condition (b'-iii) is met, and the liquid to be subjected to the liquid-liquid separation has a methyl acetate concentration of 2.0 to 50 mass percent (preferably 5.0 to 38 mass percent, more preferably 8.0 to 35 mass percent, furthermore preferably 10.0 to 32 mass percent, and particularly preferably 15 to 31 mass percent).

(32) The acetic acid production method according to any one of (21) to (31), wherein, relating to the condition (b'-iv), the acetaldehyde partition coefficient is 3.35 or less ((typically 0.6 to 3.35), more preferably 3 or less (0.7 to 3), furthermore preferably 2.8 or less (for example, 0.8 to 2.8), particularly preferably 2.5 or less (for example, 0.8 to 2.5), especially preferably 2.3 or less (for example, 0.9 to 2.3), and still especially preferably 2.0 or less (for example, 1.0 to 2.0)).

(33) The acetic acid production method according to any one of (21) to (32), wherein, relating to the condition (b'-v), the methyl acetate partition coefficient is 0.7 or less ((typically 0.20 to 0.70), more preferably 0.6 or less (for example, 0.20 to 0.60), furthermore preferably 0.44 or less (for example, 0.20 to 0.44), and particularly preferably less than 0.25 (for example, from 0.20 to less than 0.25)).

(34) The acetic acid production method according to any one of (21) to (33), wherein the liquid-liquid separation step meets at least the conditions (b'-i), (b'-ii), and (b'-iii) together.

(35) The acetic acid production method according to any one of (21) to (34), wherein the liquid-liquid separation step meets at least the conditions (b'-i), (b'-ii), (b'-iii), and (b'-iv) together.

(36) The acetic acid production method according to any one of (21) to (35), wherein the liquid-liquid separation step meets all the conditions (b'-i), (b'-ii), (b'-iii), (b'-iv), and (b'-v).

(37) The acetic acid production method according to any one of (1) to (36), wherein the separation step includes the steps of:

evaporating the reaction mixture in an evaporator to separate the reaction mixture into a vapor stream and a residue stream; and removing light ends, by separating the vapor stream, using the first distillation column, into a first overhead stream rich in at least one light end selected from methyl iodide and acetaldehyde, and the first acetic acid stream rich in acetic acid, and subjecting the first overhead stream to condensation and liquid-liquid separation to give an aqueous phase and an organic phase.

(38) The acetic acid production method according to (37), wherein the separation step includes the step of dehydrating the first acetic acid stream by separation, using a second distillation column, into a second overhead stream rich in water, and a second acetic acid stream richer in acetic acid than the first acetic acid stream.

(39) The acetic acid production method according to any one of (3) to (38), wherein the second distillation column is operated at a reflux ratio controlled to 0.3 or more (typically 0.32 or more, preferably 0.35 or more, more preferably 0.4 or more, furthermore preferably 1 or more, and particularly preferably 2 or more).

(40) The acetic acid production method according to any one of (3) to (39), wherein the second distillation column is operated at a reflux ratio of 3000 or less (preferably about 1000 or less, more preferably about 100 or less, and furthermore preferably about 10 or less).

(41) The acetic acid production method according to any one of (38) to (40), wherein the second acetic acid stream has a crotonaldehyde concentration of 2.0 ppm by mass or less (preferably 1.8 ppm by mass or less, more preferably 1.5 ppm by mass or less, furthermore preferably 1.2 ppm by mass or less, particularly preferably 0.7 ppm by mass or less, and especially preferably 0.5 ppm by mass or less).

(42) The acetic acid production method according to any one of (38) to (41), wherein the second acetic acid stream has an 2-ethylcrotonaldehyde concentration of 3.0 ppm by mass or less (preferably 1.8 ppm by mass or less, more preferably 1.5 ppm by mass or less, furthermore preferably 1.2 ppm by mass or less, particularly preferably 0.7 ppm by mass or less, and especially preferably 0.5 ppm by mass or less).

(43) The acetic acid production method according to any one of (38) to (42), wherein the second acetic acid stream has a ratio ($C_{CR}/C_{ECR}$) of the crotonaldehyde concentration $C_{CR}$ (ppm by mass) to the 2-ethylcrotonaldehyde concentration $C_{ECR}$ (ppm by mass) of 50 or less (preferably 35 or less, more preferably 25 or less, furthermore preferably 20 or less, and particularly preferably 15 or less).

(44) The acetic acid production method according to any one of (38) to (43), wherein the second acetic acid stream has a butyl acetate concentration of 15 ppm by mass or less (preferably 12 ppm by mass or less, more preferably 10 ppm by mass or less, and furthermore preferably 8 ppm by mass or less).

(45) The acetic acid production method according to any one of (38) to (44), wherein the second acetic acid stream has a ratio ($C_{CR}/C_{BA}$) of the crotonaldehyde concentration $C_{CR}$ (ppm by mass) to the butyl acetate concentration $C_{BA}$ (ppm by mass) of 2.0 or less (preferably 1.5 or less, more preferably 1.0 or less, and furthermore preferably 0.6 or less).

(46) The acetic acid production method according to any one of (1) to (45), wherein the catalytic system further includes an ionic iodide.

(47) The acetic acid production method according to any one of (1) to (46), wherein at least a part of a residue is recycled to the reactor, where the residue is a residue remained after the acetaldehyde removal from at least a part of at least one of the aqueous phase and the organic phase.

(48) The acetic acid production method according to any one of (1) to (47), wherein the reactor is operated at a hydrogen partial pressure of typically 0.001 MPa (absolute pressure) or more (preferably 0.005 MPa or more, more preferably 0.01 MPa (absolute pressure) or more (for example, 0.015 MPa or more), furthermore preferably 0.02 MPa (absolute pressure) or more, particularly preferably 0.04 MPa (absolute pressure) or more, and especially preferably 0.06 MPa (absolute pressure) or more (for example, 0.07 MPa (absolute pressure) or more)).

(49) The acetic acid production method according to any one of (1) to (48), wherein a liquid reaction mixture in the reactor has an acetaldehyde concentration of 500 ppm by mass or less (preferably 450 ppm by mass or less, more preferably 400 ppm by mass or less, furthermore preferably 350 ppm by mass or less, particularly preferably 300 ppm by mass or less, and especially preferably 250 ppm by mass or less).

(50) The acetic acid production method according to any one of (38) to (49), wherein the second acetic acid stream has a crotonaldehyde concentration of 0.98 ppm by mass or less (preferably 0.80 ppm by mass or less, more preferably 0.50 ppm by mass or less, and furthermore preferably 0.30 ppm by mass or less), and/or an 2-ethylcrotonaldehyde concentration of 1.0 ppm by mass or less (preferably 0.50 ppm by mass or less, more preferably 0.30 ppm by mass or less, and furthermore preferably 0.20 ppm by mass or less), and/or a butyl acetate concentration of 15 ppm by mass or less (preferably 10 ppm by mass or less, more preferably 8 ppm by mass or less, furthermore preferably 5 ppm by mass or less, and particularly preferably 3 ppm by mass or less).

(51) The acetic acid production method according to any one of (38) to (50), wherein the second acetic acid stream yields a potassium permanganate test result of longer than 50 minutes (preferably 60 minutes or longer, more preferably 100 minutes or longer, furthermore preferably 120 minutes or longer, particularly preferably 180 minutes or longer, especially preferably 240 minutes or longer, and still especially preferably 360 minutes or longer).

(52) The acetic acid production method according to any one of any one of (37) to (51), wherein the vapor stream to be fed to the first distillation column has a crotonaldehyde concentration of 0 to 5.0 ppm by mass (preferably 0.01 to 4.0 ppm by mass, more preferably 0.1 to 3.0 ppm by mass, and furthermore preferably 0.2 to 2.0 ppm by mass), and/or an 2-ethylcrotonaldehyde concentration of 0 to 3.0 ppm by mass (preferably 0.01 to 2.5 ppm by mass, more preferably 0.02 to 2.0 ppm by mass, and furthermore preferably 0.03 to 0.8 ppm by mass), and/or a butyl acetate concentration of 0.1 to 13.0 ppm by mass (preferably 0.2 to 12.0 ppm by mass, and more preferably 0.3 to 9.0 ppm by mass).

(53) The acetic acid production method according to any one of (1) to (52), wherein the first acetic acid stream has a crotonaldehyde concentration of 1.3 ppm by mass or less (preferably 1.0 ppm by mass or less, more preferably 0.85 ppm by mass or less, furthermore preferably 0.5 ppm by mass or less, and particularly preferably 0.25 ppm by mass or less), and/or an 2-ethylcrotonaldehyde concentration of 1.0 ppm by mass or less (preferably 0.50 ppm by mass or less), and/or a butyl acetate concentration of 15 ppm by mass or less (preferably 10 ppm by mass or less, more preferably 8 ppm by mass or less, furthermore preferably 5 ppm by mass or less, and particularly preferably 3 ppm by mass or less).

(54) The acetic acid production method according to any one of (1) to (53), wherein the charge liquid to the distillation column in the crotonaldehyde-removing step has a crotonaldehyde concentration of 0.01 to 50 ppm by mass (preferably 0.1 to 50 ppm by mass, more preferably 0.3 to 30 ppm by mass, furthermore preferably 0.5 to 10 ppm by mass, particularly preferably 0.8 to 7.0 ppm by mass, and especially preferably 1.0 to 5.0 ppm by mass).

(55) The acetic acid production method according to any one of (1) to (54), wherein the distillation column in the crotonaldehyde-removing step is operated so as to meet all the conditions (a-i) to (a-iii).

(56) The acetic acid production method according to any one of (1) to (55), wherein the distillation in the crotonaldehyde-removing step is performed batchwise.

(57) The acetic acid production method according to any one of (1) to (56), wherein the distillation column in the crotonaldehyde-removing step is operated at a throughput of 0.0001 to 50 parts by mass (preferably 0.001 to 30 parts by mass, more preferably 0.01 to 10 parts by mass, and furthermore preferably 0.1 to 5 parts by mass), per 100 parts by mass of the vapor stream fed to the first distillation column.

(58) The acetic acid production method according to any one of (1) to (57), wherein an overhead condensate from the distillation column in the crotonaldehyde-removing step is recycled to at least one of the aqueous phase, the organic phase, and the reactor.

(59) The acetic acid production method according to any one of (1) to (58), wherein the aqueous phase alone is refluxed to the first distillation column, and the reflux ratio for the aqueous phase at the first distillation column is controlled to 3 or more (preferably 5 or more, more preferably 8 or more, and furthermore preferably 12 or more).

(60) The acetic acid production method according to any one of (1) to (59), wherein the organic phase alone is refluxed to the first distillation column, and the reflux ratio for the organic phase at the first distillation column is controlled to 1.5 or more (preferably 2 or more, more preferably 4 or more, and furthermore preferably 5 or more).

(61) The acetic acid production method according to any one of (1) to (60), wherein both the aqueous phase and the organic phase are refluxed to the first distillation column, and the total reflux ratio for the aqueous phase and the organic phase at the first distillation column is controlled to 2.3 or more (preferably 3.5 or more, more preferably 6 or more, and furthermore preferably 8.5 or more).

(62) The acetic acid production method according to any one of (1) to (61), wherein the first distillation column is operated at a reflux ratio of 3000 or less (preferably 1000 or less, more preferably 100 or less, and furthermore preferably 30 or less).

(63) The acetic acid production method according to any one of (1) to (62), wherein, relating to the condition (a-i), the distillation column is operated at a reflux ratio of 0.05 or more (preferably 0.5 or more, more preferably 5 or more, furthermore preferably 20 or more, and particularly preferably 30 or more).

(64) The acetic acid production method according to any one of (1) to (63), wherein, relating to the condition (a-i), the distillation column is operated at a reflux ratio of 1000 or less.

(65) The acetic acid production method according to any one of (1) to (64), wherein, relating to the condition (a-ii), at the distillation column, the ratio of the crotonaldehyde concentration (ppm by mass) in the distillate to the crotonaldehyde concentration (ppm by mass) in the charge liquid is 0.95 or less (preferably 0.80 or less, more preferably 0.70 or less, furthermore preferably 0.60 or less, particularly preferably 0.50 or less, especially preferably 0.30 or less, and still especially preferably 0.20 or less).

(66) The acetic acid production method according to any one of (1) to (65), wherein, relating to the condition (a-iii), at the distillation column, the ratio of the crotonaldehyde concentration (ppm by mass) in bottoms to the crotonaldehyde concentration (ppm by mass) in the charge liquid is 1.2 or more (preferably 1.5 or more, more preferably 2.0 or more, furthermore preferably 3.0 or more, particularly preferably 4.0 or more, especially preferably 5.0 or more, still especially preferably 10 or more, and still particularly preferably 20 or more).

(67) The acetic acid production method according to any one of (1) to (66), wherein crotonaldehyde is concentrated at the column bottom of the distillation column in the crotonaldehyde-removing step and is discharged, as bottoms together with acetic acid, out of the system.

(68) The acetic acid production method according to any one of (1) to (67), wherein the reactor is operated at a hydrogen partial pressure of 0.5 MPa (absolute pressure) or less (and preferably 0.2 MPa (absolute pressure) or less).

(69) The acetic acid production method according to any one of (1) to (68), wherein, in the crotonaldehyde-removing step, the distillation is performed continuously, and the liquid fed to the distillation column is charged to a portion at a level lower by 20% to 80% (two-tenths to eight-tenths) from the column top, where the level is a height level at the distillation column.

(70) The acetic acid production method according to any one of (1) to (69), wherein, of a condensate derived from overhead vapors from the distillation column in the crotonaldehyde-removing step, at least a part is refluxed to the distillation column; and at least another part is drawn as a distillate and recycled to at least one of the aqueous phase, the organic phase, and the reactor.

(71) The acetic acid production method according to any one of (1) to (70), wherein, in the crotonaldehyde-removing step, bottoms including crotonaldehyde are drawn from the column bottom of the distillation column.

(72) The acetic acid production method according to any one of (1) to (71), wherein a liquid reaction mixture in the reactor has a crotonaldehyde concentration of 5 ppm by mass or less (preferably 3 ppm by mass or less, and more preferably 2 ppm by mass or less).

(73) The acetic acid production method according to any one of (1) to (72), wherein a liquid reaction mixture in the reactor has an 2-ethylcrotonaldehyde concentration of 5 ppm by mass or less (preferably 3 ppm by mass or less, and more preferably 2 ppm by mass or less).

(74) The acetic acid production method according to any one of (1) to (73), wherein a liquid reaction mixture in the reactor has a butyl acetate concentration of 0.1 to 15 ppm by mass (preferably 1 to 12 ppm by mass, and more preferably 2 to 9 ppm by mass).

(75) The acetic acid production method according to any one of (37) to (74), wherein the vapor stream has a crotonaldehyde concentration of 0 to 5 ppm by mass (preferably 0.1 to 3 ppm by mass, and more preferably 0.2 to 2 ppm by mass).

(76) The acetic acid production method according to any one of (37) to (75), wherein the vapor stream has an 2-ethylcrotonaldehyde concentration of 0 to 3 ppm by mass (preferably 0.02 to 2 ppm by mass, and more preferably 0.03 to 0.8 ppm by mass).

(77) The acetic acid production method according to any one of (37) to (76), wherein the vapor stream has a butyl acetate concentration of 0.1 to 13 ppm by mass (preferably 0.2 to 12 ppm by mass, and more preferably 0.3 to 9 ppm by mass).

(78) The acetic acid production method according to any one of (1) to (77), further including the step of scrubbing an offgas from the process by an absorptive treatment with an absorbing solvent including acetic acid, to separate the offgas into a carbon monoxide-rich stream and an acetic acid-rich stream.

INDUSTRIAL APPLICABILITY

The acetic acid production methods according to the present invention are applicable as methods for industrially producing acetic acid through a methanol carbonylation process (methanol-acetic acid process).

REFERENCE SIGNS LIST 1 reactor
2 evaporator
3, 5, 6, 10 distillation column
4 decanter
7 ion exchange resin column
8 scrubbing system
9 acetaldehyde-removing system
16 reaction mixture feed line
17 vapor stream discharge line
18, 19 residue recycle line
54 carbon monoxide-containing gas introducing line
55, 56 potassium hydroxide introducing line
57 catalyst circulating pump
91 distillation column (first acetaldehyde-removing column)
92 extraction column
93 distillation column (second acetaldehyde-removing column)
94 distillation column (extractive distillation column)
95 decanter
96 decanter
97 distillation column (acetaldehyde-removing column)
98 distillation column (extractive distillation column)
99 decanter
200 chimney tray
300 liquid-liquid equilibrium measuring apparatus

The invention claimed is:
1. A method for producing acetic acid, the method comprising the steps of:
    (A) carbonylating methanol with carbon monoxide in a reactor in the presence of a catalytic system, acetic acid, methyl acetate, and water, to form acetic acid in a reaction mixture, the catalytic system including a metal catalyst and methyl iodide;
    (B) separating the reaction mixture, using at least one selected from evaporators and distillation columns, into:
        a stream including the metal catalyst;
        an acetic acid stream rich in acetic acid; and
        a stream richer in light ends than the acetic acid stream;
    (C) liquid-liquid separating a process stream including water, acetic acid, methyl iodide, and acetaldehyde into:
        an aqueous phase; and
        an organic phase;
    (D) removing acetaldehyde derived from the process stream by a treatment of an object, the object being selected from at least a part of at least one of the aqueous phase and the organic phase based on a factor or factors selected from the group consisting of:
        a liquid temperature in the liquid-liquid separation in the liquid-liquid separation step (C);

an acetaldehyde concentration in at least one of the aqueous phase and the organic phase;

an acetaldehyde partition coefficient;

a methyl acetate concentration in at least one of the aqueous phase and the organic phase; and a methyl acetate partition coefficient;

(E) recycling at least a part of at least one of the aqueous phase and the organic phase to the reactor; and (F) removing crotonaldehyde from at least another part of at least one of the aqueous phase and the organic phase by a distillation treatment in a distillation column, wherein the separation step (B) comprises the substep of (B') yielding, by separation using a first distillation column:

a first acetic acid stream rich in acetic acid; and an overhead stream richer in light ends than the first acetic acid stream, wherein, in the substep (B'), a crotonaldehyde concentration in the first acetic acid stream is controlled to 2.2 ppm by mass or less, wherein a reflux ratio at the first distillation column in the separation step (B) is controlled so that: the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column, and wherein the distillation column in the crotonaldehyde-removing step (F) is operated so as to meet at least one of conditions (a-i), (a-ii), and (a-iii) as follows:

(a-i) a reflux ratio at the distillation column is 0.01 or more;

(a-ii) at the distillation column, a ratio of a crotonaldehyde concentration (ppm by mass) in a distillate to a crotonaldehyde concentration (ppm by mass) in a charge liquid is less than 1;

(a-iii) at the distillation column, a ratio of a crotonaldehyde concentration (ppm by mass) in bottoms to a crotonaldehyde concentration (ppm by mass) in the charge liquid is greater than 1, and wherein the liquid-liquid separation step (C) meets at least one of conditions (b-i), (b-ii), (b-iii), (b-iv), and (b-v), and at least a part of the aqueous phase is subjected to the treatment in the acetaldehyde-removing step (D), where the conditions (b-i), (b-ii), (b-iii), (b-iv), and (b-v) are expressed as follows:

(b-i) the aqueous phase has an acetaldehyde concentration of 28.1 mass percent or less, and/or the organic phase has an acetaldehyde concentration of 24.8 mass percent or less;

(b-ii) the liquid-liquid separation is performed at a temperature of 70° C. or lower;

(b-iii) the aqueous phase has a methyl acetate concentration of 12.0 mass percent or less, and/or the organic phase has a methyl acetate concentration of 47.6 mass percent or less, and/or the totality of the methyl acetate concentration in the aqueous phase and the methyl acetate concentration in the organic phase is 59.6 mass percent or less;

(b-iv) an acetaldehyde partition coefficient is 1.1 or more, where the acetaldehyde partition coefficient is a ratio of the acetaldehyde concentration (mass percent) in the aqueous phase to the acetaldehyde concentration (mass percent) in the organic phase; and (b-v) a methyl acetate partition coefficient is 0.25 or more, where the methyl acetate partition coefficient is a ratio of the methyl acetate concentration (mass percent) in the aqueous phase to the methyl acetate concentration (mass percent) in the organic phase, or wherein the liquid-liquid separation step (C) meets at least one of conditions (b'-i), (b'-ii), (b'-iii), (b'-iv), and (b'-v), and at least a part of the organic phase is subjected to the treatment in the acetaldehyde-removing step (D), where the conditions (b'-i), (b'-ii), (b'-iii), (b'-iv), and (b'-v) are expressed as follows:

(b'-i) the aqueous phase has an acetaldehyde concentration of 0.045 mass percent or more, and/or the organic phase has an acetaldehyde concentration of 0.013 mass percent or more;

(b'-ii) the liquid-liquid separation is performed at a temperature of −5° C. or higher;

(b'-iii) the aqueous phase has a methyl acetate concentration of 1.2 mass percent or more, and/or the organic phase has a methyl acetate concentration of 2.2 mass percent or more, and/or the totality of the methyl acetate concentration in the aqueous phase and the methyl acetate concentration in the organic phase is 3.4 mass percent or more;

(b'-iv) an acetaldehyde partition coefficient is 4.1 or less, where the acetaldehyde partition coefficient is a ratio of the acetaldehyde concentration (mass percent) in the aqueous phase to the acetaldehyde concentration (mass percent) in the organic phase; and (b'-v) a methyl acetate partition coefficient is 0.8 or less, where the methyl acetate partition coefficient is a ratio of the methyl acetate concentration (mass percent) in the aqueous phase to the methyl acetate concentration (mass percent) in the organic phase.

2. A method for producing acetic acid, the method comprising the steps of:

(A) carbonylating methanol with carbon monoxide in a reactor in the presence of a catalytic system, acetic acid, methyl acetate, and water, to form acetic acid in a reaction mixture, the catalytic system including a metal catalyst and methyl iodide;

(B) separating the reaction mixture, using at least one selected from evaporators and distillation columns, into:

a stream including the metal catalyst;

an acetic acid stream rich in acetic acid; and a stream richer in light ends than the acetic acid stream;

(C) liquid-liquid separating a process stream including water, acetic acid, methyl iodide, and acetaldehyde into:

an aqueous phase; and an organic phase;

(D) removing acetaldehyde derived from the process stream by a treatment of an object, the object being selected from at least a part of at least one of the aqueous phase and the organic phase based on a factor or factors selected from the group consisting of:

a liquid temperature in the liquid-liquid separation in the liquid-liquid separation step (C);

an acetaldehyde concentration in at least one of the aqueous phase and the organic phase;
an acetaldehyde partition coefficient;
a methyl acetate concentration in at least one of the aqueous phase and the organic phase; and
a methyl acetate partition coefficient;
(E) recycling at least a part of at least one of the aqueous phase and the organic phase to the reactor; and
(F) removing crotonaldehyde from at least another part of at least one of the aqueous phase and the organic phase by a distillation treatment in a distillation column,
wherein the separation step (B) comprises the steps of:
(B") yielding, by separation using a first distillation column:
a first acetic acid stream rich in acetic acid; and
a first overhead stream richer in light ends than the first acetic acid stream; and
(B''') separating the first acetic acid stream, using a second distillation column, into:
a second overhead stream rich in water; and
a second acetic acid stream richer in acetic acid than the first acetic acid stream,
wherein, in the substeps (B1) and (B2), a crotonaldehyde concentration in the first acetic acid stream is controlled to 2.2 ppm by mass or less, and/or a reflux ratio at the second distillation column is controlled to 0.1 or more,
wherein a reflux ratio at the first distillation column in the separation step (B) is controlled so that: the reflux ratio for the aqueous phase is 2 or more when the aqueous phase alone is refluxed to the first distillation column; the reflux ratio for the organic phase is 1 or more when the organic phase alone is refluxed to the first distillation column; and the total reflux ratio for the aqueous phase and the organic phase is 1.5 or more when both the aqueous phase and the organic phase are refluxed to the first distillation column, and
wherein the distillation column in the crotonaldehyde-removing step (F) is operated so as to meet at least one of conditions (a-i), (a-ii), and (a-iii) as follows:
(a-i) a reflux ratio at the distillation column is 0.01 or more;
(a-ii) at the distillation column, a ratio of a crotonaldehyde concentration (ppm by mass) in a distillate to a crotonaldehyde concentration (ppm by mass) in a charge liquid is less than 1;
(a-iii) at the distillation column, a ratio of a crotonaldehyde concentration (ppm by mass) in bottoms to a crotonaldehyde concentration (ppm by mass) in the charge liquid is greater than 1, and
wherein the liquid-liquid separation step (C) meets at least one of conditions (b-i), (b-ii), (b-iii), (b-iv), and (b-v), and at least a part of the aqueous phase is subjected to the treatment in the acetaldehyde-removing step (D), where the conditions (b-i), (b-ii), (b-iii), (b-iv), and (b-v) are expressed as follows:
(b-i) the aqueous phase has an acetaldehyde concentration of 28.1 mass percent or less, and/or the organic phase has an acetaldehyde concentration of 24.8 mass percent or less;
(b-ii) the liquid-liquid separation is performed at a temperature of 70° C. or lower;
(b-iii) the aqueous phase has a methyl acetate concentration of 12.0 mass percent or less, and/or the organic phase has a methyl acetate concentration of 47.6 mass percent or less, and/or the totality of the methyl acetate concentration in the aqueous phase and the methyl acetate concentration in the organic phase is 59.6 mass percent or less;
(b-iv) an acetaldehyde partition coefficient is 1.1 or more, where the acetaldehyde partition coefficient is a ratio of the acetaldehyde concentration (mass percent) in the aqueous phase to the acetaldehyde concentration (mass percent) in the organic phase; and
(b-v) a methyl acetate partition coefficient is 0.25 or more, where the methyl acetate partition coefficient is a ratio of the methyl acetate concentration (mass percent) in the aqueous phase to the methyl acetate concentration (mass percent) in the organic phase,
or
wherein the liquid-liquid separation step (C) meets at least one of conditions (b'-i), (b'-ii), (b'-iii), (b'-iv), and (b'-v), and at least a part of the organic phase is subjected to the treatment in the acetaldehyde-removing step (D), where the conditions (b'-i), (b'-ii), (b'-iii), (b'-iv), and (b'-v) are expressed as follows:
(b'-i) the aqueous phase has an acetaldehyde concentration of 0.045 mass percent or more, and/or the organic phase has an acetaldehyde concentration of 0.013 mass percent or more;
(b'-ii) the liquid-liquid separation is performed at a temperature of −5° C. or higher;
(b'-iii) the aqueous phase has a methyl acetate concentration of 1.2 mass percent or more, and/or the organic phase has a methyl acetate concentration of 2.2 mass percent or more, and/or the totality of the methyl acetate concentration in the aqueous phase and the methyl acetate concentration in the organic phase is 3.4 mass percent or more;
(b'-iv) an acetaldehyde partition coefficient is 4.1 or less, where the acetaldehyde partition coefficient is a ratio of the acetaldehyde concentration (mass percent) in the aqueous phase to the acetaldehyde concentration (mass percent) in the organic phase; and
(b'-v) a methyl acetate partition coefficient is 0.8 or less, where the methyl acetate partition coefficient is a ratio of the methyl acetate concentration (mass percent) in the aqueous phase to the methyl acetate concentration (mass percent) in the organic phase.

3. The acetic acid production method according to claim 1,
wherein the liquid-liquid separation step (C) meets all the conditions (b-i), (b-ii), (b-iii), (b-iv), and (b-v).

4. The acetic acid production method according to claim 1,
wherein the liquid-liquid separation step (C) meets all the conditions (b'-i), (b'-ii), (b'-iii), (b'-iv), and (b'-v).

5. The acetic acid production method according to claim 1,
wherein the separation step (B) comprises the steps of:
(B1) evaporating the reaction mixture in an evaporator to separate the reaction mixture into a vapor stream and a residue stream; and
(B2) removing light ends by:
separating the vapor stream, using the first distillation column, into a first overhead stream rich in at least one light end selected from methyl iodide and acetaldehyde, and the first acetic acid stream rich in acetic acid; and
subjecting the first overhead stream to condensation and liquid-liquid separation to give an aqueous phase and an organic phase.

6. The acetic acid production method according to claim 5,
wherein the separation step (B) comprises the step of:
(B3) dehydrating the first acetic acid stream by separation, using a second distillation column, into:
a second overhead stream rich in water; and
a second acetic acid stream richer in acetic acid than the first acetic acid stream.

7. The acetic acid production method according to claim 4,
wherein the second acetic acid stream has a crotonaldehyde concentration of 2.0 ppm by mass or less.

8. The acetic acid production method according to claim 4,
wherein the second acetic acid stream has an 2-ethylcrotonaldehyde concentration of 3.0 ppm by mass or less.

9. The acetic acid production method according to claim 6, wherein the second acetic acid stream has a ratio ($C_{CR}/C_{ECR}$) of a crotonaldehyde concentration $C_{CR}$ (ppm by mass) to an 2-ethylcrotonaldehyde concentration $C_{ECR}$ (ppm by mass) of 50 or less.

10. The acetic acid production method according to claim 6,
wherein the second acetic acid stream has a butyl acetate concentration of 15 ppm by mass or less.

11. The acetic acid production method according to claim 6,
wherein the second acetic acid stream has a ratio ($C_{CR}/C_{BA}$) of a crotonaldehyde concentration $C_{CR}$ (ppm by mass) to a butyl acetate concentration $C_{BA}$ (ppm by mass) of 2.0 or less.

12. The acetic acid production method according to claim 1,
wherein the catalytic system further includes an ionic iodide.

13. The acetic acid production method according to claim 1,
wherein at least a part of a residue is recycled to the reactor, where the residue is a residue remained after the removal of acetaldehyde from at least a part of at least one of the aqueous phase and the organic phase.

14. The acetic acid production method according to claim 1,
wherein the reactor is operated at a hydrogen partial pressure of 0.001 MPa (absolute pressure) or more.

15. The acetic acid production method according to claim 1,
wherein a liquid reaction mixture in the reactor has an acetaldehyde concentration of 500 ppm by mass or less.

16. The acetic acid production method according to claim 1,
wherein the distillation in the crotonaldehyde-removing step (F) is performed batchwise.

17. The acetic acid production method according to claim 1,
wherein the distillation column in the crotonaldehyde-removing step (F) is operated at a throughput of 0.0001 to 50 parts by mass per 100 parts by mass of the vapor stream fed to the first distillation column.

18. The acetic acid production method according to claim 1, further comprising the step of
(G) scrubbing a process offgas by an absorptive treatment with an absorbing solvent including acetic acid, to separate the offgas into:
a carbon monoxide-rich stream; and
an acetic acid-rich stream.

* * * * *